(12) United States Patent
Trias et al.

(10) Patent No.: US 11,103,589 B2
(45) Date of Patent: Aug. 31, 2021

(54) POLYETHYLENIMINE (PEI)-POLYPEPTIDE CONJUGATES AND METHODS OF USE THEREOF

(71) Applicant: APG Therapeutics, Inc., Millbrae, CA (US)

(72) Inventors: Joaquim Trias, Millbrae, CA (US); Jaume Pons, San Francisco, CA (US); David Shelton, Oakland, CA (US); Antoni Planas, Sant Cugat del Valles (ES)

(73) Assignee: APG Therapeutics, Inc., Millbrae, CA (US)

( * ) Notice: Subject to any disclaimer, the term of this patent is extended or adjusted under 35 U.S.C. 154(b) by 657 days.

(21) Appl. No.: 16/068,660

(22) PCT Filed: Jan. 6, 2017

(86) PCT No.: PCT/US2017/012623
§ 371 (c)(1),
(2) Date: Jul. 6, 2018

(87) PCT Pub. No.: WO2017/120536
PCT Pub. Date: Jul. 13, 2017

(65) Prior Publication Data
US 2019/0091341 A1    Mar. 28, 2019

Related U.S. Application Data

(60) Provisional application No. 62/276,799, filed on Jan. 8, 2016.

(51) Int. Cl.
*A61K 47/59* (2017.01)
*A61K 47/65* (2017.01)
(Continued)

(52) U.S. Cl.
CPC .............. *A61K 47/59* (2017.08); *A61K 47/65* (2017.08); *A61K 47/68* (2017.08);
(Continued)

(58) Field of Classification Search
None
See application file for complete search history.

(56) References Cited

U.S. PATENT DOCUMENTS

| | | | |
|---|---|---|---|
| 4,816,567 A | 3/1989 | Cabilly | |
| 5,545,806 A | 8/1996 | Lonberg et al. | |

(Continued)

FOREIGN PATENT DOCUMENTS

| | | | |
|---|---|---|---|
| JP | 2015535292 A | 12/2015 | |
| KR | 20110027969 A | 3/2011 | |

(Continued)

OTHER PUBLICATIONS

Axup, J.Y. et al. (Oct. 2, 2012). "Synthesis of Site-Specific Antibody-Drug Conjugates Using Unnatural Amino Acids," Proc. Natl. Acad. Sci. USA 109(40):16101-16106.

(Continued)

*Primary Examiner* — Karl J Puttlitz
(74) *Attorney, Agent, or Firm* — Morrison & Foerster LLP

(57) ABSTRACT

The present application provides PEI compounds comprising a linker, PEI-polypeptide conjugates (e.g., PEI-antibody conjugates), and complexes thereof comprising a biologically active molecule. Methods of preparing and using the compounds, conjugates and complexes are further provided. The PEI-polypeptide conjugates and complexes are useful for delivering biologically active molecules to the cytoplasm of cells and promoting release of the biologically active molecules from the endo-lysosomal pathway.

11 Claims, 7 Drawing Sheets

Specification includes a Sequence Listing.

1. TG 2%. 2 μL of TG stock (1 mg mL$^{-1}$).
2. RF8. 68 μL of RF8 stock (3 mg mL$^{-1}$)
3. Erb001B1. 20 μL of Erbitux stock (2.5 mg mL$^{-1}$)
4. Erb001B1 +TG 2%. 20 μL of Erbitux and 2 μL of TG
5. Erb001B1 + RF8(1:10). 20 μL of Erbitux and 68 μL of PEI RF8
6. Erb001B1 + RF8(1:10) + TG. 20 μL of Erbitux, 68 μL of PEI RF8 and 2 μL of TG
7. Erb001B1 + RF8(1:3). 20 μL of Erbitux and 20 μL of PEI RF8
8. Erb001B1 + RF8(1:3) + TG. 20 μL of Erbitux, 20 μL of PEI RF8 and 2 μL of TG

(51) Int. Cl.
　　　A61K 47/68　　　(2017.01)
　　　A61K 48/00　　　(2006.01)
　　　C07J 9/00　　　　(2006.01)
　　　C08G 73/02　　　(2006.01)
　　　C07K 16/28　　　(2006.01)
　　　C07K 14/54　　　(2006.01)
(52) U.S. Cl.
　　　CPC ............ A61K 48/0041 (2013.01); C07J 9/00 (2013.01); C07K 16/28 (2013.01); C08G 73/0206 (2013.01); C07K 14/5406 (2013.01); C07K 2317/31 (2013.01); C07K 2317/82 (2013.01); C07K 2319/03 (2013.01); C07K 2319/033 (2013.01); C07K 2319/33 (2013.01)

(56) References Cited

U.S. PATENT DOCUMENTS

| | | | |
|---|---|---|---|
| 5,545,807 | A | 8/1996 | Surani |
| 5,569,825 | A | 10/1996 | Lonberg |
| 6,075,181 | A | 6/2000 | Kucherlapati |
| 6,150,584 | A | 11/2000 | Kucherlapati |
| 6,982,321 | B2 | 1/2006 | Winter |
| 7,087,409 | B2 | 8/2006 | Barbas, Iii |
| 7,863,470 | B2 * | 1/2011 | Furgeson ............... C07J 9/00 552/544 |
| 9,109,087 | B2 | 8/2015 | Cheng et al. |
| 2010/0210543 | A1 | 8/2010 | Rabuka et al. |
| 2012/0097333 | A1 | 4/2012 | Mironov |
| 2013/0230543 | A1 | 9/2013 | Pons et al. |
| 2017/0072057 | A1 | 3/2017 | Ventura et al. |

FOREIGN PATENT DOCUMENTS

| | | | |
|---|---|---|---|
| WO | 199110741 | A1 | 7/1991 |
| WO | 199633735 | A1 | 10/1996 |
| WO | 199634096 | A1 | 10/1996 |
| WO | 1998024893 | A2 | 6/1998 |
| WO | 199824893 | A3 | 8/1998 |
| WO | 2014071387 | A1 | 5/2014 |

OTHER PUBLICATIONS

Badescu, G. et al. (2014). "Bridging Disulfides for Stable and Defined Antibody Drug Conjugates," Bioconjugate Chem. 25(6):1124-1136. (Abstract).
Beerli, R. et al. (Jul. 1, 2015). "Sortase Enzyme-Mediated Generation of Site-Specifically Conjugated Antibody Drug Conjugates with High In Vitro and In Vivo Potency," PLOS ONE 10(7):e0131177, 12 pages.
Berthold, P.R. et al. (2010). "Cellular delivery and Antisense Effects of Peptide Nucleic Acid Conjugated to Polyethyleneimine via Disulfide Linkers," Bioconjugate Chem. 21(10):1933-1938.
Bloom, J.W. et al. (1997). "Intrachain Disulfide Bond in the Core Hinge Region of Human IgG4," Protein Sci. 6:407-415.
Boerner, P. et al. (Jul. 1, 1991). "Production of Antigen-Specific Human Monoclonal Antibodies From in Vitro-Primed Human Splenocytes," J. Immunol. 147(1):86-95.
Brüggemann, M. et al. (1993). "Designer Mice: The Production of Human Antibody Repertoires in Transgenic Animals," Year in Immuno. 7:33-40.
Chothia, C. et al. (1987), "Canonical Structures for the Hypervariable Regions of Immunoglobulins," J. Mol. Biol, 196:901-917.
Clackson, T. et al. (1991). "Making Antibody Fragments Using Phage Display Libraries," Nature 352:624-628.
Sole, S.P.C. et al. (1985). "The EBV-Hybridoma Technique and Its Applicaton to Human Lung Cancer," in Monoclonal Antibodies and Cancer Therapy, Alan R. Liss, p. 77-96.
Dennier, P. et al. (March 19, 2014, e-pub. Feb. 12, 2014). "Transglutaminase-Based Chemo-Enzymatic Conjugation Approach Yields Homogeneous Antibody-Drug Conjugates," Bioconjugate Chem. 25(3):569-578.

Fellouse, F.A. et al. (Aug. 24, 2004). "Synthetic Antibodies From a Four-Amino-Acid Code: A Dominant Role for Tyrosine in Antigen Recognition," Proc. Natl. Acad. Sci. USA 101(34):12467-12472.
Fishwild, D.M. et al. (Jul. 1996). "High-avidity human IgGK Monoclonal Antibodies from a Novel Strain of Minilocus Transgenic Mice," Nature Biotechnol. 14:845-851.
Hamers-Casterman, C. et al. (Jun. 3, 1993). "Naturally Occurring Antibodies Devoid of Light Chains," Nature 363:446-448.
Hammerling, G.J. et al. (1981). "Production of Antibody-Producing Hybridomas in the Rodent System," Chapter 12, in Monoclonal Antibodies and T-Cell Hybridomas, Elsevier/North Holland Biomedical Press, New York, pp. 563-681.
Harris, W.J. (1995). "Therapeutic Monoclonal. Production of Humanized Monoclonal Antibodies for In Vivo Imaging and Therapy," Biochem. Soc. Transactions 23:1035-1038.
Hein, C.D. et al. (Oct. 2008, e-pub. May 29, 2008). "Click Chemistry, A Powerful Tool for Pharmaceutical Sciences," Pharm. Res. 25(10):2216-2230.
Hongo, J.A.S. et al. (1995). "Development and Characterization of Murine Monoclonal Antibodies to the Latency-Associated Peptide of Transforming Growth Factor Beta1," Hybridoma, 14(3):253-260.
Hoogenboom, H.R. et al. (1992). "By-Passing Immunisation. Human Antibodies From Synthetic Repertoires of Germline VH Gene Segments Rearranged in Vitro," J. Mol. Biol. 227:381-388.
Humphreys, D.P. et al. (Dec. 1, 1997). "Formation of Dimeric Fabs in *Escherichia coli*: Effect of Hinge Size and Isotype, Presence of Interchain Disulphide Bond, Fab' Expression Levels, Tail Piece Sequences and Growth Conditions," J. Immunol. Methods 209(2):193-202.
Hurle, M.R. et al. (1994). "Protein Engineering Techniques for Antibody Humanization," Curr. Op. Biotech. 5:428-433.
International Preliminary Report on Patentability dated Jul. 19, 2018, for International Application No. PCT/US2017/012623, filed on Jan. 6, 2017, fifteen pages.
International Search Report and Written Opinion dated Jun. 2, 2017, for International Application No. PCT/US2017/012623, filed on Jan. 6, 2017, twenty three pages.
Invitation to Pay Additional Fees and, where Applicable, Protest Fee dated Mar. 24, 2017, for International Application No. PCT/US2017/012623 filed on Jan. 6, 2017, seven pages.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.
Johnson, G. et al. (2003). "The Kabat Database and a Bioinformatics Example," Chapter 2 in Methods in Molecular Biology, Lo, B.K.C., ed., Human Press, Totowa, N.J., 248:1-25.
Jones, P.T. et al. (May 29, 1986). "Replacing the Complementarity-Determining Regions in a Human Antibody With Those From a Mouse," Nature 321:522-525.
Junutula, J.R. et al. (2008), "Site-specific conjugation of cytotoxic drug to an antibody improves the therapeutic index," Nat Biotechnol. 26(8):925-932.
Kolb, H.C. et al. (Jun. 1, 2001; e-pub. May 28, 2001). "Click Chemistry: Diverse Chemical Function from a Few Good Reactions," Angew Chem Int Ed Engl 40(11):2004-2021.
Kostelny, S.A. et al. (Mar. 1, 1992), "Formation of a Bispecific Antibody by The Use of Leucine Zippers," J. Immunol. 148(5):1547-1553.
Köhler, G. et al. (Aug. 7, 1975). "Continuous Cultures of Fused Cells Secreting Antibody of Predefined Specificity," Nature 256:495-497.
Lee, C.V. et al. (2004). "Bivalent Antibody Phage Display Mimics Natural Immunoglobulin," J. Immunol. Methods 284(1-2):119-132.
Lee, C.V. et al. (2004). "High-affinity Human Antibodies From Phage-displayed Synthetic Fab Libraries With a Single Framework Scaffold," J. Mol. Biol. 340(5):1073-1093.
Li, J. et al. (Mar. 7, 2006). Human Antibodies for Immunotherapy Development Generated via a Human B Cell Hybridoma Technology, Proc. Natl. Acad. Sci. USA 103(10):3557-3562.

(56) References Cited

OTHER PUBLICATIONS

Liu, C.C. et al. (2010, e-pub. Mar. 18, 2010). "Adding New Chemistries to the Genetic Code," Annual Review of Biochemistry 79:413-444.

Lonberg, N. et al. (Apr. 28, 1994). "Antigen-Specific Human Antibodies From Mice Comprising Four Distinct Genetic Modifications," Nature 368:856-859.

Lonberg, N. et al. (1995). "Human Antibodies From Transgenic Mice," Intern. Rev. Immunol. 13:65-93.

Loudon, G.M. (2002). Organic Chemistry, Fourth Edition, Oxford University Press, New York, pp. 360-361.

Marks, J.D. et al. (Jul. 1992). "By-Passing Immunization: Building High Affinity Human Antibodies by Chain Shuffling," Bio/Technology 10:779-783.

Morrison, S.L. (Apr. 28, 1994). "Success in Specification," Nature 368:812-813.

Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.

Neuberger, M. (Jul. 1996). "Generating High-Avidity Human Mabs in Mice," Nature Biotechnol. 14:826.

Ou, W. et al. (Jun. 28, 2011). "Site-Specific Protein Modification Through Pyrroline-Carboxy-Lysine Residues," Proc. Natl. Acad. Sci. USA 108(26):10437-10442.

Presta, L.G. (1992). "Antibody Engineering," Current Opinion in Structural Biology 2:593-596.

Riechmann, L. et al. (Mar. 1988). "Reshaping Human Antibodies for Therapy," Nature 332:323-329.

Sheriff, S. et al. (Sep. 1996). "Redefining the Minimal Antigen-Binding Fragment," Nature Struct. Biol. (9):733-736.

Sidhu, S.S. et al. (2004). "Phage-Displayed Antibody Libraries Synthetic Heavy Chain Complementarity Determining Regions," J. Mol. Biol. 338(2):299-310.

Sochaj, A.M. et al. (Nov. 1, 2015): "Current Methods for the Synthesis of Homogeneous Antibody-Drug Conjugates," 33(6, Part 1):775-784. (Abstract).

Songsivilai, S. et al. (1990). "Bispecific Antibody: A Tool for Diagnosis and Treatment of Disease," Clin. Exp. Immunol. 79:315-321.

Tian, F. et al. (Feb. 4, 2014). "A General Approach to Site-Specific Antibody Drug Conjugates," Proc Nat Acad Sci USA 111(5):1766-1771.

Van Dijk, M.A. et al. (2001). "Human Antibodies as Next Generation Therapeutics," Curr. Opin. Pharmacol. 5:368-374.

Vaswani, S.K. et al. (Aug. 1998). "Humanized Antibodies as Potential Therapeutic Drugs," Ann. Allergy, Asthma & Immunol. 1:105-115.

Xu, J.L. et al. (Jul. 2000). "Diversity in the CDR3 Region of VH is Sufficient for Most Antibody Specificities," Immunity 13:37-45.

Zeglis, B.M. et al. (Jun. 19, 2013). "An Enzyme-Mediated Methodology for the Site-Specific Radiolabeling of Antibodies Based on Catalyst-Free Click Chemistry," Bioconjugate Chem. 24(6):1057-1067, 23 pages.

Zhou, Q. et al. (2014; e-pub. Feb. 17, 2014). "Site-Specific Antibody-Drug Conjugation through Glycoengineering," Bioconjug Chem 25(3):510-520.

Zhou, Z. et al. (2014). "Comparison of Site-Specific Pegylations of the N-Terminus of Interferon Beta-1b: Selectivity, Efficiency, and In Vivo/Vitro Activity," Bioconjug. Chem. 25(1):138-146.

Zimmerman, E.S. et al. (Jan. 17, 2014). "Production of Site-Specific Antibody-Drug Conjugates Using Optimized Non-Natural Amino Acids in a Cell-Free Expression System," Bioconjugate Chem. 25:351-361.

\* cited by examiner

1. TG 2%. 2 μL of TG stock (1 mg mL$^{-1}$).
2. RF8. 68 μL of RF8 stock (3 mg mL$^{-1}$)
3. Erb001B1. 20 μL of Erbitux stock (2.5 mg mL$^{-1}$)
4. Erb001B1 +TG 2%. 20 μL of Erbitux and 2 μL of TG
5. Erb001B1 + RF8(1:10). 20 μL of Erbitux and 68 μL of PEI RF8
6. Erb001B1 + RF8(1:10) + TG. 20 μL of Erbitux, 68 μL of PEI RF8 and 2 μL of TG
7. Erb001B1 + RF8(1:3). 20 μL of Erbitux and 20 μL of PEI RF8
8. Erb001B1 + RF8(1:3) + TG. 20 μL of Erbitux, 20 μL of PEI RF8 and 2 μL of TG 1. Erb001B1 + RF6. No TG.
2. Erb001B1 + RF6 + TG.
3. Erb001B1 + RF7. No TG.
4. Erb001B1 + RF7 + TG.
5. Erb001B1 + RF8. No TG.
6. Erb001B1 + RF8 + TG.

1. Erb001B + AB7751. No TG.
2. Erb001B + AB7751 + TG.
3. Erb001B + AB7752. No TG.
4. Erb001B + AB7752 + TG.
5. Erb001B + AB7753. No TG.
6. Erb001B + AB7753 + TG.
7. Erb001B + AB7769. No TG.
8. Erb001B + AB7769 + TG.
9. Erb001B + AB7776. No TG.
10. Erb001B + AB7776 + TG.
11. Erb001B + RF8. No TG.
12. Erb001B + RF8 + TG.

FIG. 4A Erb001B1: 1-hour incubation
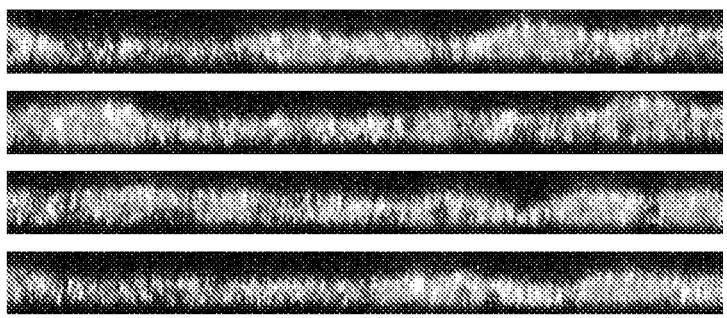
FIG. 4B Erb001B1: 4-hour incubation
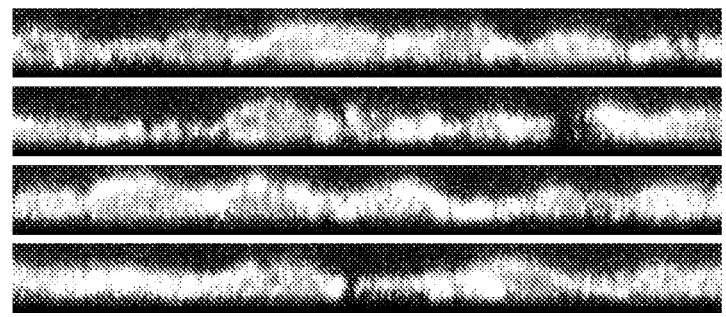

FIG. 5A    Erb001B1-RF8: 1-hour incubation
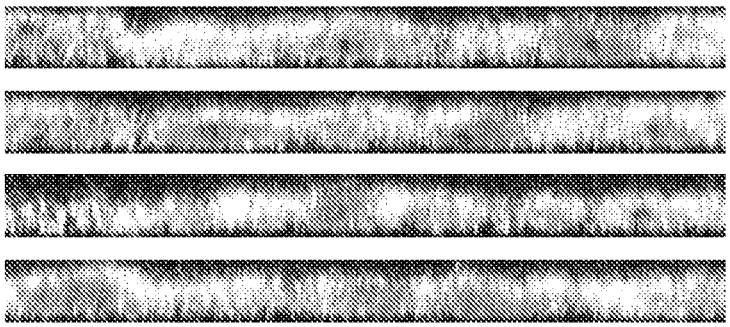
FIG. 5B    Erb001B1-RF8: 4-hour incubation
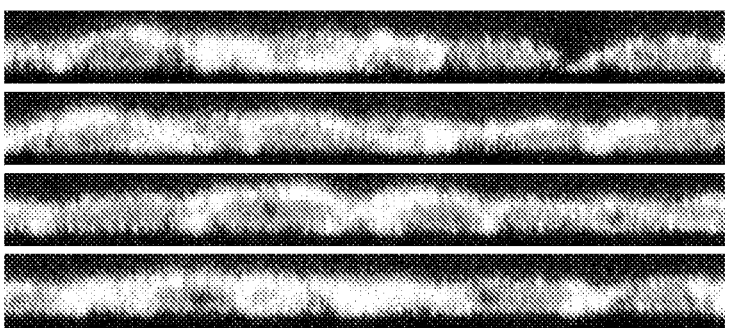

Erb001B1-RF8: 4-hour incubation with HEK293T cells

FIG. 7 Erb001B1-RF8 (25 µg/mL) + 6-FAM-oligonucleotide
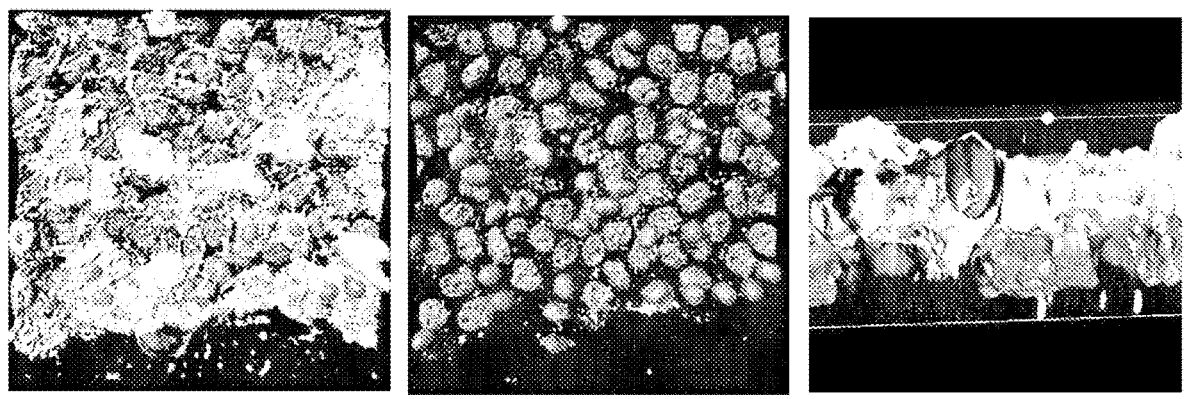

POLYETHYLENIMINE (PEI)-POLYPEPTIDE CONJUGATES AND METHODS OF USE THEREOF

CROSS REFERENCE TO RELATED APPLICATIONS

This application is a National Phase application under 35 U.S.C. § 371 of International Application No. PCT/US2017/012623, filed Jan. 6, 2017, which claims priority to U.S. Provisional Patent Application No. 62/276,799, filed Jan. 8, 2016, the disclosures of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 717422000100SEQLIST.txt, date recorded: Dec. 11, 2018, size: 11 KB).

TECHNICAL FIELD

The present disclosure relates to PEI-polypeptide conjugates (e.g., PEI-antibody conjugates) and methods of preparing the conjugates thereof. The present disclosure also relates to methods of delivering a biologically active moiety to the cytoplasm of cells using the PEI-polypeptide conjugates.

BACKGROUND OF THE INVENTION

Polyethylenimine (PEI) is a polycationic polymer that has found wide applications as a transfection agent for nucleic acids. PEI can condense nucleic acids via electrostatic interactions into positively charged particles known as polyplexes, which bind to the negatively charged cell membrane and are consequently endocytosed into the cell. Additionally, the high pH-buffering capacity of PEI disrupts the acidic environment of endosomes and lysosomes, allowing rapid escape of the polyplexes from the endo-lysosomal pathway, thereby protecting the cargo from degradation by endosomal or lysosomal enzymes. PEI has been shown to mediate efficient nucleic acid delivery into the cytoplasm and nuclei of a variety of cells.

However, there remain several challenges in using PEI as an effective delivery vehicle for therapeutic agents. First, unmodified PEI can only form stable non-covalent complexes with negatively charged agents. Thus, PEI has not been widely used in the delivery of molecular modalities other than nucleic acids. Also, PEI is highly cytotoxic. At a high PEI to nucleic acid ratio, which is normally required for high transfection efficiency, the positively charged polyplexes can disrupt the cell membrane leading to immediate necrotic cell death, or disrupt the mitochondrial membrane after internalization leading to a delayed apoptosis. Importantly, unmodified PEI lacks target cell specificity. Yet, targeted drug delivery is recognized in many fields of therapy as a key element that has major impacts on the efficacy of a therapeutic agent and on patients' quality of life.

Many targeted drug delivery methods have recently been developed. Antibodies are large extracellular proteins that recognize unique antigens. They are widely used as therapeutic agents due to their specificity. This specificity can be used to target any cell, tissue, or foreign body with an antigen on the surface. Antibodies are used to target extracellular antigens, either as a therapeutic agent by itself or as a delivery moiety for another therapeutic agent. For example, a large number of therapeutic antibodies have been used to treat cancer, inflammation, metabolic diseases, or other diseases and conditions. There have also been many attempts to use antibodies for delivery, for example, as part of a liposome that contains a drug, or linked to a drug moiety, wherein the drug is delivered to the target cell that expresses an antigen to which the antibody binds to. Similarly, non-antibody ligands targeting a variety of cell-surface receptors have been used as part of a delivery system to target tissues and organs that specifically express the receptors.

PEI conjugates with targeting polypeptides, such as antibodies and ligands of cell-surface receptors have been constructed to address the unmet needs of an efficient, targeted intracellular delivery vehicle for nucleic acids. However, most of the current conjugation methods are non-specific on both the PEI component and the targeting polypeptide component, unavoidably yielding a heterogeneous mixture of conjugates that differ in properties including, but not limited to, molar ratios of PEI to the targeting polypeptide, conjugation sites, conjugation efficiency, efficacy, safety, pharmacokinetics and pharmacodynamics. Also, the conjugation reactions involve complicated processes with lengthy reaction procedures, such as oxidations and reductions, which may result in aggregation of the targeting polypeptides. Accordingly, versatile and site-specific PEI linkers and their conjugates with polypeptides are needed for targeted delivery of biologically active agents of a variety of molecular modalities.

The disclosures of all publications, patents, patent applications and published patent applications referred to herein are hereby incorporated herein by reference in their entirety.

BRIEF SUMMARY OF THE INVENTION

Provided herein are polypeptide-PEI conjugates, and methods for producing and using the polypeptide-PEI conjugates.

In one aspect of the present application, there is provided a compound of the formula (I):

PEI-L$^{10}$-FG      (I)

or a salt thereof, wherein

PEI is polyethylenimine, which terminates with —OH or —NHR, wherein R is hydrogen or C$_{1-6}$ alkyl;

L$^{10}$ is a linker; and

FG is a functional group that is reactive in a thiol modification reaction, a click reaction, or an enzymatic reaction;

wherein the L$^{10}$ can be connected to PEI at the terminus or in an interior repeat unit of PEI. In some embodiments, the PEI has a molecular weight of about 2500 to about 50,000, such as about 5000 to about 15,000.

In one aspect of the present application, there is provided a compound of the formula (II):

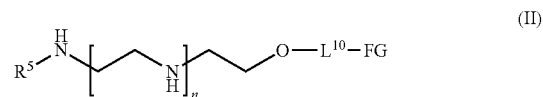

or a salt thereof, wherein $R^5$ is hydrogen or optionally substituted $C_{1-6}$ alkyl;

n is a number from one to 1200;

$L^{10}$ is a linker; and

FG is a functional group that is reactive in a thiol modification reaction, a click reaction, or an enzymatic reaction.

In one aspect of the present application, there is provided a compound of the formula (III):

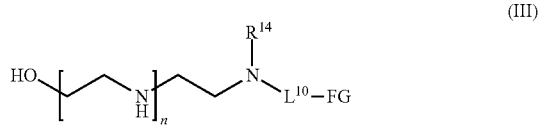
(III)

or a salt thereof, wherein n is a number from one to 1200;

$L^{10}$ is a linker;

FG is a functional group that is reactive in a thiol modification reaction, a click reaction, or an enzymatic reaction;

$R^{14}$ is hydrogen, optionally substituted $C_{1-6}$ alkyl, or

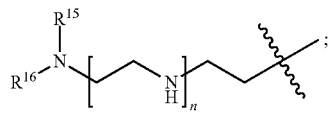;

wherein $R^{15}$ is hydrogen or optionally substituted $C_{1-6}$ alkyl;

$R^{16}$ is hydrogen or optionally substituted $C_{1-6}$ alkyl; and p is a number from one to 1200.

In some embodiments according to any one of the compounds of the formula (I), (II) and (III) as described above, FG is

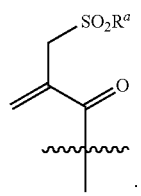

In some embodiments, FG is

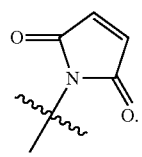

In some embodiments, FG is selected from azido, alkynyl, alkenyl, oxiranyl, thiiranyl, aziridinyl, aldehyde, acyl, alkoxyamino, hydrazine, and amino. In some embodiments, FG is selected from azido and dibenzocyclooctyl (DBCO). In some embodiments, FG is hydroxylamine, $H_2N$—O—. In some embodiments, FG is Gly-Gly-Gly.

In some embodiments according to any one of the compounds of the formula (I), (II) and (III) as described above, $L^{10}$ is $-SiR^1R^2-(CH_2)_a-$, $-SiR^1R^2-(CH_2)_a-NH-C(O)-NH-(CH_2)_b-$, $-SiR^1R^2-(CH_2)_a-C(O)-NH-(CH_2)_b-$, or $-SiR^1R^2-(CH_2)_a-NH-C(O)-(CH_2)_b-$; wherein $R^1$ and $R^2$ are independently optionally substituted $C_{1-6}$ alkyl, optionally substituted aryl, or optionally substituted heteroaryl; a is a number from one to 20; and b is a number from one to 20. In some embodiments, $L^{10}$ is $-(C_6H_4)-(CH_2)_c-$, $-(C_6H_4)-NH-(CH_2)_c-$, $-(C_6H_4)-C(O)-NH-(CH_2)_c-$, $(C_6H_4)-NH-(CH_2CH_2O)_d-CH_2CH_2-$, or $-(C_6H_4)-C(O)-NH-(CH_2CH_2O)_d-CH_2CH_2-$; wherein c is a number from one to 10; and d is a number from one to 10. In some embodiments, $L^{10}$ is $-C(O)-(C_6H_4)-(CH_2)_e-$ or $-C(O)-(CH_2)_e-$; and e is a number from one to 10.

In one aspect of the present application, there is provided a compound of the formula (IV):

(IV)

or a salt thereof, wherein

PEI is polyethylenimine, which terminates with —OH or —NHR, wherein R is hydrogen or $C_{1-6}$ alkyl;

$L^{10}$ is a linker;

q is a number from one to 100; and $R^{20}$ is a polypeptide. In some embodiments, the linkage between $R^{20}$ and $L^{10}$ is formed via a thiol modification reaction, a click reaction, or an enzymatic reaction. In some embodiments, q is one.

In some embodiments according to any one of the compounds of the formula (IV) described above, $L^{10}$ is $-SiR^1R^2-(CH_2)_a-$, $-SiR^1R^2-(CH_2)_a-NH-C(O)-NH-(CH_2)_b-$, $-SiR^1R^2-(CH_2)_a-C(O)-NH-(CH_2)_b-$, or $-SiR^1R^2-(CH_2)_a-NH-C(O)-(CH_2)_b-$; wherein $R^1$ and $R^2$ are independently optionally substituted $C_{1-6}$ alkyl, optionally substituted aryl, or optionally substituted heteroaryl; a is a number from one to 20; and b is a number from one to 20. In some embodiments, $L^{10}$ is $-(C_6H_4)-(CH_2)_c-$, $-(C_6H_4)-NH-(CH_2)_c-$, $-(C_6H_4)-C(O)-NH-(CH_2)_c-$, $(C_6H_4)-NH-(CH_2CH_2O)_d-CH_2CH_2-$, or $-(C_6H_4)-C(O)-NH-(CH_2CH_2O)_d-CH_2CH_2-$; wherein c is a number from one to 10; and d is a number from one to 10. In some embodiments, $L^{10}$ is $-C(O)-(C_6H_4)-(CH_2)_e-$ or $-C(O)-(CH_2)_e-$; and e is a number from one to 10.

In some embodiments according to any one of the compounds of the formula (IV) described above, $R^{20}$ is a targeting polypeptide, such as an Fc-containing polypeptide or a Fab-containing polypeptide, for example, an antibody. In some embodiments, $R^{20}$ specifically binds to an intracellular molecule. In some embodiments, $R^{20}$ specifically binds to an extracellular molecule. In some embodiments, $R^{20}$ is a multispecific antibody, such as a multispecific antibody comprising a first binding domain that specifically binds to an extracellular molecule and a second binding domain and specifically binds to an intracellular molecule.

In one aspect of the present application, there is provided a complex comprising a) a compound of formula (IV):

(IV)

or a salt thereof, wherein

PEI is polyethylenimine, which terminates with —OH or —NHR, wherein R is hydrogen or $C_{1-6}$ alkyl;

$L^{10}$ is a linker;

q is a number from one to 100; and $R^{20}$ is a polypeptide; and b) a biologically active molecule. In some embodiments, $R^{20}$ is a targeting polypeptide. In some embodiments, the biologically active molecule is non-covalently associated with the compound of formula (IV). In some embodiments, the biologically active molecule is covalently associated with the compound of formula (IV). In some embodiments, the biologically active molecule is a charged molecule. In some embodiments, the biologically active molecule is an oligonucleotide, DNA or RNA. In some embodiments, the biologically active molecule is a second polypeptide. In some embodiments, the complex further comprises a second biologically active molecule. In some embodiments, the biologically active molecule is a second polypeptide, and wherein the second polypeptide is conjugated to the second biologically active molecule.

In one aspect of the present application, there is provided a multifunctional linker of formula (V):

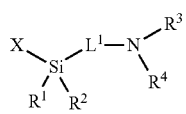

(V)

or a salt thereof, wherein

X is a leaving group selected from the group consisting of halogen and —OSO$_2$R$^x$, wherein R$^x$ is an optionally substituted C$_{1-6}$ alkyl, an optionally substituted aryl, or an optionally substituted heteroaryl;

R$^1$ and R$^2$ are independently optionally substituted C$_{1-6}$ alkyl, optionally substituted aryl, or optionally substituted heteroaryl;

R$^3$ and R$^4$ are independently hydrogen, C$_{1-6}$ alkyl, or an amino protecting group;

L$^1$ is —(CH$_2$)$_a$, (CH$_2$)$_a$—, —(CH$_2$)$_a$—NH—C(O)—NH—(CH$_2$)$_b$—, —(CH$_2$)$_a$—C(O)—NH—(CH$_2$)$_b$—, or —(CH$_2$)$_a$ NH—C(O)—(CH$_2$)$_b$—;

a is a number from one to 20; and b is a number from one to 20.

In one aspect of the present application, there is provided a compound of formula (VI):

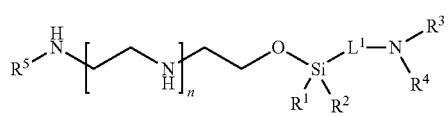

(VI)

or a salt thereof, wherein

R$^1$ and R$^2$ are independently optionally substituted C$_{1-6}$ alkyl, optionally substituted aryl, or optionally substituted heteroaryl;

R$^3$ and R$^4$ are independently hydrogen, C$_{1-6}$ alkyl, or an amino protecting group;

R$^5$ is hydrogen or optionally substituted C$_{1-6}$ alkyl;

n is a number from one to 1200;

L$^1$ is —(CH$_2$)$_a$, (CH$_2$)$_a$—, —(CH$_2$)$_a$—NH—C(O)—NH—(CH$_2$)$_b$—, —(CH$_2$)$_a$—C(O)—NH—(CH$_2$)$_b$—, or —(CH$_2$)$_a$—NH—C(O)—(CH$_2$)$_b$—;

a is a number from one to 20; and b is a number from one to 20.

In one aspect of the present application, there is provided a compound of formula (VII):

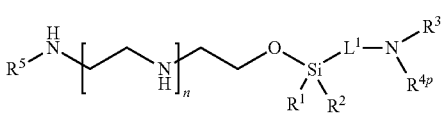

(VII)

or a salt thereof, wherein

R$^1$ and R$^2$ are independently optionally substituted C$_{1-6}$ alkyl, optionally substituted aryl, or optionally substituted heteroaryl;

R$^3$ is hydrogen or C$_{1-6}$ alkyl;

R$^{4p}$ is a polypeptide, wherein the linkage between R$^{4p}$ and N is with an acyl donor glutamine tag from the polypeptide;

R$^5$ is hydrogen or optionally substituted C$_{1-6}$ alkyl;

n is a number from one to 1200;

L$^1$ is —(CH$_2$)$_a$—, —(CH$_2$)$_a$—NH—C(O)—NH—(CH$_2$)$_b$—, —(CH$_2$)$_a$—C(O)—NH—(CH$_2$)$_b$—, or —(CH$_2$)$_a$ NH—C(O)—(CH$_2$)$_b$—;

a is a number from one to 20; and b is a number from one to 20. In some embodiments, R$^{4p}$ is a targeting polypeptide, such as an Fc-containing polypeptide or a Fab-containing polypeptide, for example, an antibody. In some embodiments, R$^{4p}$ specifically binds to an intracellular molecule. In some embodiments, R$^{4p}$ specifically binds to an extracellular molecule. In some embodiments, R$^{4p}$ is a multispecific antibody, for example, a multispecific antibody comprises a first binding domain that specifically binds to an extracellular molecule and a second binding domain and specifically binds to an intracellular molecule.

In one aspect of the present application, there is provided a complex comprising a) a compound of formula (VII):

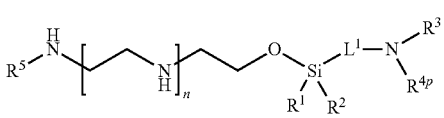

(VII)

or a salt thereof, wherein

R$^1$ and R$^2$ are independently optionally substituted C$_{1-6}$ alkyl, optionally substituted aryl, or optionally substituted heteroaryl;

R$^3$ is hydrogen or C$_{1-6}$ alkyl;

R$^{4p}$ is a polypeptide, wherein the linkage between R$^{4p}$ and N is with an acyl donor glutamine tag from the polypeptide;

R$^5$ is hydrogen or optionally substituted C$_{1-6}$ alkyl;

n is a number from one to 1200;

L$^1$ is —(CH$_2$)$_a$—, —(CH$_2$)$_a$—NH—C(O)—NH—(CH$_2$)$_b$—, —(CH$_2$)$_a$—C(O)—NH—(CH$_2$)$_b$—, or —(CH$_2$)$_a$NH—C(O)—(CH$_2$)$_b$—;

a is a number from one to 20; and b is a number from one to 20; and b) a biologically active molecule. In some embodiments, R$^{4p}$ is a targeting polypeptide. In some embodiments, the biologically active molecule is non-covalently associated with the compound of formula (VII). In some embodiments, the biologically active molecule is covalently associated with the compound of formula (VII). In some embodiments, the biologically active molecule is a charged molecule. In some embodiments, the biologically active molecule is an oligonucleotide, DNA or RNA. In some embodiments, the biologically active molecule is a second polypeptide. In some embodiments, the complex further comprises a second biologically active molecule. In some embodiments, the biologically active molecule is a second polypeptide, and wherein the second polypeptide is conjugated to the second biologically active molecule.

In one aspect of the present application, there is provided a method of preparing a compound of formula (VI):

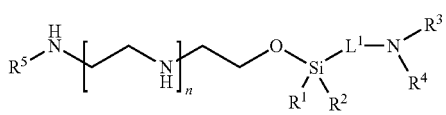
(VI)

or a salt thereof, wherein $R^1$ and $R^2$ are independently optionally substituted $C_{1-6}$ alkyl, optionally substituted aryl, or optionally substituted heteroaryl;

$R^3$ and $R^4$ are independently hydrogen, $C_{1-6}$ alkyl, or an amino protecting group;

$R^5$ is hydrogen or optionally substituted $C_{1-6}$ alkyl;

n is a number from one to 1200;

$L^1$ is —$(CH_2)_a$, $(CH_2)_a$—, —$(CH_2)_a$—NH—C(O)—NH—$(CH_2)_b$—, —$(CH_2)_a$—C(O)—NH—$(CH_2)_b$—, or —$(CH_2)_a$—NH—C(O)—$(CH_2)_b$—;

a is a number from one to 20; and b is a number from one to 20;

wherein the method comprises:

a) protonating a compound of formula (a)

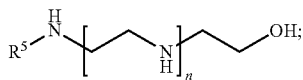
(a)

and b) mixing the protonated compound of formula (a) with a compound of formula (b):

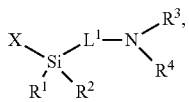
(b)

wherein X is a leaving group selected from the group consisting of halogen and —$OSO_2R$, wherein R is an optionally substituted $C_{1-6}$ alkyl, an optionally substituted aryl, or an optionally substituted heteroaryl.

In some embodiments according to any one of the compounds of the formula (VII) described above, there is provided a method of preparing the compound, wherein the method comprises:

contacting a compound of formula (VI):

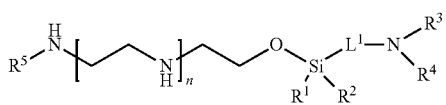
(VI)

or a salt thereof, wherein $R^1$ and $R^2$ are independently optionally substituted $C_{1-6}$ alkyl, optionally substituted aryl, or optionally substituted heteroaryl;

$R^3$ and $R^4$ are independently hydrogen, $C_{1-6}$ alkyl, or an amino protecting group;

$R^5$ is hydrogen or optionally substituted $C_{1-6}$ alkyl;

n is a number from one to 1200;

$L^1$ is —$(CH_2)_a$, $(CH_2)_a$—, —$(CH_2)_a$—NH—C(O)—NH—$(CH_2)_b$—, —$(CH_2)_a$—C(O)—NH—$(CH_2)_b$—, or —$(CH_2)_a$—NH—C(O)—$(CH_2)_b$—;

a is a number from one to 20; and b is a number from one to 20;

with a polypeptide having an acyl donor glutamine tag in the presence of transglutaminase, wherein the $C_{1-6}$ alkyl or amino protecting group of $R^3$ and $R^4$ are removed before contact with the polypeptide if $C_{1-6}$ alkyl or amino protecting group are present in $R^3$ and $R^4$.

In some embodiments according to any one of the complexes comprising the compound of the formula (VII) described above, there is provided a method of preparing the complex, wherein the method comprises: contacting a compound of formula (VII):

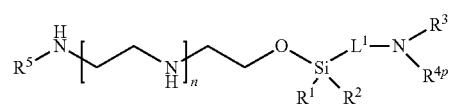
(VII)

or a salt thereof, wherein $R^1$ and $R^2$ are independently optionally substituted $C_{1-6}$ alkyl, optionally substituted aryl, or optionally substituted heteroaryl;

$R^3$ is hydrogen or $C_{1-6}$ alkyl;

$R^{4p}$ is a polypeptide, wherein the linkage between $R^{4p}$ and N is with an acyl donor glutamine tag from the polypeptide;

$R^5$ is hydrogen or optionally substituted $C_{1-6}$ alkyl;

n is a number from one to 1200;

$L^1$ is —$(CH_2)_a$—, —$(CH_2)_a$—NH—C(O)—NH—$(CH_2)_b$—, —$(CH_2)_a$—C(O)—NH—$(CH_2)_b$—, or —$(CH_2)_a$—NH—C(O)—$(CH_2)_b$—;

a is a number from one to 20; and b is a number from one to 20;

with a biologically active molecule.

In one aspect of the present application, there is provided a compound of the formula (VIII):

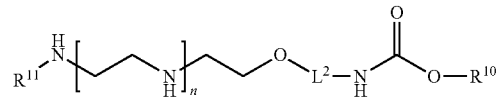
(VIII)

or a salt thereof, wherein $R^{10}$ is a solid phase resin;

$R^{11}$ is hydrogen or optionally substituted $C_{1-6}$ alkyl;

n is a number from one to 1200;

$L^2$ is —$(C_6H_4)$—$(CH_2)_c$—, —$(C_6H_4)$—NH—$(CH_2)_c$—, —$(C_6H_4)$—C(O)—NH—$(CH_2)_c$—, —$(C_6H_4)$—NH—$(CH_2CH_2O)_d$—$CH_2CH_2$—, or —$(C_6H_4)$—C(O)—NH—$(CH_2CH_2O)_d$—$CH_2CH_2$—;

c is a number from one to 10; and d is a number from one to 10.

In one aspect of the present application, there is provided a compound of the formula (IX):

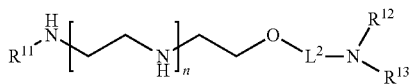
(IX)

or a salt thereof, wherein
$R^{11}$ is hydrogen or optionally substituted $C_{1-6}$ alkyl;
$R^{12}$ is hydrogen or optionally substituted $C_{1-6}$ alkyl;
$R^{13}$ is hydrogen or optionally substituted $C_{1-6}$ alkyl;
n is a number from one to 1200;
$L^2$ is $-(C_6H_4)-(CH_2)_c-$, $-(C_6H_4)-NH-(CH_2)_c-$, $-(C_6H_4)-C(O)-NH-(CH_2)_c-$, $-(C_6H_4)-NH-(CH_2CH_2O)_d-CH_2CH_2-$, or $-(C_6H_4)-C(O)-NH-(CH_2CH_2O)_d-CH_2CH_2-$;
c is a number from one to 10; and
d is a number from one to 10.

In one aspect of the present application, there is provided a compound of the formula (X):

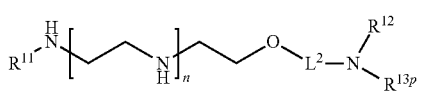
(X)

or a salt thereof, wherein
$R^{11}$ is hydrogen or optionally substituted $C_{1-6}$ alkyl;
$R^{12}$ is hydrogen or optionally substituted $C_{1-6}$ alkyl;
$R^{13p}$ is a polypeptide, wherein the linkage between $R^{13p}$ and N is with an acyl donor glutamine tag from the polypeptide;
n is a number from one to 1200;
$L^2$ is $-(C_6H_4)-(CH_2)_c-$, $-(C_6H_4)-NH-(CH_2)_c-$, $-(C_6H_4)-C(O)-NH-(CH_2)_c-$, $-(C_6H_4)-NH-(CH_2CH_2O)_d-CH_2CH_2-$, or $-(C_6H_4)-C(O)-NH-(CH_2CH_2O)_d-CH_2CH_2-$;
c is a number from one to 10; and
d is a number from one to 10. In some embodiments, $R^{13p}$ is a targeting polypeptide, such as an Fc-containing polypeptide or a Fab-containing polypeptide, for example, an antibody. In some embodiments, $R^{13p}$ specifically binds to an intracellular molecule. In some embodiments, $R^{13p}$ specifically binds to an extracellular molecule. In some embodiments, $R^{13p}$ is a multispecific antibody, such as a multispecific antibody comprises a first binding domain that specifically binds to an extracellular molecule and a second binding domain and specifically binds to an intracellular molecule.

In one aspect of the present application, there is provided a complex comprising
a) a compound of the formula (X):

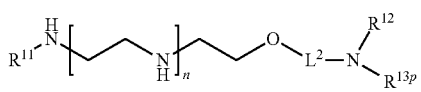
(X)

or a salt thereof, wherein
$R^{11}$ is hydrogen or optionally substituted $C_{1-6}$ alkyl;
$R^{12}$ is hydrogen or optionally substituted $C_{1-6}$ alkyl;
$R^{13p}$ is a polypeptide, wherein the linkage between $R^{13p}$ and N is with an acyl donor glutamine tag from the polypeptide;
n is a number from one to 1200;
$L^2$ is $-(C_6H_4)-(CH_2)_c-$, $-(C_6H_4)-NH-(CH_2)_c-$, $-(C_6H_4)-C(O)-NH-(CH_2)_c-$, $-(C_6H_4)-NH-(CH_2CH_2O)_d-CH_2CH_2-$, or $-(C_6H_4)-C(O)-NH-(CH_2CH_2O)_d-CH_2CH_2-$;
c is a number from one to 10; and
d is a number from one to 10; and
b) a biologically active molecule. In some embodiments, $R^{13p}$ is a targeting polypeptide. In some embodiments, the biologically active molecule is non-covalently associated with the compound of formula (X). In some embodiments, the biologically active molecule is covalently associated with the compound of formula (X). In some embodiments, the biologically active molecule is a charged molecule. In some embodiments, the biologically active molecule is an oligonucleotide, DNA or RNA. In some embodiments, the biologically active molecule is a second polypeptide. In some embodiments, the complex further comprises a second biologically active molecule. In some embodiments, the biologically active molecule is a second polypeptide, and wherein the second polypeptide is conjugated to the second biologically active molecule.

In some embodiments according to any one of the compounds of the formula (X) described above, there is provided a method of preparing the compound, wherein the method comprises
reacting a compound of formula (IX)

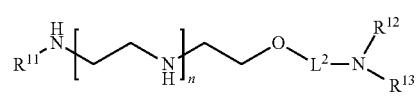
(IX)

or a salt thereof, wherein
$R^{11}$ is hydrogen or optionally substituted $C_{1-6}$ alkyl;
$R^{12}$ is hydrogen or optionally substituted $C_{1-6}$ alkyl;
$R^{13}$ is hydrogen or optionally substituted $C_{1-6}$ alkyl;
n is a number from one to 1200;
$L^2$ is $-(C_6H_4)-(CH_2)_c-$, $-(C_6H_4)-NH-(CH_2)_c-$, $-(C_6H_4)-C(O)-NH-(CH_2)_c-$, $-(C_6H_4)-NH-(CH_2CH_2O)_d-CH_2CH_2-$, or $-(C_6H_4)-C(O)-NH-(CH_2CH_2O)_d-CH_2CH_2-$;
c is a number from one to 10; and
d is a number from one to 10;
with a polypeptide having an acyl donor glutamine tag in the presence of transglutaminase,
wherein the $C_{1-6}$ alkyl group of $R^{12}$ and $R^{13}$ are removed before contact with the polypeptide if $C_{1-6}$ alkyl are present in $R^{12}$ and $R^{13}$.

In some embodiments according to any one of the complexes comprising the compound of the formula (X) described above, there is provided a method of preparing the complex, wherein the method comprises:
contacting a compound of formula (X)

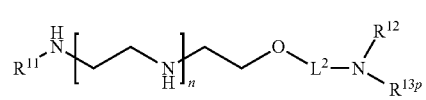
(X)

or a salt thereof, wherein $R^{11}$ is hydrogen or optionally substituted $C_{1-6}$ alkyl;
$R^{12}$ is hydrogen or optionally substituted $C_{1-6}$ alkyl;
$R^{13p}$ is a polypeptide, wherein the linkage between $R^{13p}$ and N is with an acyl donor glutamine tag from the polypeptide;
n is a number from one to 1200;
$L^2$ is —($C_6H_4$)—($CH_2$)$_c$—, —($C_6H_4$)—NH—($CH_2$)$_c$—, —($C_6H_4$)—C(O)—NH—($CH_2$)$_c$—, —($C_6H_4$)—NH—($CH_2CH_2O$)$_d$—$CH_2CH_2$—, or —($C_6H_4$)—C(O)—NH—($CH_2CH_2O$)$_d$—$CH_2CH_2$—;
c is a number from one to 10; and
d is a number from one to 10;
with a biologically active molecule.

In one aspect of the present application, there is provided a compound of the formula (XI):

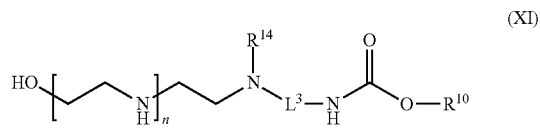

(XI)

or a salt thereof, wherein
$R^{10}$ is a solid phase resin;
$R^{14}$ is hydrogen, optionally substituted $C_{1-6}$ alkyl, or

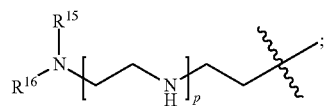

$R^{15}$ is hydrogen or optionally substituted $C_{1-6}$ alkyl;
$R^{16}$ is hydrogen or optionally substituted $C_{1-6}$ alkyl;
n is a number from one to 1200;
p is a number from one to 1200;
$L^3$ is —C(O)—($C_6H_4$)—($CH_2$)$_e$— or —C(O)—($CH_2$)$_e$—; and
e is a number from one to 10.

In one aspect of the present application, there is provided a compound of the formula (XII):

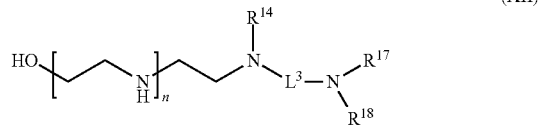

(XII)

or a salt thereof, wherein
$R^{14}$ is hydrogen, optionally substituted $C_{1-6}$ alkyl, or

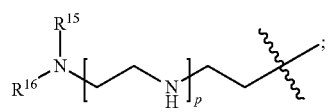

$R^{15}$ is hydrogen or optionally substituted $C_{1-6}$ alkyl;
$R^{16}$ is hydrogen or optionally substituted $C_{1-6}$ alkyl;
$R^{17}$ is hydrogen or optionally substituted $C_{1-6}$ alkyl;
$R^{18}$ is hydrogen or optionally substituted $C_{1-6}$ alkyl;
n is a number from one to 1200;
p is a number from one to 1200;
$L^3$ is —C(O)—($C_6H_4$)—($CH_2$)$_e$— or —C(O)—($CH_2$)$_e$—; and
e is a number from one to 10.

In one aspect of the present application, there is provided a compound of the formula (XIII):

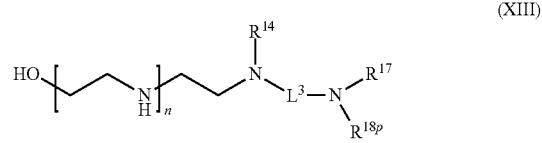

(XIII)

or a salt thereof, wherein
$R^{14}$ is hydrogen, optionally substituted $C_{1-6}$ alkyl, or

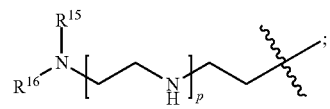

$R^{15}$ is hydrogen or optionally substituted $C_{1-6}$ alkyl;
$R^{16}$ is hydrogen or optionally substituted $C_{1-6}$ alkyl;
$R^{17}$ is hydrogen or optionally substituted $C_{1-6}$ alkyl;
$R^{18p}$ is a polypeptide, wherein the linkage between $R^{18p}$ and N is with an acyl donor glutamine tag from the polypeptide;
n is a number from one to 1200;
p is a number from one to 1200;
$L^3$ is —C(O)—($C_6H_4$)—($CH_2$)$_e$— or —C(O)—($CH_2$)$_e$—; and
e is a number from one to 10. In some embodiments, $R^{18p}$ is a targeting polypeptide, such as an Fc-containing polypeptide or a Fab-containing polypeptide, for example, an antibody. In some embodiments, $R^{18p}$ specifically binds to an intracellular molecule. In some embodiments, $R^{18p}$ specifically binds to an extracellular molecule. In some embodiments, $R^{18p}$ is a multispecific antibody, such as a multispecific antibody comprises a first binding domain that specifically binds to an extracellular molecule and a second binding domain and specifically binds to an intracellular molecule.

In one aspect of the present application, there is provided a complex comprising
a) a compound of the formula (XIII):

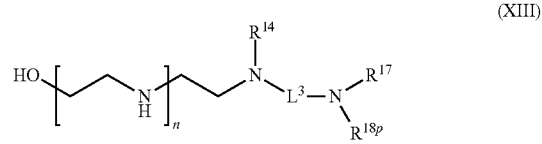

(XIII)

or a salt thereof, wherein
$R^{14}$ is hydrogen, optionally substituted $C_{1-6}$ alkyl, or

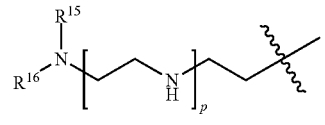

$R^{15}$ is hydrogen or optionally substituted $C_{1-6}$ alkyl;
$R^{16}$ is hydrogen or optionally substituted $C_{1-6}$ alkyl;
$R^{17}$ is hydrogen or optionally substituted $C_{1-6}$ alkyl;
$R^{18p}$ is a polypeptide, wherein the linkage between $R^{18p}$ and N is with an acyl donor glutamine tag from the polypeptide;
n is a number from one to 1200;
p is a number from one to 1200;
$L^3$ is —C(O)—(C$_6$H$_4$)—(CH$_2$)$_e$— or —C(O)—(CH$_2$)$_e$—; and
e is a number from one to 10; and b) a biologically active molecule. In some embodiments, $R^{18p}$ is a targeting polypeptide. In some embodiments, the biologically active molecule is non-covalently associated with the compound of formula (XIII). In some embodiments, the biologically active molecule is covalently associated with the compound of formula (XIII). In some embodiments, the biologically active molecule is a charged molecule. In some embodiments, the biologically active molecule is an oligonucleotide, DNA or RNA. In some embodiments, the biologically active molecule is a second polypeptide. In some embodiments, the complex further comprises a second biologically active molecule. In some embodiments, the biologically active molecule is a second polypeptide, and wherein the second polypeptide is conjugated to the second biologically active molecule.

In some embodiments according to any one of the compounds of the formula (XIII) described above, there is provided a method of preparing the compound, wherein the method comprises:
reacting a compound of formula (XII)

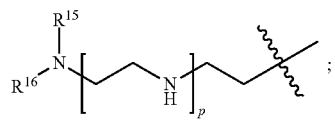

(XII)

or a salt thereof, wherein
$R^{14}$ is hydrogen, optionally substituted $C_{1-6}$ alkyl, or

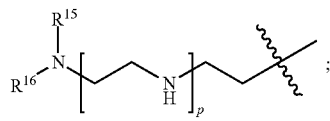

$R^{15}$ is hydrogen or optionally substituted $C_{1-6}$ alkyl;
$R^{16}$ is hydrogen or optionally substituted $C_{1-6}$ alkyl;
$R^{17}$ is hydrogen or optionally substituted $C_{1-6}$ alkyl;
$R^{18}$ is hydrogen or optionally substituted $C_{1-6}$ alkyl;
n is a number from one to 1200;
p is a number from one to 1200;
$L^3$ is —C(O)—(C$_6$H$_4$)—(CH$_2$)$_e$— or —C(O)—(CH$_2$)$_e$—; and
e is a number from one to 10;
with a polypeptide having an acyl donor glutamine tag in the presence of transglutaminase;
wherein the $C_{1-6}$ alkyl group of $R^{17}$ and $R^{18}$ are removed before contact with the polypeptide if $C_{1-6}$ alkyl are present in $R^{17}$ and $R^{18}$.

In some embodiments according to any one of the complexes comprising the compound of the formula (XIII) described above, there is provided a method of preparing the complex, wherein the method comprises:
contacting a compound of formula (XIII)

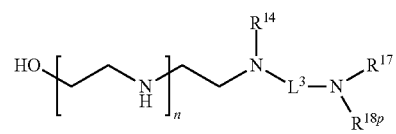

(XIII)

or a salt thereof, wherein
$R^{14}$ is hydrogen, optionally substituted $C_{1-6}$ alkyl, or

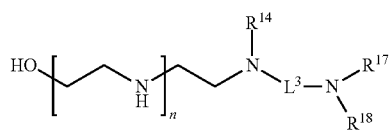

$R^{15}$ is hydrogen or optionally substituted $C_{1-6}$ alkyl;
$R^{16}$ is hydrogen or optionally substituted $C_{1-6}$ alkyl;
$R^{17}$ is hydrogen or optionally substituted $C_{1-6}$ alkyl;
$R^{18p}$ is a polypeptide, wherein the linkage between $R^{18p}$ and N is with an acyl donor glutamine tag from the polypeptide;
n is a number from one to 1200;
p is a number from one to 1200;
$L^3$ is —C(O)—(C$_6$H$_4$)—(CH$_2$)$_e$— or —C(O)—(CH$_2$)$_e$—; and
e is a number from one to 10;
with a biologically active molecule.

Also provided are compositions, kits, and articles of manufacture comprising any one of the compounds or the complexes described above, or a salt thereof. In some embodiments, there is provided a pharmaceutical composition comprising any one of the compounds or the complexes described above, or a salt thereof, and a pharmaceutically acceptable carrier.

Further provided are methods of delivering a biologically active molecule to the cytoplasm of a cell, comprising contacting the cell with an effective amount of any one of the compounds or complexes described above, or a pharmaceutically acceptable salt thereof. In some embodiments, the polypeptide of the compound or the complex is a targeting polypeptide that specifically binds to a cell surface molecule expressed by the cell. In some embodiments, the biologically active molecule is a charged molecule. In some embodiments, the biologically active molecule comprises an oligonucleotide, DNA, or RNA. In some embodiments, the biologically active molecule comprises a second polypeptide. In some embodiments, the biologically active molecule comprises a polypeptide conjugated to a second biologically active molecule. In some embodiments, the biologically active molecule comprises an antibody that specifically recognizes an intracellular molecule.

Further provided are methods of delivering an antibody that specifically recognizes an intracellular molecule to the cytoplasm of a cell, comprising contacting the cell with an effective amount of any of the compounds described above, or a pharmaceutically acceptable salt thereof, wherein the polypeptide comprises the antibody. In some embodiments, the polypeptide is a multispecific antibody comprising a first binding domain that specifically recognizes a cell surface molecule expressed by the cell and a second binding domain that specifically recognizes the intracellular molecule.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE DRAWINGS

FIG. 4 shows confocal microscopy images of A431 cells treated with Erb001B1. Nuclei are stained in blue. Erb001B1 is shown in red. Lysosomes are stained with an anti-Lamp1 antibody and shown in green. Yellow color indicates co-localization of Erb001B1 and lysosomes. FIG. 4A shows staining results of A431 cells grown in DMEM medium with serum for 48 hours followed by growth in DMEM medium without serum for 15 hours (high EGFR expression), treated with Erb001B1 for 5 minutes, washed three times with DMEM medium without serum, and incubated for 1 hour with DMEM medium without serum. FIG. 4B shows staining results of A431 cells grown in DMEM medium with serum for 48 hours followed by growth in DMEM medium without serum for 15 hours (high EGFR expression), treated with Erb001B1 for 5 minutes, washed three times with DMEM medium without serum, and incubated for 4 hours with DMEM medium without serum.

FIG. 5 shows confocal microscopy images of A431 cells treated with the Erb001B1-RF8 conjugate. Nuclei are stained in blue. Erb001B1-RF8 is shown in red. Lysosomes are stained with an anti-Lamp1 antibody and shown in green. Yellow color indicates co-localization of Erb001B1-RF8 and lysosomes. FIG. 5A shows staining results of A431 cells grown in DMEM medium with serum for 48 hours followed by growth in DMEM medium without serum for 15 hours (high EGFR expression), treated with Erb001B1-RF8 for 5 minutes, washed three times with DMEM medium without serum, and incubated for 1 hour with DMEM medium without serum. FIG. 5B shows staining results of A431 cells grown in DMEM medium with serum for 48 hours followed by growth in DMEM medium without serum for 15 hours (high EGFR expression), treated with Erb001B1-RF8 for 5 minutes, washed three times with DMEM medium without serum, and incubated for 4 hours with DMEM medium without serum.

FIG. 7 shows confocal microscopy images of A431 cells treated with 6-FAM-oligonucleotide in complex with the Erb001B1-RF8 conjugate. Cell masks (i.e. membranes) are shown in magenta. Lysosomes are stained with LYSOTRACKER RED® (Life Technologies), and shown in red. 6-FAM oligonucleotide is shown in green. Nucleic are stained with Hoescht 33342 and shown in blue. Left figure depicts three-dimensional reconstruction figures of cells based on Z-stack images with cell membranes shown. Middle figure depicts two-dimensional images of cells with cell membranes removed. Right figure depicts close-up side view of cells demonstrating co-localization of the 6-FAM-oligonucleotide and cellular structures (e.g., nuclei and/or lysosomes).

DETAILED DESCRIPTION OF THE INVENTION

I. Definitions

Figure 1:
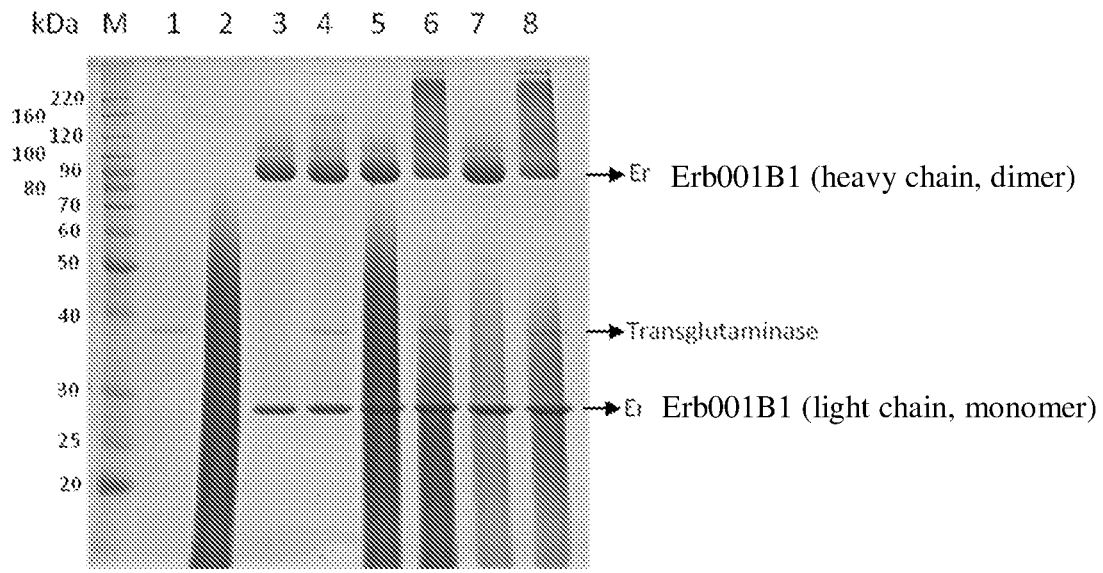
FIG. 1 shows an SDS-PAGE gel of transglutamination reaction samples comprising Erb001B1, PEI (i.e., RF8), or transglutaminase (TG). Compositions of the samples are described in the legend below the gel picture.

The following terms have the following meanings unless otherwise indicated. Any undefined terms have their art recognized meanings.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in P. G. M. Wuts and T. W. Greene, "Greene's Protective Groups in Organic Synthesis Fourth Edition," John Wiley and Sons, New York, N.Y., 2007, which is hereby incorporated by reference in its entirety, and Harrison et al., Compendium of Synthetic Organic Methods, Vols. 1-8, 1971-1996, John Wiley & Sons, NY. An amino-protecting group means a substituent commonly employed to block or protect a nitrogen functionality while carrying out a reaction with other functional groups on a compound.

The term "solid phase chemistry" refers to the conduct of chemical reactions where one component of the reaction is covalently bonded to a polymeric material (solid support as defined below). Reaction methods for performing chemistry on solid phase have become more widely known and established outside the traditional fields of peptide and oligonucleotide chemistry.

The term "solid phase resin" refers to a mechanically and chemically stable polymeric matrix utilized to conduct solid phase chemistry. The solid phase resin may be a resin generally used in solid phase synthesis, and for example, 2-chlorotrityl chloride resin functionalized with chlorine, Amino-PEGA resin functionalized with an amino group, NovaSyn TGT alcohol resin having a hydroxyl group, Wang resin, and HMPA-PEGA resin etc. can be employed.

The term "Fc-containing polypeptide" as used herein refers to a polypeptide (e.g., an antibody or an immunoadhesin) comprising the carboxyl terminal polypeptide sequences of an immunoglobulin heavy chain. The Fc-containing polypeptide may comprise native or variant Fc regions (i.e., sequences). The Fc region of an immunoglobulin generally comprises two constant domains, a CH2 domain and a CH3 domain, and optionally comprises a CH4 domain. An Fc-containing polypeptide may comprise part or all of a wild-type hinge sequence (generally at its amino terminus). An Fc-containing polypeptide may also be a dimer. An Fc-containing polypeptide may be obtained or derived from any suitable immunoglobulin, such as from at least one of the various IgG1, IgG2, IgG3, or IgG4 subtypes, or from IgA, IgE, IgD or IgM.

Although the boundaries of the Fc region of an immunoglobulin heavy chain might vary, for example, the human IgG heavy chain Fc region is usually defined to stretch from an amino acid residue at position Glu216, or from Ala231, to the carboxyl-terminus thereof. The numbering of the residues in the Fc region is that of the EU index as in Kabat et al., Sequences of Proteins of Immunological Interest, 5th Ed. Public Health Service, National Institutes of Health, Bethesda, Md., 1991.

An Fc-containing polypeptide may be an Fc-containing fusion polypeptide, wherein one or more polypeptides is operably linked to an Fc-containing polypeptide. An Fc fusion combines the Fc polypeptide of an immunoglobulin with a fusion partner, which in general may be any protein, polypeptide, or small molecule. Virtually any protein or small molecule may be linked to the Fc region to generate an Fc-containing fusion polypeptide. Fc-containing fusion partners may include, but are not limited to, the target-binding region of a receptor, an adhesion molecule, a ligand, an enzyme, a cytokine, a chemokine, or some other protein or protein domain.

The term "glutamine acceptor", "glutamine amine acceptor", "acyl donor glutamine-containing tag", "glutamine tag," "Q-containing tag", or "Q-tag" as used herein refers to a polypeptide or a protein containing one or more Gln residue(s) that acts as a transglutaminase amine acceptor.

As used herein, the term "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, unless otherwise indicated by context, the term is intended to be used in the broadest sense to encompass not only intact polyclonal or monoclonal antibodies, but also fragments thereof (such as Fab, Fab', F(ab')$_2$, Fv), single chain (ScFv) and domain antibodies, including shark and camelid antibodies), and fusion proteins comprising an antibody portion, multivalent antibodies, multispecific antibodies (e.g., bispecific antibodies so long as they exhibit the desired biological activity) and antibody fragments as described herein, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. The immunoglobulin can be from any species, including, but not limited to, human, murine, and rabbit.

The term "full length antibody" refers to an antibody in its substantially intact form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, CH1, CH2, and CH3. In some mammals, for example in camels and llamas, IgG antibodies may consist of only two heavy chains, each heavy chain comprising a variable domain attached to the Fc region. A full length antibody can be a native sequence antibody, or an antibody with a recombinantly engineered sequence.

The term "Fab-containing polypeptide" as used herein refers to a polypeptide comprising a Fab fragment, Fab' fragment, or F(ab')$_2$ fragment. A Fab-containing polypeptide may comprise part or all of a wild-type hinge sequence (generally at its carboxyl terminus). A Fab-containing polypeptide may be obtained or derived from any suitable immunoglobulin, such as from at least one of the various IgG1, IgG2, IgG3, or IgG4 subtypes, or from IgA, IgE, IgD or IgM. A Fab-containing polypeptide may be a Fab-containing fusion polypeptide, wherein one or more polypeptides is operably linked to a Fab-containing polypeptide. A Fab fusion combines the Fab polypeptide of an immunoglobulin with a fusion partner, which in general may be any protein, polypeptide, or small molecule. Virtually any protein or small molecule may be linked to the Fab polypeptide to generate a Fab-containing fusion polypeptide. Fab-containing fusion partners may include, but are not limited to, the target-binding region of a receptor, an adhesion molecule, a ligand, an enzyme, a cytokine, a chemokine, or some other protein or protein domain.

A "Fab fragment" is comprised of one light chain and the CH1 and variable regions of one heavy chain. The heavy chain of a Fab molecule cannot form a disulfide bond with another heavy chain molecule.

A "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the CH1 and CH2 domains, such that an interchain disulfide bond is formed between the two heavy chains. A F(ab')$_2$ fragment thus is composed of two Fab' fragments that are held together by a disulfide bond between the two heavy chains.

"Antibody fragments" (including "antigen-binding fragments") as used herein comprise only a portion of an intact antibody, wherein the portion preferably retains at least one, preferably most or all, of the functions normally associated with that portion when present in an intact antibody.

A "multispecific antibody" is one that targets more than one antigen or epitope. A "bispecific," "dual-specific," or "bifunctional" antibody is a hybrid antibody having two different antigen binding sites. Bispecific antibodies are a species of multispecific antibody and may be produced by a variety of methods including, but not limited to, fusion of hybridomas or linking of Fab' fragments. See, e.g., Songsivilai & Lachmann (1990), Clin. Exp. Immunol. 79:315-321; and Kostelny et al. (1992), J. Immunol. 148: 1547-1553. The two binding sites of a bispecific antibody will bind to two different epitopes, which may reside on the same or different protein targets.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, Nature, 256:495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., Proc. Natl. Acad. Sci. USA 81:6851-6855 (1984)). Chimeric antibodies include PRIMATTZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et ah, Nature 321:522-525 (1986); Riechmann et al, Nature 332:323-329 (1988); and Presta, Curr. Op. Struct. Biol. 2:593-596 (1992). See also, e.g., Vaswani and Hamilton, Ann. Allergy, Asthma & Immunol. 1: 105-115 (1998); Harris, Biochem. Soc. Transactions 23: 1035-1038 (1995); Hurle and Gross, Curr. Op. Biotech. 5:428-433 (1994); and U.S. Pat. Nos. 6,982,321 and 7,087, 409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol, 227: 381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et ah, J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et ah, Proc. Natl. Acad. Sci. USA, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996).

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

As used herein, the term "immunoadhesin" designates antibody-like or immunoglobulin-like molecules which combine the "binding domain" of a heterologous protein (an "adhesin", e.g., a receptor, ligand or enzyme) with the effector component of immunoglobulin constant domains (i.e., Fc domain). Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as IgG1, IgG2, IgG3, or IgG4 subtypes, IgA, IgE, IgD or IgM, or variants thereof.

The "hinge region," "hinge sequence," and variation thereof, as used herein, includes the meaning known in the art, which is illustrated, for example, Janeway et al., ImmunoBiology: the immune system in health and disease, (Elsevier Science Ltd., NY) (4th ed., 1999); Bloom et al., Protein Science (1997), 6:407-415; Humphreys et al., J. Immunol. Methods (1997), 209: 193-202.

As used herein, the term "specifically recognizes" or "specifically binds" refers to measurable and reproducible interactions such as attraction or binding between a target and an antibody (or a molecule or a moiety), that is determinative of the presence of the target in the presence of a heterogeneous population of molecules including biological molecules. For example, an antibody that specifically or preferentially binds to an epitope is an antibody that binds this epitope with greater affinity, avidity, more readily, and/or with greater duration than it binds to other epitopes of the target or non-target epitopes. It is also understood that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3 M^{-1}$ or $10^4 M^{-1}$, sometimes about $10^5 M^{-1}$ or $10^6 M^{-1}$, in other instances about $10^6 M^{-1}$ or $10^7 M^{-1}$, about $10^8 M^{-1}$ to $10^9 M^{-1}$, or about $10^{10} M^{-1}$ to $10^{11} M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, an "effective amount" of compound, conjugate, complex, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount can be administered in one or more administrations. For purposes of the present disclosure, an effective amount of compound, conjugate, complex or pharmaceutical composition is an amount sufficient to achieve an effect in a cell (such as gene expression, gene silencing, target inhibition, cytotoxicity, etc.), or to accomplish prophylactic or therapeutic treatment either directly or indirectly. As is understood in the clinical context, an effective amount of a compound, conjugate, complex, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during or after administration of the other treatment modality to the individual.

As used herein, "treatment" or "treating" is an approach for obtaining beneficial or desired results including and preferably clinical results. For purposes of the present disclosure, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, preventing or delaying the recurrence of the disease, reducing recurrence rate of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival of individuals.

An "individual" or a "subject" is a mammal, more preferably a human. Mammals also include, but are not limited to, farm animals, sport animals, pets (such as cats, dogs, horses), primates, mice and rats.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

Reference to "about" a value or parameter herein includes (and describes) embodiments that are directed to that value or parameter per se. For example, description referring to "about X" includes description of "X."

It is understood that aspect and variations of the invention described herein include "consisting" and/or "consisting essentially of" aspects and variations.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, 4th edition, New York: Oxford University Press, 2002, pp. 360-361, 1084-1085; Smith and March, March's Advanced Organic Chemistry: Reactions, Mechanisms, and Structure, 5th edition, Wiley-Interscience, 2001; Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual˜ Cold Spring Harbor Laboratory Press, Cold Spring Harbor, N.Y. (1998); and Coligan et al., Short Protocols in Protein Science, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, molecular biology, biochemistry, immunology, analytical chemistry, synthetic organic chemistry, and medicinal and pharmaceutical chemistry described herein are those well-known and commonly used in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

II. PEI Compounds and Conjugates

The present disclosure relates to modifications of polypeptides, such as antibodies, which change the behavior of the polypeptide. In certain embodiments, the modifications increase the interaction of the polypeptide with the cell surface and allow it to internalize. In other embodiments, the polypeptides are targeting polypeptides, including, but not limited to polypeptides such as ligands and antibodies that specifically bind to a cell surface molecule, and the modifications to the polypeptide thereby allow specific internalization of the polypeptide within target cells that express the cell surface molecule. In still other embodiments, the polypeptides are targeting polypeptides, including, but not limited to polypeptides such as ligands and antibodies that specifically bind to a cell surface molecule and internalize and the modifications change the rate of internalization and/or the intracellular distribution of the polypeptide, such as allowing access to a cytoplasm compartment.

The modification of the polypeptides (such as targeting polypeptide, for example, antibody) is based on the use of PEI (polyethylenimine or poly(iminoethylene)) that is covalently conjugated to the polypeptide. The PEI (such as a linear PEI) molecule contains an engineered linker comprising a functional group that can be linked to a specific site in the polypeptide via a chemical or enzymatic reaction. The PEI-polypeptide conjugate can further covalently or non-covalently associate with one or more biologically active molecule, such as a DNA, RNA, RNAi, peptide, protein, or small molecule, to form a PEI-polypeptide complex. The polypeptide specifically targets a cell, PEI promotes or aids internalization of the PEI-polypeptide conjugate or complex by a cell and potentially changes the way the PEI-polypeptide conjugate is distributed within the cell. For example, instead of following the typical metabolic fate of endocytosed macromolecules, the PEI-polypeptide conjugate or complex is rapidly released to the cytoplasm.

The mechanism of release from endosomes and/or lysosomes is based on the properties of PEI and other molecules described herein. These molecules have weak bases that are neutrally charged at physiological pH in the extracellular space, but become strongly positively charged at acidic or low pH, such as in an acidified endosome following internalization of the PEI-polypeptide complex. Without being bound by any theory or hypothesis, the strongly charged PEI of the PEI-polypeptide complex creates a charged gradient across the endosomal membrane, which can burst the endosome and release the contents of the endosome into the cytoplasm. Inside the cytoplasm, for example, an intracellular antibody comprised in a PEI-polypeptide complex can be exposed to its intracellular antigen, which would otherwise be unreachable by the antibody. Also, the PEI-polypeptide complex may unload any biologically active molecule associated with PEI, such as DNA or RNA, or any biologically active molecule covalently linked to the polypeptide, such as a small molecule drug.

The present disclosure relates to PEI compounds comprising a linker and PEI-polypeptide conjugates. The present disclosure provides compounds of any of Formulae (I)-(XIII), which are discussed below.

Formulae (I)-(IV)

The present disclosure provides a compound of Formula (I):

or a salt thereof, wherein

PEI is polyethylenimine, which terminates with —OH or —NHR, wherein R is hydrogen or $C_{1-6}$ alkyl;

$L^{10}$ is a linker; and

FG is a functional group that is reactive in a thiol modification reaction, a click reaction, or an enzymatic reaction;

wherein the $L^{10}$ can be connected to PEI at the terminus or in an interior repeat unit of PEI.

In some embodiments, $L^{10}$ is connected to PEI at a hydroxy terminus, and the PEI moiety of Formula (I) terminates with —NHR where R is hydrogen or $C_{1-6}$ alkyl. In some embodiments, $L^{10}$ is connected to PEI at an amino terminus, and the PEI moiety of Formula (I) terminates with —OH. In some embodiments, $L^{10}$ is connected to PEI at an interior (or internal) amino group, and the PEI moiety of Formula (I) terminates with —OH and —NHR where R is hydrogen or $C_{1-6}$ alkyl.

In some embodiments of Formula (I), PEI has a molecular weight of about 2500 to about 50000. In some embodiments, PEI has a molecular weight of about 5000 to about 15000.

In some embodiments, PEI has a molecular weight of about 1 to about 2500. In some embodiments, PEI has a molecular weight of about any of 1-500, 500-1000, 1000-1500, 1500-2000, and 2000-2500.

In some embodiments, PEI has a molecular weight of about any of 1-2500, 2500-3000, 3000-3500, 3500-4000, 4000-4500, 4500-5000, 5000-5500, 5500-6000, 6000-6500, 6500-7000, 7000-7500, 7500-8000, 8000-8500, 8500-9000, 9000-9500, 9500-10000, 10000-11000, 11000-12000, 12000-13000, 13000-14000, 14000-15000, 15000-16000, 16000-17000, 17000-18000, 18000-19000, 19000-20000, 21000-22000, 22000-23000, 23000-24000, 24000-25000, 25000-26000, 26000-27000, 27000-28000, 28000-29000, 29000-30000, 30000-31000, 31000-32000, 32000-33000, 33000-34000, 34000-35000, 35000-36000, 36000-37000, 37000-38000, 38000-39000, 39000-40000, 40000-41000, 41000-42000, 42000-43000, 43000-44000, 44000-45000, 45000-46000, 46000-47000, 47000-48000, 48000-49000, and 49000-50000.

In some embodiments, PEI has a molecular weight of about 2500, 5000, 7500, 10000, 12500, 15000, 17500, 20000, 22250, 25000, 27500, 30000, 32500, 35000, 37500, 40000, 42500, 45000, 47500, or 50000.

The present disclosure provides a compound of Formula (II):

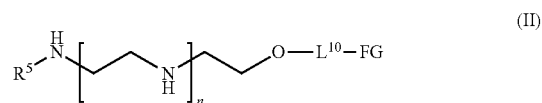

or a salt thereof, wherein $R^5$ is hydrogen or optionally substituted $C_{1-6}$ alkyl;

n is a number from one to 1200;

$L^{10}$ is a linker; and

FG is a functional group that is reactive in a thiol modification reaction, a click reaction, or an enzymatic reaction.

In some embodiments of Formula (II), n is a number from one to 50, 100, 200, 300, 400, 500, 600, 700, 800, 900, 1000, 1100, or 1200. In some embodiments, n is a number from 50 to 100, 200, 300, 400, 500, 600, 700, 800, 900, 1000, 1100, or 1200. In some embodiments, n is a number from 50 to 1200. In some embodiments, n is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (II), $R^5$ is hydrogen. In some embodiments, $R^5$ is an optionally substituted $C_{1-6}$ alkyl. In some embodiments, $R^5$ is methyl.

The present disclosure provides a compound of Formula (III):

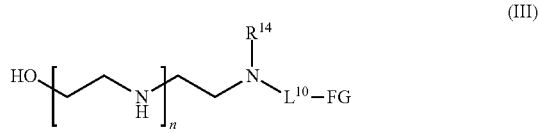

(III)

or a salt thereof, wherein
n is a number from one to 1200;
$L^{10}$ is a linker;
FG is a functional group that is reactive in a thiol modification reaction, a click reaction, or an enzymatic reaction;
$R^{14}$ is hydrogen, optionally substituted $C_{1-6}$ alkyl, or

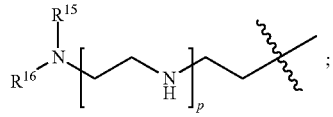

wherein
$R^{15}$ is hydrogen or optionally substituted $C_{1-6}$ alkyl;
$R^{16}$ is hydrogen or optionally substituted $C_{1-6}$ alkyl; and
p is a number from one to 1200.

In some embodiments of Formula (III), $R^{14}$ is hydrogen. In some embodiments, $R^{14}$ is optionally substituted $C_{1-6}$ alkyl. In some embodiments, $R^{14}$ is

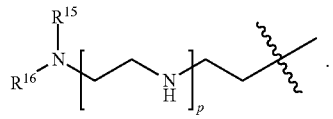

In some embodiments of Formula (III), $R^{15}$ is hydrogen. In some embodiments, $R^{15}$ is optionally substituted $C_{1-6}$ alkyl. In some embodiments, $R^{15}$ is methyl.

In some embodiments of Formula (III), $R^{16}$ is hydrogen. In some embodiments, $R^{16}$ is optionally substituted $C_{1-6}$ alkyl. In some embodiments, $R^{16}$ is methyl.

In some embodiments of Formula (III), n is a number from one to 50, 100, 200, 300, 400, 500, 600, 700, 800, 900, 1000, 1100, or 1200. In some embodiments, n is a number from 50 to 100, 200, 300, 400, 500, 600, 700, 800, 900, 1000, 1100, or 1200. In some embodiments, n is a number from 50 to 1200. In some embodiments, n is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (III), p is a number from one to 50, 100, 200, 300, 400, 500, 600, 700, 800, 900, 1000, 1100, or 1200. In some embodiments, p is a number from 50 to 100, 200, 300, 400, 500, 600, 700, 800, 900, 1000, 1100, or 1200. In some embodiments, p is a number from 50 to 1200. In some embodiments, p is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (III), n+p is a number from one to 50, 100, 200, 300, 400, 500, 600, 700, 800, 900, 1000, 1100, or 1200. In some embodiments, n+p is a number from 50 to 100, 200, 300, 400, 500, 600, 700, 800, 900, 1000, 1100, or 1200. In some embodiments, n+p is a number from 50 to 1200. In some embodiments, n+p is 50, 100, 150, 200, 250, 300, 350, 400, 450, 500, 550, 600, 650, 700, 750, 800, 850, 900, 950, 1000, 1050, 1100, 1150, or 1200.

In Formulae (I)-(III), FG is a functional group that is reactive in a thiol modification reaction, a click reaction, or an enzymatic reaction. A variety of chemistries are contemplated and described in more detail below.

For use in a thiol modification reaction, a functional group in any of Formulae (I)-(III) can react with a thiol group. Thiol groups can be found, for example, in peptides or proteins in the side chain of cysteine amino acids. Pairs of cysteine thiol groups are often linked by disulfide bonds (—S—S—) within or between polypeptide chains as the basis of native tertiary or quaternary protein structure. Typically, free or reduced sulfhydryl groups (—SH) [rather than sulfur atoms in disulfide bonds] are available for reaction with thio-reactive compounds.

Examples of thiol-reactive chemical groups include haloacetyls, maleimides, aziridines, acryloyls, arylating agents, vinylsulfones, pyridyl disulfides, thiols, and disulfide reducing agents. Most of these groups react with sulfhydryls by either alkylation (usually the formation of a thioether bond) or disulfide exchange (formation of a disulfide bond). In some embodiments of Formulae (I)-(III), FG is acryloyl. In some embodiments of Formulae (I)-(III), FG is

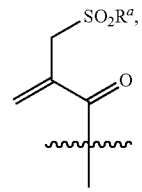

wherein $R^a$ is alkyl. In some embodiments of Formulae (I)-(III), FG is

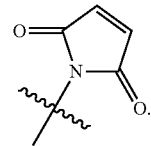 [SMILES: *N1C(=O)C=CC1=O]

In some embodiments, a functional group on any of Formulae (I)-(III) is reactive in a click reaction. In general, click reactions are a group of high-yield chemical reactions that were collectively termed "click chemistry" reactions by Sharpless in a review of several small molecule click chemistry reactions. (Kolb, H. C.; Finn, M. G.; Sharpless, K. B. Angew. Chem., Int. Ed. 40, 2004-2021 (2001), the disclosure of which is incorporated herein by reference.) As used herein, a "click reaction" refers to a reliable, high-yield, and selective reaction having a thermodynamic driving force of greater than or equal to 20 kcal/mol. Click chemistry reactions may, for example, be used for synthesis of molecules comprising heteroatom links. One of the most frequently used click chemistry reactions involves cycloaddition between azides and alkynyl/alkynes to form the linkage comprising a substituted or unsubstituted 1,2,3-triazole. Certain click reactions may, for example, be performed in alcohol/water mixtures or in the absence of solvents and the products can be isolated in substantially quantitative yield. Click reactions with application to pharmaceutical sciences are discussed in a review. (Hein et al., Pharm. Res. 2008 October; 25 (10): 2216-2230), the disclosure of which is incorporated herein by reference.)

Examples of suitable click reactions for use herein include, but are not limited to, Staudinger ligation, azide-alkyne cycloaddition (either strain promoted or copper(I) catalyzed), reaction of tetrazine with trans-cyclooctenes, disulfide linking reactions, thiolene reactions, hydrazine-aldehyde reactions, hydrazine-ketone reactions, hydroxyl amine-aldehyde reactions, hydroxyl amine-ketone reactions and Diels-Alder reactions. In such click reactions, one of the functional groups of the click reaction is on a compound of any of formulae (I)-(III) and the other of the functional groups of the click reaction is on a molecule to be reacted with the compound of any of formulae (I)-(III).

In some embodiments of Formulae (I)-(III), FG is selected from azido, alkynyl, alkenyl, oxiranyl, thiiranyl, aziridinyl, aldehyde, acyl, alkoxyamino, hydrazine, and amino.

In some embodiments of Formulae (I)-(III), FG is azido or dibenzocyclooctyl (DBCO),

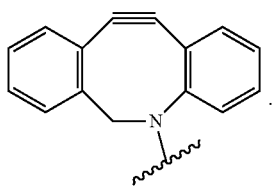 [SMILES: *N1Cc2ccccc2C#Cc2ccccc21]

With azido and DBCO groups, dibenzocyclooctyl (DBCO) copper-free click chemistry can be used. An example of DBCO copper-free click chemistry is shown below.

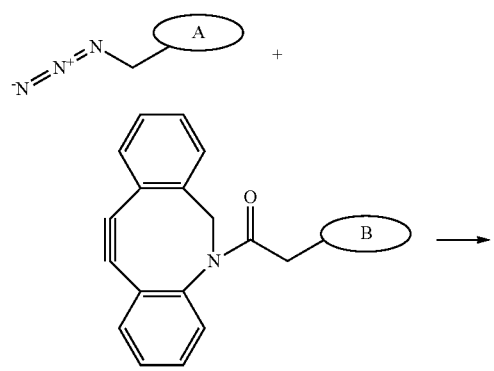

In some embodiments of Formulae (I)-(III), FG is azido or alkynyl. With azido and alkynyl groups, click chemistry can be used. In some embodiments, the azido-alkynyl click chemistry is catalyzed by copper. Azido-alkynyl click chemistry can be performed with a variety of temperatures, solvents, and pH conditions. An example of azido-alkynyl click chemistry is shown below.

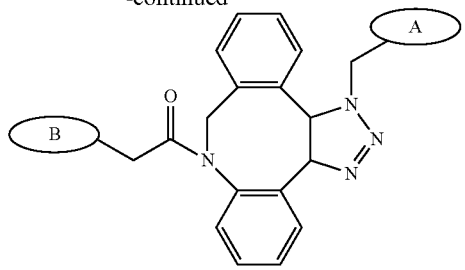

In some embodiments of Formulae (I)-(III), FG is alkoxyamino, $H_2N-O-$. An alkoxyamino group is useful, for example, for reaction with aldehydes, such as in a click reaction.

In some embodiments, a functional group on any of Formulae (I)-(III) is reactive in an enzymatic reaction. An enzymatic reaction can utilize an enzyme's property of group specificity in which the enzyme will act on molecules that have specific functional groups.

In some embodiments of Formulae (I)-(III), FG is Gly-Gly-Gly-. The Gly-Gly-Gly-motif is useful for a sortase conjugation reaction.

In Formulae (I)-(III), $L^{10}$ is a linker. As used herein a "linker" is a bond, molecule, or group of molecules that binds two separate entities to one another. Linkers may provide for optimal spacing of the two entities. In some embodiments, the term "linker" refers to any agent or molecule that bridges PEI to a functional group.

In some embodiments of Formulae (I)-(III), $L^{10}$ is $-SiR^1R^2-(CH_2)_a-$, $-SiR^1R^2-(CH_2)_a-NH-C(O)-NH-(CH_2)_b-$, $-SiR^1R^2-(CH_2)_a-C(O)-NH-(CH_2)_b-$, or $-SiR^1R^2-(CH_2)_a-NH-C(O)-(CH_2)_b-$; wherein $R^1$ and $R^2$ are independently optionally substituted $C_{1-6}$ alkyl, optionally substituted aryl, or optionally substituted heteroaryl; a is a number from one to 20; and b is a number from one to 20.

In some embodiments of Formulae (I)-(III), $L^{10}$ is $-(C_6H_4)-(CH_2)_c-$, $-(C_6H_4)-NH-(CH_2)_c-$, $-(C_6H_4)-C(O)-NH-(CH_2)_c-$, $-(C_6H_4)-NH-(CH_2CH_2O)_d-CH_2CH_2-$, or $-(C_6H_4)-C(O)-NH-(CH_2CH_2O)_d-CH_2CH_2-$; wherein c is a number from one to 10; and d is a number from one to 10.

In some embodiments of Formulae (I)-(III), $L^{10}$ is $-C(O)-(C_6H_4)-(CH_2)_e-$ or $-C(O)-(CH_2)_e-$; and e is a number from one to 10.

The present disclosure provides a compound of Formula (IV):

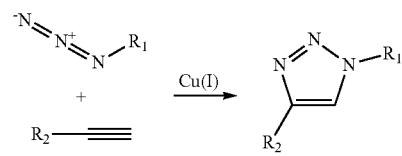

(IV)

or a salt thereof, wherein

PEI is polyethylenimine, which terminates with —OH or —NHR, wherein R is hydrogen or $C_{1-6}$ alkyl;

$L^{10}$ is a linker;

q is a number from one to 100; and $R^{20}$ is a polypeptide, wherein the $L^{10}$ can be connected to PEI at the terminus or in an interior repeat unit of PEI.

In some embodiments of Formula (IV), $L^{10}$ is connected to PEI at a hydroxy terminus, and the PEI moiety terminates with —NHR where R is hydrogen or $C_{1-6}$ alkyl. In some embodiments of Formula (IV), $L^{10}$ is connected to PEI at an amino terminus, and the PEI moiety terminates with —OH. In some embodiments of Formula (IV), L10 is connected to PEI at an interior (or internal) amino group, and the PEI moiety terminates with —OH and —NHR where R is hydrogen or $C_{1-6}$ alkyl.

In some embodiments of Formula (IV), PEI has a molecular weight of about 2500 to about 50000. In some embodiments, PEI has a molecular weight of about 5000 to about 15000.

In some embodiments, PEI has a molecular weight of about 1 to about 2500. In some embodiments, PEI has a molecular weight of about any of 1-500, 500-1000, 1000-1500, 1500-2000, and 2000-2500.

In some embodiments, PEI has a molecular weight of about any of 1-2500, 2500-3000, 3000-3500, 3500-4000, 4000-4500, 4500-5000, 5000-5500, 5500-6000, 6000-6500, 6500-7000, 7000-7500, 7500-8000, 8000-8500, 8500-9000, 9000-9500, 9500-10000, 10000-11000, 11000-12000, 12000-13000, 13000-14000, 14000-15000, 15000-16000, 16000-17000, 17000-18000, 18000-19000, 19000-20000, 21000-22000, 22000-23000, 23000-24000, 24000-25000, 25000-26000, 26000-27000, 27000-28000, 28000-29000, 29000-30000, 30000-31000, 31000-32000, 32000-33000, 33000-34000, 34000-35000, 35000-36000, 36000-37000, 37000-38000, 38000-39000, 39000-40000, 40000-41000, 41000-42000, 42000-43000, 43000-44000, 44000-45000, 45000-46000, 46000-47000, 47000-48000, 48000-49000, and 49000-50000.

In some embodiments, PEI has a molecular weight of about 2500, 5000, 7500, 10000, 12500, 15000, 17500, 20000, 22250, 25000, 27500, 30000, 32500, 35000, 37500, 40000, 42500, 45000, 47500, or 50000.

In Formula (IV), $L^{10}$ is a linker. As used herein a "linker" is a bond, molecule, or group of molecules that binds two separate entities to one another. Linkers may provide for optimal spacing of the two entities. In some embodiments, the term "linker" refers to any agent or molecule that bridges PEI to a functional group.

In some embodiments of Formula (IV), $L^{10}$ is —$SiR^1R^2$—$(CH_2)_a$—, —$SiR^1R^2$—$(CH_2)_a$—NH—C(O)—NH—$(CH_2)_b$—, —$SiR^1R^2$—$(CH_2)_a$—C(O)—NH—$(CH_2)_b$—, or —$SiR^1R^2$—$(CH_2)_a$—NH—C(O)—$(CH_2)_b$—; wherein $R^1$ and $R^2$ are independently optionally substituted $C_{1-6}$ alkyl, optionally substituted aryl, or optionally substituted heteroaryl; a is a number from one to 20; and b is a number from one to 20.

In some embodiments of Formula (IV), $L^{10}$ is —$(C_6H_4)$—$(CH_2)_c$—, —$(C_6H_4)$—NH—$(CH_2)_c$—, —$(C_6H_4)$—C(O)—NH—$(CH_2)_c$—, —$(C_6H_4)$—NH—$(CH_2CH_2O)_d$—$CH_2CH_2$—, or —$(C_6H_4)$—C(O)—NH—$(CH_2CH_2O)_d$—$CH_2CH_2$—; wherein c is a number from one to 10; and d is a number from one to 10.

In some embodiments of Formula (IV), $L^{10}$ is —C(O)—$(C_6H_4)$—$(CH_2)_e$— or —C(O)—$(CH_2)_e$—; and c is a number from one to 10.

In some embodiments of Formula (IV), q is one. In some embodiments, q is a number from one to 5. In some embodiments, q is a number from one to 10. In some embodiments, q is a number from one to 5, 10, 20, 30, 40, 50, 60, 70, 80, 90, or 100.

In some embodiments of Formula (IV), the linkage between $R^{20}$ and $L^{10}$ is formed via a thiol modification reaction, a click reaction, or an enzymatic reaction. In some embodiments of Formula (IV), the linkage between $R^{20}$ and $L^{10}$ is formed via a thiol modification reaction. In some embodiments of Formula (IV), the linkage between $R^{20}$ and $L^{10}$ is formed via a click reaction. In some embodiments of Formula (IV), the linkage between $R^{20}$ and $L^{10}$ is formed via an enzymatic reaction.

In Formula (IV), $R^{20}$ is a polypeptide. In some embodiments, $R^{20}$ is a non-targeting polypeptide. In some embodiments, $R^{20}$ is a targeting polypeptide. In some embodiments, $R^{20}$ is an Fc-containing polypeptide or a Fab-containing polypeptide. In some embodiments, $R^{20}$ is an antibody. In some embodiments, $R^{20}$ specifically binds to an intracellular molecule.

In some embodiments, $R^{20}$ is a polypeptide and $L^{10}$ comprises a primary amino group and the linkage between $R^{20}$ and $L^{10}$ is with an acyl donor glutamine tag from the polypeptide of $R^{20}$ and the primary amino group of $L^{10}$.

Formulae (V)-(VII)

The present disclosure provides a compound of formula (V):

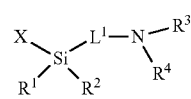

(V)

or a salt thereof, wherein

X is a leaving group selected from the group consisting of halogen and —$OSO_2R^x$, wherein $R^x$ is an optionally substituted $C_{1-6}$ alkyl, an optionally substituted aryl, or an optionally substituted heteroaryl;

$R^1$ and $R^2$ are independently optionally substituted $C_{1-6}$ alkyl, optionally substituted aryl, or optionally substituted heteroaryl;

$R^3$ and $R^4$ are independently hydrogen, $C_{1-6}$ alkyl, or an amino protecting group;

$L^1$ is —$(CH_2)_a$—, —$(CH_2)_a$—NH—C(O)—NH—$(CH_2)_b$—, —$(CH_2)_a$—C(O)—NH—$(CH_2)_b$—, or —$(CH_2)_a$—NH—C(O)—$(CH_2)_b$—;

a is a number from one to 20; and b is a number from one to 20.

In some embodiments of Formula (V), X is a halogen, such as fluoro, chloro, bromo, or iodo. In some embodiments, X is chloro. In some embodiments, X is —$OSO_2R^x$. In some embodiments, $R^x$ is an optionally substituted $C_{1-6}$ alkyl. In some embodiments, $R^x$ is an optionally substituted aryl. In some embodiments, $R^x$ is an optionally substituted heteroaryl.

In some embodiments of Formula (V), $R^1$ is optionally substituted $C_{1-6}$ alkyl. In some embodiments, $R^1$ is methyl. In some embodiments, $R^1$ is optionally substituted aryl. In some embodiments, $R^1$ is optionally substituted heteroaryl.

In some embodiments of Formula (V), $R^2$ is optionally substituted $C_{1-6}$ alkyl. In some embodiments, $R^2$ is methyl. In some embodiments, $R^2$ is optionally substituted aryl. In some embodiments, $R^2$ is optionally substituted heteroaryl.

In some embodiments of Formula (V), $R^1$ and $R^2$ are $C_{1-6}$ alkyl. In some embodiments, $R^1$ and $R^2$ are methyl. In some embodiments, $R^1$ and $R^2$ are $C_{1-6}$ alkyl and X is halo. In some embodiments, $R^1$ and $R^2$ are methyl and X is chloro.

In some embodiments of Formula (V), $R^3$ is hydrogen. In some embodiments, $R^3$ is $C_{1-6}$ alkyl. In some embodiments, $R^3$ is an amino protecting group. Examples of suitable amino protecting groups include, but are not limited to t-butoxycarbonyl, trityl, benzyloxycarbonyl, 9-fluorenylmethoxycarbonyl, formyl, trimethylsilyl, t-butyldimethylsilyl, tert-allyloxycarbonyl (Alloc), 9-fluorenylmethyl (Fm, FMOC), methoxycarbonyl, ethoxycarbonyl, benzyl (Bn), 2,2,4,6,7-pentamethyldihydrobenzofuran-5-sulfonyl (Pbf), acetyl, benzoyl, $C_6H_5$—$SO_2$—, 4-$NO_2C_6H_4$—$SO_2$—, 2-$NO_2C_6H_4$—$SO_2$—, and 2,4-$(NO_2)_2C_6H_3$—$SO_2$—. In some embodiments, $R^3$ is FMOC.

In some embodiments of Formula (V), $R^4$ is hydrogen. In some embodiments, $R^4$ is $C_{1-6}$ alkyl. In some embodiments, $R^4$ is an amino protecting group. Examples of suitable amino protecting groups include, but are not limited to t-butoxycarbonyl, trityl, benzyloxycarbonyl, 9-fluorenylmethoxycarbonyl, formyl, trimethylsilyl, t-butyldimethylsilyl, tert-allyloxycarbonyl (Alloc), 9-fluorenylmethyl (Fm, FMOC), methoxycarbonyl, ethoxycarbonyl, benzyl (Bn), 2,2,4,6,7-pentamethyldihydrobenzofuran-5-sulfonyl (Pbf), acetyl, benzoyl, $C_6H_5$—$SO_2$—, 4-$NO_2C_6H_4$—$SO_2$—, 2-$NO_2C_6H_4$—$SO_2$—, and 2,4-$(NO_2)_2C_6H_3$—$SO_2$—. In some embodiments, $R^4$ is FMOC.

In some embodiments of Formula (V), $R^3$ is hydrogen and $R^4$ is an amino protecting group. In some embodiments, $R^3$ is hydrogen and $R^4$ is FMOC. In some embodiments, $R^3$ and $R^4$ are amino protecting groups.

In some embodiments of Formula (V), $L^1$ is —$(CH_2)_a$—. In some embodiments, $L^1$ is —$(CH_2)_a$—NH—C(O)—NH—$(CH_2)_b$—. In some embodiments, $L^1$ is —$(CH_2)_a$—C(O)—NH—$(CH_2)_b$—. In some embodiments, $L^1$ is —$(CH_2)_a$—NH—C(O)—$(CH_2)_b$—.

In some embodiments, $L^1$ is —$(CH_2)_a$—NH—C(O)—NH—$(CH_2)_b$—, wherein a is a number from one to 5 and b is a number from one to 10. In some embodiments, $L^1$ is —$(CH_2)_a$—NH—C(O)—NH—$(CH_2)_b$—, wherein a is a number from one to 5 and b is 2, 4, or 6. In some embodiments, $L^1$ is —$(CH_2)_a$—NH—C(O)—NH—$(CH_2)_b$—, wherein a is 3 and b is 2, 4, or 6.

In some embodiments of Formula (V), a is a number from one to 5, 10, or 15. In some embodiments, a is 1, 2, 3, 4, 5, 6, 7, 8, 9 or 10. In some embodiments, a is 11, 12, 13, 14, 15, 16, 17, 18, 19 or 20. In some embodiments, a is 1, 2, 3, 4, or 5. In some embodiments, a is 3.

In some embodiments of Formula (V), b is a number from one to 5, 10, or 15. In some embodiments, b is 1, 2, 3, 4, 5, 6, 7, 8, 9 or 10. In some embodiments, b is 11, 12, 13, 14, 15, 16, 17, 18, 19 or 20. In some embodiments, b is 2, 4, or 6. In some embodiments, b is 2. In some embodiments, b is 4. In some embodiments, b is 6.

In certain embodiments of formula (V), where $L^1$ is —$(CH_2)_a$—NH—C(O)—NH—$(CH_2)_b$—, wherein a is 3 and b is 2, 4, or 6, the compounds may have any one or more of the following structural features:
a) $R^1$ is methyl;
b) $R^2$ is methyl;
c) X is chloro; and
d) one of $R^3$ and $R^4$ is hydrogen and the other is an amino protecting group.

In one variation, the compounds conform to at least one of features (a)-(d). In another variation, the compounds conform to two or more (and in certain variations, all) of features (a)-(d). In a particular variation, the compounds conform to feature (d). In another variation, the compounds conform to features (c) and (d).

The present disclosure provides a compound of Formula (VI):

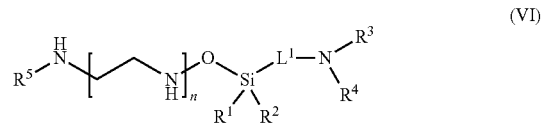

or a salt thereof, wherein
$R^1$ and $R^2$ are independently optionally substituted $C_{1-6}$ alkyl, optionally substituted aryl, or optionally substituted heteroaryl;
$R^3$ and $R^4$ are independently hydrogen, $C_{1-6}$ alkyl, or an amino protecting group;
$R^5$ is hydrogen or optionally substituted $C_{1-6}$ alkyl;
n is a number from one to 1200;
$L^1$ is —$(CH_2)_a$, $(CH_2)_a$—, —$(CH_2)_a$—NH—C(O)—NH—$(CH_2)_b$—, —$(CH_2)_a$—C(O)—NH—$(CH_2)_b$—, or —$(CH_2)_a$—NH—C(O)—$(CH_2)_b$—;
a is a number from one to 20; and
b is a number from one to 20.

In some embodiments of Formula (VI), $R^1$ is optionally substituted $C_{1-6}$ alkyl. In some embodiments, $R^1$ is methyl. In some embodiments, $R^1$ is optionally substituted aryl. In some embodiments, $R^1$ is optionally substituted heteroaryl.

In some embodiments of Formula (VI), $R^2$ is optionally substituted $C_{1-6}$ alkyl. In some embodiments, $R^2$ is methyl. In some embodiments, $R^2$ is optionally substituted aryl. In some embodiments, $R^2$ is optionally substituted heteroaryl.

In some embodiments of Formula (VI), $R^1$ and $R^2$ are $C_{1-6}$ alkyl. In some embodiments, $R^1$ and $R^2$ are methyl.

In some embodiments of Formula (VI), $R^3$ is hydrogen. In some embodiments, $R^3$ is $C_{1-6}$ alkyl. In some embodiments, $R^3$ is an amino protecting group. Examples of suitable amino protecting groups include, but are not limited to t-butoxycarbonyl, trityl, benzyloxycarbonyl, 9-fluorenylmethoxycarbonyl, formyl, trimethylsilyl, t-butyldimethylsilyl, tert-allyloxycarbonyl (Alloc), 9-fluorenylmethyl (Fm, FMOC), methoxycarbonyl, ethoxycarbonyl, benzyl (Bn), 2,2,4,6,7-pentamethyldihydrobenzofuran-5-sulfonyl (Pbf), acetyl, benzoyl, $C_6H_5$—$SO_2$—, 4-$NO_2C_6H_4$—$SO_2$—, 2-$NO_2C_6H_4$—$SO_2$—, and 2,4-$(NO_2)_2C_6H_3$—$SO_2$—.

In some embodiments of Formula (VI), $R^4$ is hydrogen. In some embodiments, $R^4$ is $C_{1-6}$ alkyl. In some embodiments, $R^4$ is an amino protecting group. Examples of suitable amino protecting groups include, but are not limited to t-butoxycarbonyl, trityl, benzyloxycarbonyl, 9-fluorenylmethoxycarbonyl, formyl, trimethylsilyl, t-butyldimethylsilyl, tert-allyloxycarbonyl (Alloc), 9-fluorenylmethyl (Fm, FMOC), methoxycarbonyl, ethoxycarbonyl, benzyl (Bn), 2,2,4,6,7-pentamethyldihydrobenzofuran-5-sulfonyl (Pbf), acetyl, benzoyl, $C_6H_5$—$SO_2$—, 4-$NO_2C_6H_4$—$SO_2$—, 2-$NO_2C_6H_4$—$SO_2$—, and 2,4-$(NO_2)_2C_6H_3$—$SO_2$—.

In some embodiments of Formula (VI), $R^3$ is hydrogen and $R^4$ is an amino protecting group. In some embodiments, $R^3$ is hydrogen and $R^4$ is FMOC. In some embodiments, $R^3$ and $R^4$ are amino protecting groups. In some embodiments, $R^3$ and $R^4$ are hydrogen.

In some embodiments of Formula (VI), $R^5$ is hydrogen. In some embodiments, $R^5$ is optionally substituted $C_{1-6}$ alkyl. In some embodiments, $R^5$ is methyl.

In some embodiments of Formula (VI), L is —(CH$_2$)$_a$—. In some embodiments, L$^1$ is —(CH$_2$)$_a$—NH—C(O)—NH—(CH$_2$)$_b$—. In some embodiments, L$^1$ is —(CH$_2$)$_a$—C(O)—NH—(CH$_2$)$_b$—. In some embodiments, L$^1$ is —(CH$_2$)$_a$—NH—C(O)—(CH$_2$)$_b$—.

In some embodiments, L$^1$ is —(CH$_2$)$_a$—NH—C(O)—NH—(CH$_2$)$_b$—, wherein a is a number from one to 5 and b is a number from one to 10. In some embodiments, L$^1$ is —(CH$_2$)$_a$—NH—C(O)—NH—(CH$_2$)$_b$—, wherein a is a number from one to 5 and b is 2, 4, or 6. In some embodiments, L$^1$ is —(CH$_2$)$_a$—NH—C(O)—NH—(CH$_2$)$_b$—, wherein a is 3 and b is 2, 4, or 6.

In some embodiments of Formula (VI), a is a number from one to 5, 10, or 15. In some embodiments, a is 1, 2, 3, 4, 5, 6, 7, 8, 9 or 10. In some embodiments, a is 11, 12, 13, 14, 15, 16, 17, 18, 19 or 20. In some embodiments, a is 1, 2, 3, 4, or 5. In some embodiments, a is 3.

In some embodiments of Formula (VI), b is a number from one to 5, 10, or 15. In some embodiments, b is 1, 2, 3, 4, 5, 6, 7, 8, 9 or 10. In some embodiments, b is 11, 12, 13, 14, 15, 16, 17, 18, 19 or 20. In some embodiments, b is 2, 4, or 6. In some embodiments, b is 2. In some embodiments, b is 4. In some embodiments, b is 6.

In some embodiments of Formula (VI), n is a number from one to 50, 100, 200, 300, 400, 500, 600, 700, 800, 900, 1000, 1100, or 1200. In some embodiments, n is a number from 50 to 100, 200, 300, 400, 500, 600, 700, 800, 900, 1000, 1100, or 1200. In some embodiments, n is a number from 50 to 1200. In some embodiments, n is 50, 100, 150, 200, 250, 300, 350, 400, 450, 500, 550, 600, 650, 700, 750, 800, 850, 900, 950, 1000, 1050, 1100, 1150, or 1200.

It is understood that any variable for L of formula (VI) may be combined with any variable of n in formula (VI), the same as if each and every combination were specifically and individually listed. For example, in one variation of formula (VI), L$^1$ is —(CH$_2$)$_a$—NH—C(O)—NH—(CH$_2$)$_b$— and n is a number from 50 to 1200.

In certain embodiments of formula (VI), where L$^1$ is —(CH$_2$)$_a$—NH—C(O)—NH—(CH$_2$)$_b$—, wherein a is 3 and b is 2, 4, or 6, the compounds may have any one or more of the following structural features:
a) R$^1$ is methyl;
b) R$^2$ is methyl;
c) n is a number from 50 to 1200; and
d) one of R$^3$ and R$^4$ is hydrogen and the other is an amino protecting group.

In one variation, the compounds conform to at least one of features (a)-(d). In another variation, the compounds conform to two or more (and in certain variations, all) of features (a)-(d). In a particular variation, the compounds conform to feature (d). In another variation, the compounds conform to features (c) and (d).

In certain embodiments of formula (VI), where L$^1$ is —(CH$_2$)$_a$—NH—C(O)—NH—(CH$_2$)$_b$—, wherein a is 3 and b is 2, 4, or 6, the compounds may have any one or more of the following structural features:
a) R$^1$ is methyl;
b) R$^2$ is methyl;
c) n is a number from 50 to 1200; and
d) R$^3$ and R$^4$ are hydrogen.

In one variation, the compounds conform to at least one of features (a)-(d). In another variation, the compounds conform to two or more (and in certain variations, all) of features (a)-(d). In a particular variation, the compounds conform to feature (d). In another variation, the compounds conform to features (c) and (d).

The present disclosure provides a compound of Formula (VII):

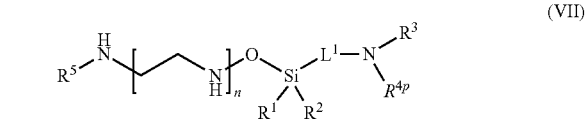

or a salt thereof, wherein

R$^1$ and R$^2$ are independently optionally substituted C$_{1-6}$ alkyl, optionally substituted aryl, or optionally substituted heteroaryl;
R$^3$ is hydrogen or C$_{1-6}$ alkyl;
R$^{4p}$ is a polypeptide, wherein the linkage between R$^{4p}$ and N is with an acyl donor glutamine tag from the polypeptide;
R$^5$ is hydrogen or optionally substituted C$_{1-6}$ alkyl;
n is a number from one to 1200;
L$^1$ is —(CH$_2$)$_a$—, —(CH$_2$)$_a$—NH—C(O)—NH—(CH$_2$)$_b$—, —(CH$_2$)$_a$—C(O)—NH—(CH$_2$)$_b$—, or —(CH$_2$)$_a$—NH—C(O)—(CH$_2$)$_b$—;
a is a number from one to 20; and
b is a number from one to 20.

In some embodiments of Formula (VII), R$^1$ is optionally substituted C$_{1-6}$ alkyl. In some embodiments, R$^1$ is methyl. In some embodiments, R$^1$ is optionally substituted aryl. In some embodiments, R$^1$ is optionally substituted heteroaryl.

In some embodiments of Formula (VII), R$^2$ is optionally substituted C$_{1-6}$ alkyl. In some embodiments, R$^2$ is methyl. In some embodiments, R$^2$ is optionally substituted aryl. In some embodiments, R$^2$ is optionally substituted heteroaryl.

In some embodiments of Formula (VII), R$^1$ and R$^2$ are C$_{1-6}$ alkyl. In some embodiments, R$^1$ and R$^2$ are methyl.

In some embodiments of Formula (VII), R$^3$ is hydrogen. In some embodiments, R$^3$ is C$_{1-6}$ alkyl.

In Formula (VII), R$^{4p}$ is a polypeptide, wherein the linkage between R$^{4p}$ and N is with an acyl donor glutamine tag from the polypeptide. In some embodiments, R$^{4p}$ is a non-targeting polypeptide. In some embodiments, R$^{4p}$ is a targeting polypeptide. In some embodiments, R$^{4p}$ is an Fc-containing polypeptide or a Fab-containing polypeptide. In some embodiments, R$^{4p}$ is an antibody. In some embodiments, R$^{4p}$ specifically binds to an intracellular molecule.

In some embodiments of Formula (VII), R$^5$ is hydrogen. In some embodiments, R$^5$ is optionally substituted C$_{1-6}$ alkyl. In some embodiments, R$^5$ is methyl.

In some embodiments of Formula (VII), L$^1$ is —(CH$_2$)$_a$—. In some embodiments, L$^1$ is —(CH$_2$)$_a$—NH—C(O)—NH—(CH$_2$)$_b$—. In some embodiments, L$^1$ is —(CH$_2$)$_a$—C(O)—NH—(CH$_2$)$_b$—. In some embodiments, L$^1$ is —(CH$_2$)$_a$—NH—C(O)—(CH$_2$)$_b$—.

In some embodiments, L$^1$ is —(CH$_2$)$_a$—NH—C(O)—NH—(CH$_2$)$_b$—, wherein a is a number from one to 5 and b is a number from one to 10. In some embodiments, L$^1$ is —(CH$_2$)$_a$—NH—C(O)—NH—(CH$_2$)$_b$—, wherein a is a number from one to 5 and b is 2, 4, or 6. In some embodiments, L$^1$ is —(CH$_2$)$_a$—NH—C(O)—NH—(CH$_2$)$_b$—, wherein a is 3 and b is 2, 4, or 6.

In some embodiments of Formula (VII), a is a number from one to 5, 10, or 15. In some embodiments, a is 1, 2, 3, 4, 5, 6, 7, 8, 9 or 10. In some embodiments, a is 11, 12, 13, 14, 15, 16, 17, 18, 19 or 20. In some embodiments, a is 1, 2, 3, 4, or 5. In some embodiments, a is 3.

In some embodiments of Formula (VII), b is a number from one to 5, 10, or 15. In some embodiments, b is 1, 2, 3, 4, 5, 6, 7, 8, 9 or 10. In some embodiments, b is 11, 12, 13, 14, 15, 16, 17, 18, 19 or 20. In some embodiments, b is 2, 4, or 6. In some embodiments, b is 2. In some embodiments, b is 4. In some embodiments, b is 6.

In some embodiments of Formula (VII), n is a number from one to 50, 100, 200, 300, 400, 500, 600, 700, 800, 900, 1000, 1100, or 1200. In some embodiments, n is a number from 50 to 100, 200, 300, 400, 500, 600, 700, 800, 900, 1000, 1100, or 1200. In some embodiments, n is a number from 50 to 1200. In some embodiments, n is 50, 100, 150, 200, 250, 300, 350, 400, 450, 500, 550, 600, 650, 700, 750, 800, 850, 900, 950, 1000, 1050, 1100, 1150, or 1200.

It is understood that any variable for L of formula (VII) may be combined with any variable of n in formula (VII), the same as if each and every combination were specifically and individually listed. For example, in one variation of formula (VII), $L^1$ is —$(CH_2)_a$—NH—C(O)—NH—$(CH_2)_b$— and n is a number from 50 to 1200.

In certain embodiments of formula (VII), where $L^1$ is —$(CH_2)_a$—NH—C(O)—NH—$(CH_2)_b$—, wherein a is 3 and b is 2, 4, or 6, the compounds may have any one or more of the following structural features:
a) $R^1$ is methyl;
b) $R^2$ is methyl;
c) n is a number from 50 to 1200; and
d) $R^{4p}$ is a targeting polypeptide.

In one variation, the compounds conform to at least one of features (a)-(d). In another variation, the compounds conform to two or more (and in certain variations, all) of features (a)-(d). In a particular variation, the compounds conform to feature (d). In another variation, the compounds conform to features (c) and (d).

In certain embodiments of formula (VII), where $L_1$ is —$(CH_2)_a$—NH—C(O)—NH—$(CH_2)_b$—, wherein a is 3 and b is 2, 4, or 6, the compounds may have any one or more of the following structural features:
a) $R^1$ is methyl;
b) $R^2$ is methyl;
c) n is a number from 50 to 1200; and
d) $R^{4p}$ is an antibody.

In one variation, the compounds conform to at least one of features (a)-(d). In another variation, the compounds conform to two or more (and in certain variations, all) of features (a)-(d). In a particular variation, the compounds conform to feature (d). In another variation, the compounds conform to features (c) and (d).

Formulae (VIII)-(X)

The present disclosure provides a compound of Formula (VIII):

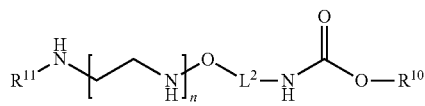

(VIII)

or a salt thereof, wherein
$R^{10}$ is a solid phase resin;
$R^{11}$ is hydrogen or optionally substituted $C_{1-6}$ alkyl;
n is a number from one to 1200;
$L^2$ is —$(C_6H_4)$—$(CH_2)_c$—, —$(C_6H_4)$—NH—$(CH_2)_c$—, —$(C_6H_4)$—C(O)—NH—$(CH_2)_c$—, —$(C_6H_4)$—NH—$(CH_2CH_2O)_d$—$CH_2CH_2$—, or —$(C_6H_4)$—C(O)—NH—$(CH_2CH_2O)_d$—$CH_2CH_2$—;
c is a number from one to 10; and
d is a number from one to 10.

In Formula (VIII), $R^{10}$ is a solid phase resin. Examples of suitable solid phase resins include Amino-PEGA resin, Wang resin, HMPA-PEGA resin, and Trt Chloride resin. In some embodiments, the solid phase resin is Wang resin.

In some embodiments of Formula (VIII), $R^{10}$ is hydrogen. In some embodiments, $R^{10}$ is optionally substituted $C_{1-6}$ alkyl. In some embodiments, $R^{10}$ is methyl.

In some embodiments of Formula (VIII), n is a number from one to 50, 100, 200, 300, 400, 500, 600, 700, 800, 900, 1000, 1100, or 1200. In some embodiments, n is a number from 50 to 100, 200, 300, 400, 500, 600, 700, 800, 900, 1000, 1100, or 1200. In some embodiments, n is a number from 50 to 1200. In some embodiments, n is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (VIII), $L^2$ is —$(C_6H_4)$—$(CH_2)_c$—. In some embodiments, $L^2$ is —$(C_6H_4)$—NH—$(CH_2)_c$—. In some embodiments, $L^2$ is —$(C_6H_4)$—C(O)—NH—$(CH_2)_c$—. In some embodiments, $L^2$ is —$(C_6H_4)$—NH—$(CH_2CH_2O)_d$—$CH_2CH_2$—. In some embodiments, $L^2$ is —$(C_6H_4)$—C(O)—NH—$(CH_2CH_2O)_d$—$CH_2CH_2$—.

In some embodiments, $L^2$ is —$(C_6H_4)$—$(CH_2)_c$—, wherein c is 1, 2, or 3. In some embodiments, $L^2$ is —$(C_6H_4)$—$(CH_2)$—.

In some embodiments, $L^2$ is

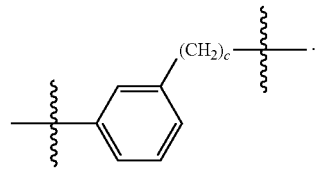

In some embodiments, $L^2$ is

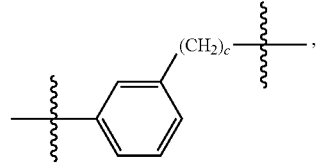

wherein c is 1, 2, or 3. In some embodiments, $L^2$ is

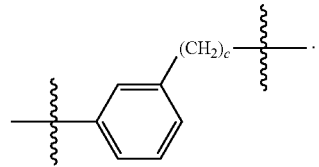

In some embodiments, $L^2$ is —$(C_6H_4)$—C(O)—NH—$(CH_2)_c$—, wherein c is 5, 6, or 7. In some embodiments, $L^2$ is —$(C_6H_4)$—C(O)—NH—$(CH_2)_6$—.

In some embodiments, $L^2$ is

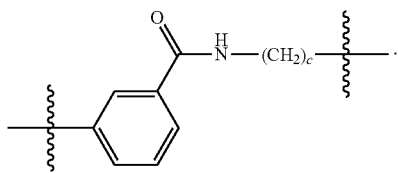

In some embodiments, $L^2$ is

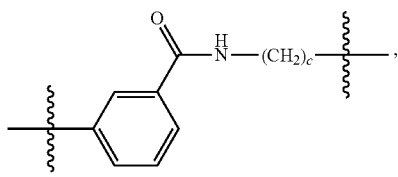

wherein c is 5, 6, or 7. In some embodiments, $L^2$ is

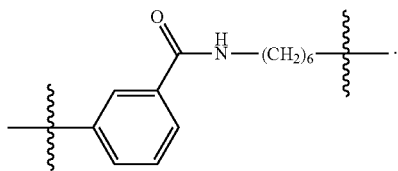

In some embodiments, $L^2$ is —($C_6H_4$)—C(O)—NH—($CH_2CH_2O$)$_d$—$CH_2CH_2$—, wherein d is 1, 2, or 3. In some embodiments, $L^2$ is —($C_6H_4$)—C(O)—NH—($CH_2CH_2O$)$_2$—$CH_2CH_2$—.

In some embodiments, $L^2$ is

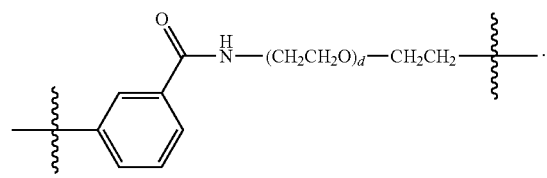

In some embodiments, $L^2$ is

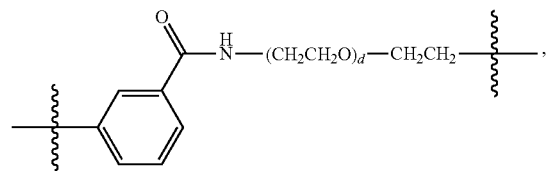

wherein d is 1, 2, or 3. In some embodiments, $L^2$ is

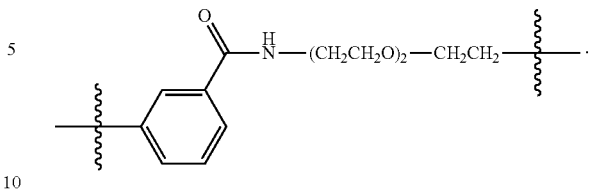

In some embodiments of Formula (VIII), c is 1, 2, 3, 4, 5, 6, 7, 8, 9 or 10. In some embodiments, c is 1, 2, 3, 4, or 5. In some embodiments, c is 1, 2, or 3. In some embodiments, c is 5, 6, or 7. In some embodiments, c is 1. In some embodiments, c is 6.

In some embodiments of Formula (VIII), d is 1, 2, 3, 4, 5, 6, 7, 8, 9 or 10. In some embodiments, d is 1, 2, 3, 4, or 5. In some embodiments, d is 1, 2, or 3. In some embodiments, d is 2.

It is understood that any variable for $L^2$ of formula (VIII) may be combined with any variable of n in formula (VIII), the same as if each and every combination were specifically and individually listed. For example, in one variation of formula (VIII), $L^2$ is —($C_6H_4$)—($CH_2$)$_c$— and n is a number from 50 to 1200. In another variation of formula (VIII), $L^2$ is —($C_6H_4$)—C(O)—NH—($CH_2$)$_c$— and n is a number from 50 to 1200. In another variation of formula (VIII), $L^2$ is —($C_6H_4$)—C(O)—NH—($CH_2CH_2O$)$_2$—$CH_2CH_2$— and n is a number from 50 to 1200.

In certain embodiments of formula (VIII), where $L^2$ is —($C_6H_4$)—($CH_2$)$_c$—, the compounds may have any one or more of the following structural features:
a) $R^{10}$ is Wang resin;
b) $R^{11}$ is methyl; and
c) n is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (VIII), where $L^2$ is —($C_6H_4$)—C(O)—NH—($CH_2$)$_c$—, the compounds may have any one or more of the following structural features:
a) $R^{10}$ is Wang resin;
b) $R^{11}$ is methyl; and
c) n is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (VIII), where $L^2$ is —($C_6H_4$)—C(O)—NH—($CH_2CH_2O$)$_2$—$CH_2CH_2$—, the compounds may have any one or more of the following structural features:
a) $R^{10}$ is Wang resin;
b) $R^{11}$ is methyl; and
c) n is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

The present disclosure provides a compound of Formula (IX):

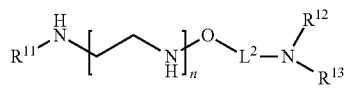
(IX)

or a salt thereof, wherein
$R^{11}$ is hydrogen or optionally substituted $C_{1-6}$ alkyl;
$R^{12}$ is hydrogen or optionally substituted $C_{1-6}$ alkyl;
$R^{13}$ is hydrogen or optionally substituted $C_{1-6}$ alkyl;
n is a number from one to 1200;
$L^2$ is $—(C_6H_4)—(CH_2)_c—$, $—(C_6H_4)—NH—(CH_2)_c—$, $—(C_6H_4)—C(O)—NH—(CH_2)_c—$, $—(C_6H_4)—NH—(CH_2CH_2O)_d—CH_2CH_2—$, or $—(C_6H_4)—C(O)—NH—(CH_2CH_2O)_d—CH_2CH_2—$;
c is a number from one to 10; and
d is a number from one to 10.

In some embodiments of Formula (IX), $R^{11}$ is hydrogen. In some embodiments, $R^{11}$ is optionally substituted $C_{1-6}$ alkyl. In some embodiments, $R^{11}$ is methyl.

In some embodiments of Formula (IX), $R^{12}$ is hydrogen. In some embodiments, $R^{12}$ is $C_{1-6}$ alkyl.

In some embodiments of Formula (IX), $R^{13}$ is hydrogen. In some embodiments, $R^{13}$ is $C_{1-6}$ alkyl.

In some embodiments of Formula (IX), $R^{12}$ and $R^{13}$ are hydrogen.

In some embodiments of Formula (IX), n is a number from one to 50, 100, 200, 300, 400, 500, 600, 700, 800, 900, 1000, 1100, or 1200. In some embodiments, n is a number from 50 to 100, 200, 300, 400, 500, 600, 700, 800, 900, 1000, 1100, or 1200. In some embodiments, n is a number from 50 to 1200. In some embodiments, n is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (IX), $L^2$ is $—(C_6H_4)—(CH_2)_c—$. In some embodiments, $L^2$ is $—(C_6H_4)—NH—(CH_2)_c—$. In some embodiments, $L^2$ is $—(C_6H_4)—C(O)—NH—(CH_2)_c—$. In some embodiments, $L^2$ is $—(C_6H_4)—NH—(CH_2CH_2O)_d—CH_2CH_2—$. In some embodiments, $L^2$ is $—(C_6H_4)—C(O)—NH—(CH_2CH_2O)_d—CH_2CH_2—$.

In some embodiments, $L^2$ is $—(C_6H_4)—(CH_2)_c—$, wherein c is 1, 2, or 3. In some embodiments, $L^2$ is $—(C_6H_4)—(CH_2)—$.

In some embodiments, $L^2$ is

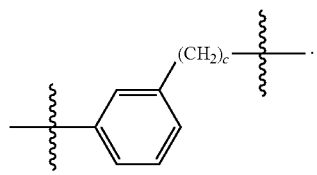

In some embodiments, $L^2$ is

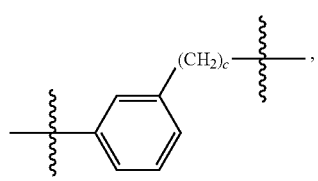

In some embodiments, $L^2$ is

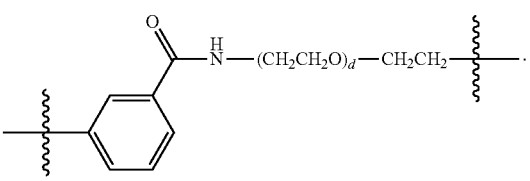

wherein c is 1, 2, or 3. In some embodiments, $L^2$ is

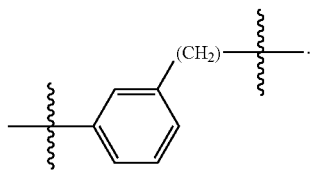

In some embodiments, $L^2$ is $—(C_6H_4)—C(O)—NH—(CH_2)_c—$, wherein c is 5, 6, or 7. In some embodiments, $L^2$ is $—(C_6H_4)—C(O)—NH—(CH_2)_6—$.

In some embodiments, $L^2$ is

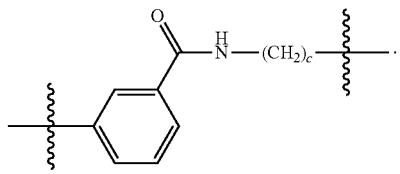

In some embodiments, $L^2$ is

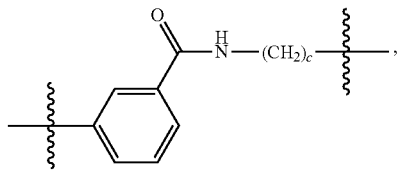

wherein c is 5, 6, or 7. In some embodiments, $L^2$ is

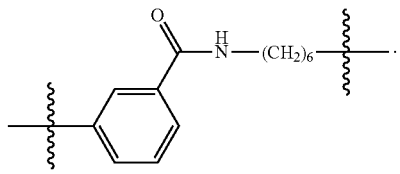

In some embodiments, $L^2$ is $—(C_6H_4)—C(O)—NH—(CH_2CH_2O)_2—CH_2CH_2—$, wherein d is 1, 2, or 3. In some embodiments, $L^2$ is $—(C_6H_4)—C(O)—NH—(CH_2CH_2O)_2—CH_2CH_2—$.

In some embodiments, $L^2$ is

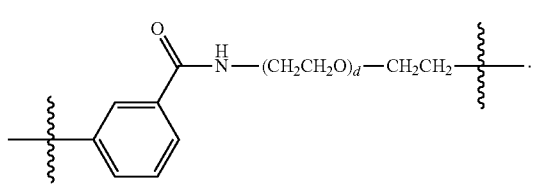

In some embodiments, $L^2$ is

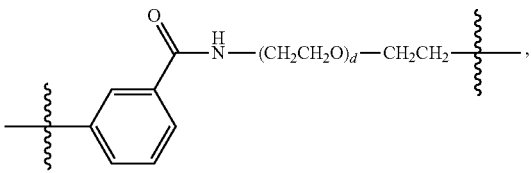

wherein d is 1, 2, or 3. In some embodiments, $L^2$ is

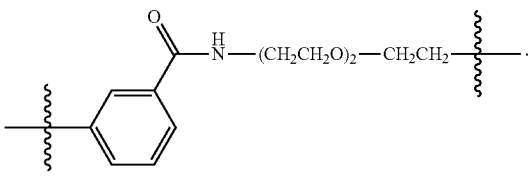

In some embodiments of Formula (IX), c is 1, 2, 3, 4, 5, 6, 7, 8, 9 or 10. In some embodiments, c is 1, 2, 3, 4, or 5. In some embodiments, c is 1, 2, or 3. In some embodiments, c is 5, 6, or 7. In some embodiments, c is 1. In some embodiments, c is 6.

In some embodiments of Formula (IX), d is 1, 2, 3, 4, 5, 6, 7, 8, 9 or 10. In some embodiments, d is 1, 2, 3, 4, or 5. In some embodiments, d is 1, 2, or 3. In some embodiments, d is 2.

It is understood that any variable for $L^2$ of formula (IX) may be combined with any variable of n in formula (IX), the same as if each and every combination were specifically and individually listed. For example, in one variation of formula (IX), $L^2$ is $—(C_6H_4)—(CH_2)_c—$ and n is a number from 50 to 1200. In another variation of formula (IX), $L^2$ is $—(C_6H_4)—C(O)—NH—(CH_2)_c—$ and n is a number from 50 to 1200. In another variation of formula (IX), $L^2$ is $—(C_6H_4)—C(O)—NH—(CH_2CH_2O)_2—CH_2CH_2—$ and n is a number from 50 to 1200.

In certain embodiments of formula (IX), where $L^2$ is $—(C_6H_4)—(CH_2)_c—$, the compounds may have any one or more of the following structural features:
a) $R^{11}$ is methyl;
b) $R^{12}$ and $R^{13}$ are hydrogen; and
c) n is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (IX), where $L^2$ is $—(C_6H_4)—C(O)—NH—(CH_2)_c—$, the compounds may have any one or more of the following structural features:
a) $R^{11}$ is methyl;
b) $R^{12}$ and $R^{13}$ are hydrogen; and
c) n is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (IX), where $L^2$ is $—(C_6H_4)—C(O)—NH—(CH_2CH_2O)_2—CH_2CH_2—$, the compounds may have any one or more of the following structural features:

a) $R^{11}$ is methyl;
b) $R^{12}$ and $R^{13}$ are hydrogen; and
c) n is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

The present disclosure provides a compound of Formula (X):

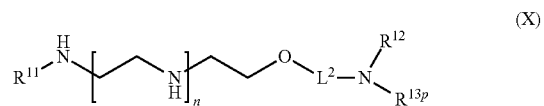

or a salt thereof, wherein $R^{11}$ is hydrogen or optionally substituted $C_{1-6}$ alkyl;

$R^{12}$ is hydrogen or optionally substituted $C_{1-6}$ alkyl;

$R^{13p}$ is a polypeptide, wherein the linkage between $R^{13p}$ and N is with an acyl donor glutamine tag from the polypeptide;

n is a number from one to 1200;

$L^2$ is $—(C_6H_4)—(CH_2)_c—$, $—(C_6H_4)—NH—(CH_2)_c—$, $—(C_6H_4)—C(O)—NH—(CH_2)_c—$, $—(C_6H_4)—NH—(CH_2CH_2O)_d—CH_2CH_2—$, or $—(C_6H_4)—C(O)—NH—(CH_2CH_2O)_d—CH_2CH_2—$;

c is a number from one to 10; and d is a number from one to 10.

In some embodiments of Formula (X), $R^{11}$ is hydrogen. In some embodiments, $R^{11}$ is optionally substituted $C_{1-6}$ alkyl. In some embodiments, $R^{11}$ is methyl.

In some embodiments of Formula (X), $R^{12}$ is hydrogen. In some embodiments, $R^{12}$ is $C_{1-6}$ alkyl.

In Formula (X), $R^{13p}$ is a polypeptide, wherein the linkage between $R^{13p}$ and N is with an acyl donor glutamine tag from the polypeptide. In some embodiments, $R^{13p}$ is a non-targeting polypeptide. In some embodiments, $R^{13p}$ is a targeting polypeptide. In some embodiments, $R^{13p}$ is an Fc-containing polypeptide or a Fab-containing polypeptide. In some embodiments, $R^{13p}$ is an antibody. In some embodiments, $R^{13p}$ specifically binds to an intracellular molecule.

In some embodiments of Formula (X), n is a number from one to 50, 100, 200, 300, 400, 500, 600, 700, 800, 900, 1000, 1100, or 1200. In some embodiments, n is a number from 50 to 100, 200, 300, 400, 500, 600, 700, 800, 900, 1000, 1100, or 1200. In some embodiments, n is a number from 50 to 1200. In some embodiments, n is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (X), $L^2$ is $—(C_6H_4)—(CH_2)_c—$. In some embodiments, $L^2$ is $—(C_6H_4)—NH—(CH_2)_c—$. In some embodiments, $L^2$ is $—(C_6H_4)—C(O)—NH—(CH_2)_c—$. In some embodiments, $L^2$ is $—(C_6H_4)—NH—(CH_2CH_2O)_d—CH_2CH_2—$. In some embodiments, $L^2$ is $—(C_6H_4)—C(O)—NH—(CH_2CH_2O)_d—CH_2CH_2—$.

In some embodiments, $L^2$ is $—(C_6H_4)—(CH_2)_c—$, wherein c is 1, 2, or 3. In some embodiments, $L^2$ is $—(C_6H_4)—(CH_2)—$.

In some embodiments, $L^2$ is

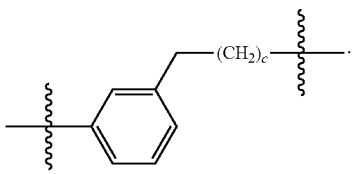

In some embodiments, $L^2$ is

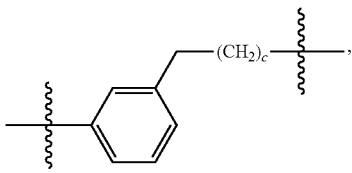

wherein c is 1, 2, or 3. In some embodiments, $L^2$ is

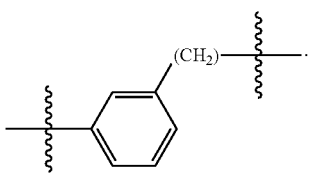

In some embodiments, $L^2$ is $-(C_6H_4)-C(O)-NH-(CH_2)_c-$, wherein c is 5, 6, or 7. In some embodiments, $L^2$ is $-(C_6H_4)-C(O)-NH-(CH_2)_6-$.

In some embodiments, $L^2$ is

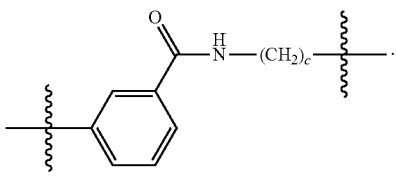

In some embodiments, $L^2$ is

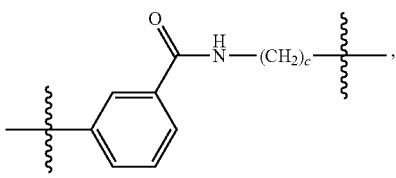

wherein c is 5, 6, or 7. In some embodiments, $L^2$ is

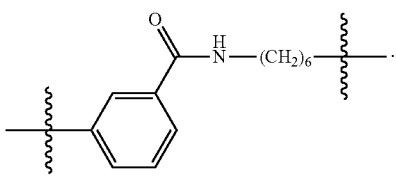

In some embodiments, $L^2$ is $-(C_6H_4)-C(O)-NH-(CH_2CH_2O)_2-CH_2CH_2-$, wherein d is 1, 2, or 3. In some embodiments, $L^2$ is $-(C_6H_4)-C(O)-NH-(CH_2CH_2O)_2-CH_2CH_2-$.

In some embodiments, $L^2$ is

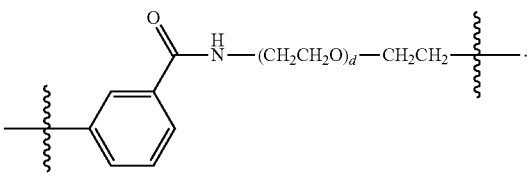

In some embodiments, $L^2$ is

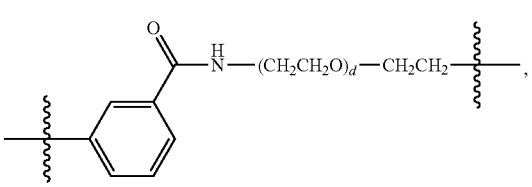

wherein d is 1, 2, or 3. In some embodiments, $L^2$ is

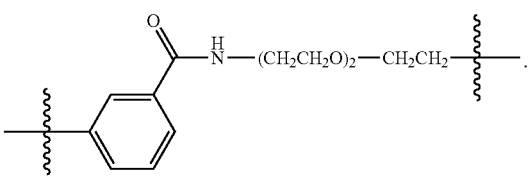

In some embodiments of Formula (X), c is 1, 2, 3, 4, 5, 6, 7, 8, 9 or 10. In some embodiments, c is 1, 2, 3, 4, or 5. In some embodiments, c is 1, 2, or 3. In some embodiments, c is 5, 6, or 7. In some embodiments, c is 1. In some embodiments, c is 6.

In some embodiments of Formula (X), d is 1, 2, 3, 4, 5, 6, 7, 8, 9 or 10. In some embodiments, d is 1, 2, 3, 4, or 5. In some embodiments, d is 1, 2, or 3. In some embodiments, d is 2.

It is understood that any variable for $L^2$ of formula (X) may be combined with any variable of n in formula (X), the same as if each and every combination were specifically and individually listed. For example, in one variation of formula (X), $L^2$ is $-(C_6H_4)-(CH_2)_c-$ and n is a number from 50 to 1200. In another variation of formula (X), $L^2$ is $-(C_6H_4)-C(O)-NH-(CH_2)_c-$ and n is a number from 50 to 1200. In another variation of formula (X), $L^2$ is $-(C_6H_4)-C(O)-NH-(CH_2CH_2O)_2-CH_2CH_2-$ and n is a number from 50 to 1200.

In certain embodiments of formula (X), where $L^2$ is $-(C_6H_4)-(CH_2)_c-$, the compounds may have any one or more of the following structural features:
a) $R^{11}$ is methyl;
b) n is a number from 50 to 1200; and
c) $R^{13p}$ is a targeting polypeptide.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (X), where $L^2$ is —($C_6H_4$)—($CH_2$)$_c$—, the compounds may have any one or more of the following structural features:
a) $R^{11}$ is methyl;
b) n is a number from 50 to 1200; and
c) $R^{13p}$ is an antibody.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (X), where $L^2$ is —($C_6H_4$)—C(O)—NH—($CH_2$)$_c$—, the compounds may have any one or more of the following structural features:
a) $R^{11}$ is methyl;
b) n is a number from 50 to 1200; and
c) $R^{13p}$ is a targeting polypeptide.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (X), where $L^2$ is —($C_6H_4$)—C(O)—NH—($CH_2$)$_c$—, the compounds may have any one or more of the following structural features:
a) $R^{11}$ is methyl;
b) n is a number from 50 to 1200; and
c) $R^{13p}$ is an antibody.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (X), where $L^2$ is —($C_6H_4$)—C(O)—NH—($CH_2CH_2O$)$_2$—$CH_2CH_2$—, the compounds may have any one or more of the following structural features:
a) $R^{11}$ is methyl;
b) n is a number from 50 to 1200; and
c) $R^{13p}$ is a targeting polypeptide.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (X), where $L^2$ is —($C_6H_4$)—C(O)—NH—($CH_2CH_2O$)$_2$—$CH_2CH_2$—, the compounds may have any one or more of the following structural features:
a) $R^{11}$ is methyl;
b) n is a number from 50 to 1200; and
c) $R^{13p}$ is an antibody.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

Formulae (XI)-(XIII)

The present disclosure provides a compound of Formula (XI):

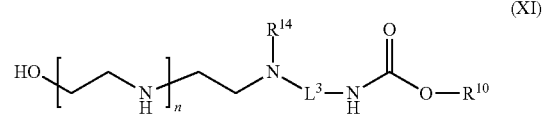

or a salt thereof, wherein
$R^{10}$ is a solid phase resin;
$R^{14}$ is hydrogen, optionally substituted $C_{1-6}$ alkyl, or

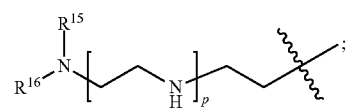

$R^{15}$ is hydrogen or optionally substituted $C_{1-6}$ alkyl;
$R^{16}$ is hydrogen or optionally substituted $C_{1-6}$ alkyl;
n is a number from one to 1200;
p is a number from one to 1200;
$L^3$ is —C(O)—($C_6H_4$)—($CH_2$)$_e$— or —C(O)—($CH_2$)$_e$—; and
e is a number from one to 10.

In Formula (IX), $R^{10}$ is a solid phase resin. Examples of suitable solid phase resins include Amino-PEGA resin, Wang resin, HMPA-PEGA resin, and Trt Chloride resin. In some embodiments, the solid phase resin is Wang resin.

In some embodiments of Formula (XI), $R^{14}$ is hydrogen. In some embodiments, $R^{14}$ is optionally substituted $C_{1-6}$ alkyl. In some embodiments, $R^{14}$ is

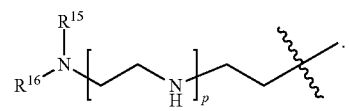

In some embodiments of Formula (XI), $R^{15}$ is hydrogen. In some embodiments, $R^{15}$ is optionally substituted $C_{1-6}$ alkyl. In some embodiments, $R^{15}$ is methyl.

In some embodiments of Formula (XI), $R^{16}$ is hydrogen. In some embodiments, $R^{16}$ is optionally substituted $C_{1-6}$ alkyl. In some embodiments, $R^{16}$ is methyl.

In some embodiments of Formula (XI), $R^{15}$ is $C_{1-6}$ alkyl and $R^{16}$ is hydrogen. In some embodiments, $R^{15}$ is methyl and $R^{16}$ is hydrogen.

In some embodiments of Formula (XI), n is a number from one to 50, 100, 200, 300, 400, 500, 600, 700, 800, 900, 1000, 1100, or 1200. In some embodiments, n is a number from 50 to 100, 200, 300, 400, 500, 600, 700, 800, 900, 1000, 1100, or 1200. In some embodiments, n is a number from 50 to 1200. In some embodiments, n is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (XI), p is a number from one to 50, 100, 200, 300, 400, 500, 600, 700, 800, 900, 1000, 1100, or 1200. In some embodiments, p is a number from 50 to 100, 200, 300, 400, 500, 600, 700, 800, 900, 1000, 1100, or 1200. In some embodiments, p is a number from 50 to 1200. In some embodiments, p is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (XI), n+p is a number from one to 1200. In some embodiments, n+p is a number from one to 50, 100, 200, 300, 400, 500, 600, 700, 800, 900, 1000, 1100, or 1200. In some embodiments, n+p is a number from 50 to 100, 200, 300, 400, 500, 600, 700, 800, 900, 1000, 1100, or 1200. In some embodiments, n+p is a number from 50 to 1200. In some embodiments, n+p is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (XI), $L^3$ is —C(O)—$(C_6H_4)$—$(CH_2)_e$—. In some embodiments of Formula (XI), $L^3$ is —C(O)—$(CH_2)_e$—.

In some embodiments, $L^3$ is —C(O)—$(C_6H_4)$—$(CH_2)_e$—, wherein e is 1, 2, or 3. In some embodiments, $L^3$ is —C(O)—$(C_6H_4)$—$(CH_2)$—.

In some embodiments, $L^3$ is

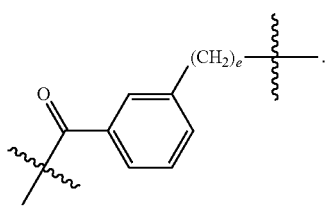

In some embodiments, $L^3$ is

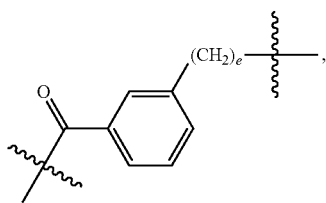

wherein e is 1, 2, or 3. In some embodiments, $L^3$ is

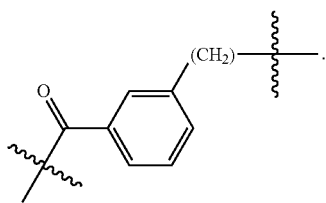

In some embodiments, $L^3$ is —C(O)—$(CH_2)_e$—, wherein e is 4, 5, or 6. In some embodiments, $L^3$ is —C(O)—$(CH_2)_5$—.

In some embodiments of Formula (XI), e is 1, 2, 3, 4, 5, 6, 7, 8, 9 or 10. In some embodiments, e is 1, 2, 3, 4, 5, or 6. In some embodiments, e is 1, 2, or 3. In some embodiments, e is 4, 5, or 6.

It is understood that any variable for $L^3$ of formula (XI) may be combined with any variable of n in formula (XI), the same as if each and every combination were specifically and individually listed. For example, in one variation of formula (XI), $L^3$ is —C(O)—$(C_6H_4)$—$(CH_2)_e$— and n is a number from 50 to 1200. In another variation of formula (XI), $L^3$ is —C(O)—$(CH_2)_e$— and n is a number from 50 to 1200.

It is understood that any variable for $L^3$ of formula (XI) may be combined with any variable of p in formula (XI), the same as if each and every combination were specifically and individually listed. For example, in one variation of formula (XI), $L^3$ is —C(O)—$(C_6H_4)$—$(CH_2)_e$— and p is a number from 50 to 1200. In another variation of formula (XI), $L^3$ is —C(O)—$(CH_2)_e$— and p is a number from 50 to 1200.

It is understood that any variable for $L^3$ of formula (XI) may be combined with any variable of n+p in formula (XI), the same as if each and every combination were specifically and individually listed. For example, in one variation of formula (XI), $L^3$ is —C(O)—$(C_6H_4)$—$(CH_2)_e$— and n+p is a number from 50 to 1200. In another variation of formula (XI), $L^3$ is —C(O)—$(CH_2)_e$— and n+p is a number from 50 to 1200.

In certain embodiments of formula (XI), where $L^3$ is —C(O)—$(C_6H_4)$—$(CH_2)_e$—, the compounds may have any one or more of the following structural features:

a) $R^{10}$ is Wang resin;
b) $R^{14}$ is hydrogen; and
c) n+p is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (X), where $L^3$ is-C(O)—$(CH_2)_e$—, the compounds may have any one or more of the following structural features:

a) $R^{10}$ is Wang resin;
b) $R^{14}$ is hydrogen; and
c) n+p is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

The present disclosure provides a compound of Formula (XII):

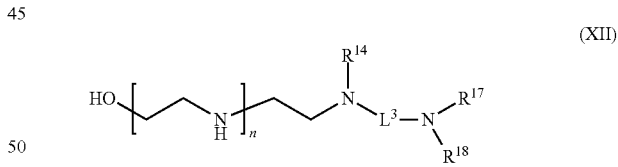 (XII)

or a salt thereof, wherein
$R^{14}$ is hydrogen, optionally substituted $C_{1-6}$ alkyl, or

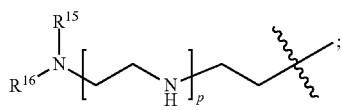

$R^{15}$ is hydrogen or optionally substituted $C_{1-6}$ alkyl;
$R^{16}$ is hydrogen or optionally substituted $C_{1-6}$ alkyl;
$R^{17}$ is hydrogen or optionally substituted $C_{1-6}$ alkyl;
$R^{18}$ is hydrogen or optionally substituted $C_{1-6}$ alkyl;
n is a number from one to 1200;
p is a number from one to 1200;

$L^3$ is —C(O)—($C_6H_4$)—$(CH_2)_e$— or —C(O)—$(CH_2)_e$—; and e is a number from one to 10.

In some embodiments of Formula (XII), $R^{14}$ is hydrogen. In some embodiments, $R^{14}$ is optionally substituted $C_{1-6}$ alkyl. In some embodiments, $R^{14}$ is

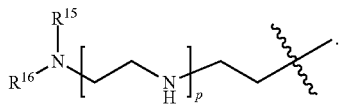

In some embodiments of Formula (XII), $R^{15}$ is hydrogen. In some embodiments, $R^{15}$ is optionally substituted $C_{1-6}$ alkyl. In some embodiments, $R^{15}$ is methyl.

In some embodiments of Formula (XII), $R^{16}$ is hydrogen. In some embodiments, $R^{16}$ is optionally substituted $C_{1-6}$ alkyl. In some embodiments, $R^{16}$ is methyl.

In some embodiments of Formula (XII), $R^{17}$ is hydrogen. In some embodiments, $R^{17}$ is $C_{1-6}$ alkyl.

In some embodiments of Formula (XII), $R^{18}$ is hydrogen. In some embodiments, $R^{18}$ is $C_{1-6}$ alkyl.

In some embodiments of Formula (XII), $R^{17}$ and $R^{18}$ are hydrogen.

In some embodiments of Formula (XII), n is a number from one to 50, 100, 200, 300, 400, 500, 600, 700, 800, 900, 1000, 1100, or 1200. In some embodiments, n is a number from 50 to 100, 200, 300, 400, 500, 600, 700, 800, 900, 1000, 1100, or 1200. In some embodiments, n is a number from 50 to 1200. In some embodiments, n is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (XII), p is a number from one to 50, 100, 200, 300, 400, 500, 600, 700, 800, 900, 1000, 1100, or 1200. In some embodiments, p is a number from 50 to 100, 200, 300, 400, 500, 600, 700, 800, 900, 1000, 1100, or 1200. In some embodiments, p is a number from 50 to 1200. In some embodiments, p is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (XII), n+p is a number from one to 1200. In some embodiments, n+p is a number from one to 50, 100, 200, 300, 400, 500, 600, 700, 800, 900, 1000, 1100, or 1200. In some embodiments, n+p is a number from 50 to 100, 200, 300, 400, 500, 600, 700, 800, 900, 1000, 1100, or 1200. In some embodiments, n+p is a number from 50 to 1200. In some embodiments, n+p is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (XII), $L^3$ is —C(O)—($C_6H_4$)—$(CH_2)_e$—. In some embodiments, $L^3$ is —C(O)—$(CH_2)_e$—.

In some embodiments, $L^3$ is —C(O)—($C_6H_4$)—$(CH_2)_e$—, wherein e is 1, 2, or 3. In some embodiments, $L^3$ is —C(O)—($C_6H_4$)—($CH_2$)—.

In some embodiments, $L^3$ is

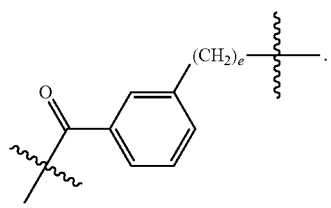

In some embodiments, $L^3$ is

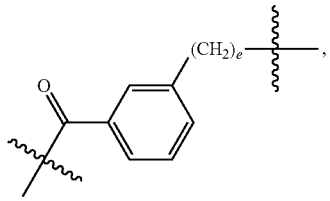

wherein e is 1, 2, or 3. In some embodiments, $L^3$ is

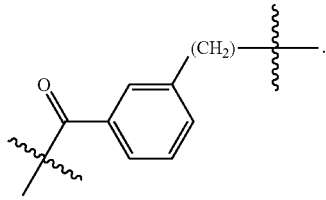

In some embodiments, $L^3$ is —C(O)—$(CH_2)_e$—, wherein e is 4, 5, or 6. In some embodiments, $L^3$ is —C(O)—$(CH_2)_5$—.

In some embodiments of Formula (XII), e is 1, 2, 3, 4, 5, 6, 7, 8, 9 or 10. In some embodiments, e is 1, 2, 3, 4, 5, or 6. In some embodiments, e is 1, 2, or 3. In some embodiments, e is 4, 5, or 6.

It is understood that any variable for $L^3$ of formula (XII) may be combined with any variable of n in formula (XII), the same as if each and every combination were specifically and individually listed. For example, in one variation of formula (XII), $L^3$ is —C(O)—($C_6H_4$)—$(CH_2)_e$— and n is a number from 50 to 1200. In another variation of formula (XII), $L^3$ is —C(O)—$(CH_2)_e$— and n is a number from 50 to 1200.

It is understood that any variable for $L^3$ of formula (XII) may be combined with any variable of p in formula (XII), the same as if each and every combination were specifically and individually listed. For example, in one variation of formula (XII), $L^3$ is —C(O)—($C_6H_4$)—$(CH_2)_e$— and p is a number from 50 to 1200. In another variation of formula (XII), $L^3$ is —C(O)—$(CH_2)_e$— and p is a number from 50 to 1200.

It is understood that any variable for $L^3$ of formula (XII) may be combined with any variable of n+p in formula (XII), the same as if each and every combination were specifically and individually listed. For example, in one variation of formula (XII), $L^3$ is —C(O)—($C_6H_4$)—$(CH_2)_e$— and n+p is a number from 50 to 1200. In another variation of formula (XII), $L^3$ is —C(O)—$(CH_2)_e$— and n+p is a number from 50 to 1200.

In certain embodiments of formula (XII), where $L^3$ is —C(O)—($C_6H_4$)—$(CH_2)_e$—, the compounds may have any one or more of the following structural features:

a) $R^{14}$ is hydrogen;
b) $R^{17}$ and $R^{18}$ are hydrogen; and
c) n+p is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (XII), where $L^3$ is —C(O)—$(CH_2)_e$—, the compounds may have any one or more of the following structural features:
a) $R^{14}$ is hydrogen;
b) $R^{17}$ and $R^{18}$ are hydrogen; and
c) n+p is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

The present disclosure provides a compound of Formula (XIII):

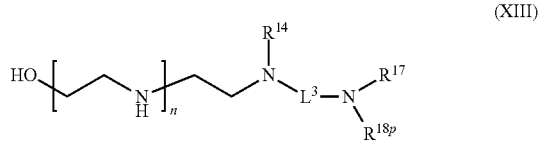

or a salt thereof, wherein
$R^{14}$ is hydrogen, optionally substituted $C_{1-6}$ alkyl, or P

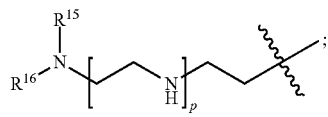

$R^{15}$ is hydrogen or optionally substituted $C_{1-6}$ alkyl;
$R^{16}$ is hydrogen or optionally substituted $C_{1-6}$ alkyl;
$R^{17}$ is hydrogen or optionally substituted $C_{1-6}$ alkyl;
$R^{18p}$ is a polypeptide, wherein the linkage between $R^{18p}$ and N is with an acyl donor glutamine tag from the polypeptide;
n is a number from one to 1200;
p is a number from one to 1200;
$L^3$ is —C(O)—$(C_6H_4)$—$(CH_2)_e$— or —C(O)—$(CH_2)_e$—; and
e is a number from one to 10.

In some embodiments of Formula (XIII), $R^{14}$ is hydrogen. In some embodiments, $R^{14}$ is optionally substituted $C_{1-6}$ alkyl. In some embodiments, $R^{14}$ is

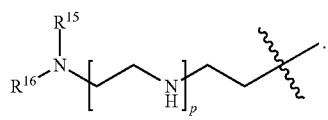

In some embodiments of Formula (XIII), $R^{15}$ is hydrogen. In some embodiments, $R^{15}$ is optionally substituted $C_{1-6}$ alkyl. In some embodiments, $R^{15}$ is methyl.

In some embodiments of Formula (XIII), $R^{16}$ is hydrogen. In some embodiments, $R^{16}$ is optionally substituted $C_{1-6}$ alkyl. In some embodiments, $R^{16}$ is methyl.

In some embodiments of Formula (XIII), $R^{17}$ is hydrogen. In some embodiments, $R^{17}$ is $C_{1-6}$ alkyl.

In Formula (XIII), $R^{18p}$ is a polypeptide, wherein the linkage between $R^{18p}$ and N is with an acyl donor glutamine tag from the polypeptide. In some embodiments, $R^{18p}$ is a non-targeting polypeptide. In some embodiments, $R^{18p}$ is a targeting polypeptide. In some embodiments, $R^{18p}$ is an Fc-containing polypeptide or a Fab-containing polypeptide. In some embodiments, $R^{18p}$ is an antibody. In some embodiments, $R^{18p}$ specifically binds to an intracellular molecule.

In some embodiments of Formula (XIII), n is a number from one to 50, 100, 200, 300, 400, 500, 600, 700, 800, 900, 1000, 1100, or 1200. In some embodiments, n is a number from 50 to 100, 200, 300, 400, 500, 600, 700, 800, 900, 1000, 1100, or 1200. In some embodiments, n is a number from 50 to 1200. In some embodiments, n is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (XIII), p is a number from one to 50, 100, 200, 300, 400, 500, 600, 700, 800, 900, 1000, 1100, or 1200. In some embodiments, p is a number from 50 to 100, 200, 300, 400, 500, 600, 700, 800, 900, 1000, 1100, or 1200. In some embodiments, p is a number from 50 to 1200. In some embodiments, p is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (XIII), n+p is a number from one to 1200. In some embodiments, n+p is a number from one to 50, 100, 200, 300, 400, 500, 600, 700, 800, 900, 1000, 1100, or 1200. In some embodiments, n+p is a number from 50 to 100, 200, 300, 400, 500, 600, 700, 800, 900, 1000, 1100, or 1200. In some embodiments, n+p is a number from 50 to 1200. In some embodiments, n+p is 50, 100, 150, 200, 250, 300, 350, 400, 450, 500, 550, 600, 650, 700, 750, 800, 850, 900, 950, 1000, 1050, 1100, 1150, or 1200.

In some embodiments of Formula (XIII), $L^3$ is —C(O)—$(C_6H_4)$—$(CH_2)_e$—. In some embodiments, $L^3$ is —C(O)—$(CH_2)_e$—.

In some embodiments, $L^3$ is —C(O)—$(C_6H_4)$—$(CH_2)_e$—, wherein e is 1, 2, or 3. In some embodiments, $L^3$ is —C(O)—$(C_6H_4)$—$(CH_2)$—.

In some embodiments, $L^3$ is

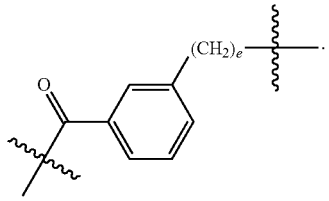

In some embodiments, $L^3$ is

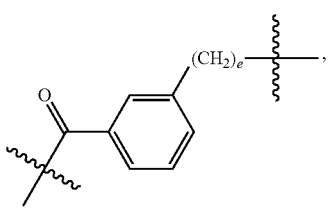

wherein e is 1, 2, or 3. In some embodiments, L³ is

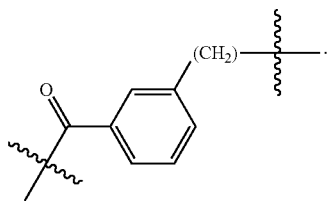

In some embodiments, L³ is —C(O)—(CH₂)$_e$—, wherein e is 4, 5, or 6. In some embodiments, L³ is —C(O)—(CH₂)₅—.

In some embodiments of Formula (XIII), e is 1, 2, 3, 4, 5, 6, 7, 8, 9 or 10. In some embodiments, e is 1, 2, 3, 4, 5, or 6. In some embodiments, e is 1, 2, or 3. In some embodiments, e is 4, 5, or 6.

It is understood that any variable for L³ of formula (XIII) may be combined with any variable of n in formula (XIII), the same as if each and every combination were specifically and individually listed. For example, in one variation of formula (XIII), L³ is —C(O)—(C₆H₄)—(CH₂)$_e$— and n is a number from 50 to 1200. In another variation of formula (XIII), L³ is —C(O)—(CH₂)$_e$— and n is a number from 50 to 1200.

It is understood that any variable for L³ of formula (XIII) may be combined with any variable of p in formula (XIII), the same as if each and every combination were specifically and individually listed. For example, in one variation of formula (XIII), L³ is —C(O)—(C₆H₄)—(CH₂)$_e$— and p is a number from 50 to 1200. In another variation of formula (XIII), L³ is —C(O)—(CH₂)$_e$— and p is a number from 50 to 1200.

It is understood that any variable for L³ of formula (XIII) may be combined with any variable of n+p in formula (XIII), the same as if each and every combination were specifically and individually listed. For example, in one variation of formula (XIII), L³ is —C(O)—(C₆H₄)—(CH₂)$_e$— and n+p is a number from 50 to 1200. In another variation of formula (XIII), L³ is —C(O)—(CH₂)$_e$— and n+p is a number from 50 to 1200.

In certain embodiments of formula (XIII), where L³ is —C(O)—(C₆H₄)—(CH₂)$_e$—, the compounds may have any one or more of the following structural features:
a) $R^{14}$ is hydrogen;
b) $R^{18p}$ is a targeting polypeptide; and
c) n+p is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (XIII), where L³ is —C(O)—(C₆H₄)—(CH₂)$_e$—, the compounds may have any one or more of the following structural features:
a) $R^{14}$ is hydrogen;
b) $R^{18p}$ is an antibody; and
c) n+p is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (XIII), where L³ is-C(O)—(CH₂)$_e$—, the compounds may have any one or more of the following structural features:
a) $R^{14}$ is hydrogen;
b) $R^{18p}$ is a targeting polypeptide; and
c) n+p is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

In certain embodiments of formula (XIII), where L³ is-C(O)—(CH₂)$_e$—, the compounds may have any one or more of the following structural features:
a) $R^{14}$ is hydrogen;
b) $R^{18p}$ is an antibody; and
c) n+p is a number from 50 to 1200.

In one variation, the compounds conform to at least one of features (a)-(c). In another variation, the compounds conform to two or more (and in certain variations, all) of features (a)-(c). In a particular variation, the compounds conform to feature (c). In another variation, the compounds conform to features (b) and (c).

Certain Compounds

The present disclosure provides certain compounds of the above formulae.

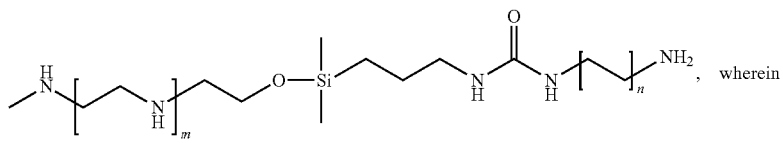

, wherein n is 2, 4, or 6 and m is such that PEI has a molecular weight of about 10,000.

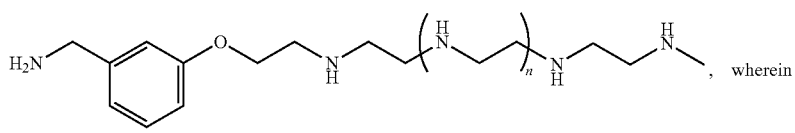

, wherein n is such that PEI has a molecular weight of about 5,000.

-continued

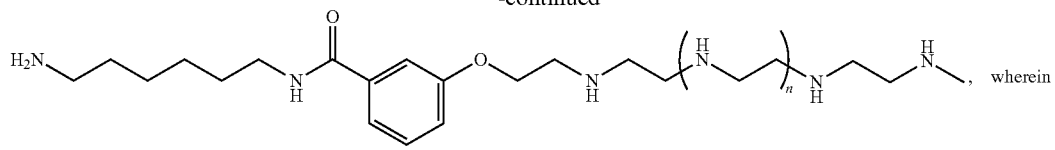

n is such that PEI has a molecular weight of about 5,000.

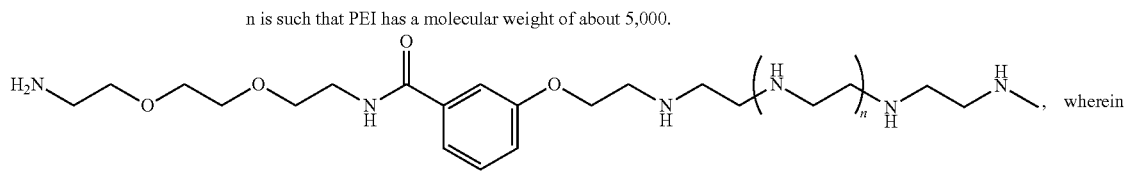

n is such that PEI has a molecular weight of about 5,000.

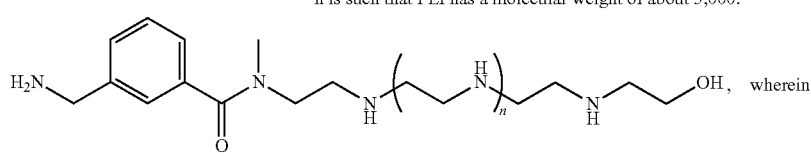

n is such that PEI has a molecular weight of about 5,000.

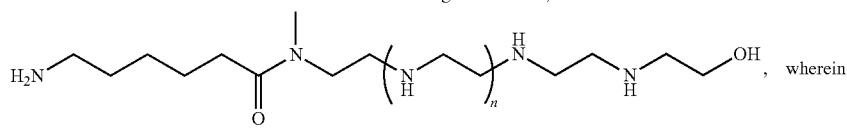

n is such that PEI has a molecular weight of about 5,000.

Polypeptides

The PEI-polypeptide conjugates described herein comprise a polypeptide component, such as $R^{20}$ in Formula (IV), $R^{4p}$ in Formula (VII), $R^{13p}$ in Formula (X), and $R^{18p}$ in Formula (XIII). It is understood that $R^{20}$ in Formula (IV) may comprise any one of the polypeptides described in this section. It is also understood that each of $R^{4p}$ in Formula (VII), $R^{13p}$ in Formula (X), and $R^{18p}$ in Formula (XIII) may comprise any one of the polypeptides described in this section, wherein the polypeptide comprises an acyl donor glutamine tag for conjugation to the PEI compound.

The terms "polypeptide", "oligopeptide", "peptide" and "protein" are used interchangeably herein to refer to chains of amino acids of any length. The chain may be linear or branched, and it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included are, for example, polypeptides containing one or more analogs of an amino acid (including, for example, unnatural amino acids, etc.), as well as other modifications known in the art. It is understood that the polypeptides can occur as single chains or associated chains.

In some embodiments, the polypeptide is a targeting polypeptide. As used herein, "targeting polypeptide" refers to a polypeptide that specifically recognizes or specifically binds to a cell surface molecule that is preferentially expressed on a selected group of cells, such as cells of a specific origin (e.g., pathogen cells), cells of a specific cell type (e.g., immune cells), cells of a specific tissue or organ, cells of specific physiological state (e.g., tumor cells), or cells of specific differentiation state (e.g., stem cells). The targeting polypeptide may do this directly, by directly recognizing the cell surface molecule or moiety, or indirectly, by recognizing and interacting with an endogenous molecule that specifically recognizes or specifically binds to a cell surface molecule that is preferentially expressed on a selected group of cells, such as cells of a specific origin (e.g., pathogen cells), cells of a specific cell type (e.g., immune cells), cells of a specific tissue or organ, cells of specific physiological state (e.g., tumor cells), or cells of specific differentiation state (e.g., stem cells). "Preferentially expressed" may refer to a level of expression of the cell surface molecule that may be at least any one of 2, 5, 10, 20, 50, 100, 500, $10^3$, $10^4$, $10^5$, $10^6$ or more fold higher on the selected group of cells than on other cells. Cell surface molecule can be of any molecular moiety, such as a protein, lipid, or carbohydrate. Exemplary cell surface molecules include, but are not limited to, cell surface receptors, transmembrane proteins (e.g. transporters and GPCRs), glycoproteins, and cell surface antigens (e.g., tumor associated antigen or tumor specific antigen). In some embodiments, the targeting polypeptide is a ligand of a cell surface molecule, such as a cell surface receptor. In some embodiments, the targeting polypeptide is an antibody that either directly or indirectly interacts with a cell surface molecule, such as a cell surface antigen. In some embodiments, the targeting polypeptide is an immunoadhesin or other engineered molecules that either directly or indirectly specifically recognizes a cell surface molecule. In some embodiments, the targeting polypeptide is a fusion protein (such as bispecific or multispecific antibody) that either directly or indirectly specifically recognizes at least two (such as any of 2, 3, 4, 5, or more) epitopes of a single cell surface molecule. In some embodiments, the targeting polypeptide is a fusion protein (such as bispecific or multispecific antibody) that either directly or indirectly specifically recognizes at least two (such as any of 2, 3, 4, 5, or more) cell surface molecules.

In some embodiments, the polypeptide is a non-targeting polypeptide. A "non-targeting polypeptide" may be a polypeptide that does not recognize or bind to any cell surface molecule, or a polypeptide that specifically recognizes a cell surface molecule that is ubiquitously expressed, or broadly expressed on a large variety of cells. In some embodiments, the non-targeting polypeptide is an antibody that specifically recognizes an intracellular molecule. In some embodiments, the non-targeting polypeptide is a ligand of an intracellular molecule. In some embodiments, the non-targeting polypeptide is a modulator (such as inhibitor or activator) of an intracellular molecule. In some embodiments, the non-targeting polypeptide is a toxin polypeptide (or a toxin protein).

In some embodiments, the polypeptide is a Fab-containing polypeptide. In some embodiments, the Fab-containing polypeptide comprises any one of 1, 2, 3, 4, 5, or more Fab domains. In some embodiments, the Fab-containing polypeptide specifically recognizes a single epitope. In some embodiments, the Fab-containing polypeptide specifically recognizes at least two (such as any of 2, 3, 4, 5, 6, or more) epitopes of the same molecule. In some embodiments, the Fab-containing polypeptide specifically recognizes at least two (such as any of 2, 3, 4, 5, 6, or more) molecules. In some embodiments, the Fab-containing polypeptide specifically recognizes a cell surface molecule, such as a cell surface receptor, or a cell surface antigen. In some embodiments, the Fab-containing polypeptide specifically recognizes an intracellular molecule. In some embodiments, the Fab-containing polypeptide specifically recognizes both a cell surface molecule and an intracellular molecule.

In some embodiments, the polypeptide is an Fc-containing polypeptide. In some embodiments, the polypeptide is an immunoadhesin. In some embodiments, the polypeptide is an engineered Fc-containing polypeptide comprising a specific binding domain. In some embodiments, the Fc-containing polypeptide comprises at least two (such as any of 2, 3, 4, 5, or more) specific binding domains. In some embodiments, the specific binding domain (e.g. directly or indirectly) targets a cell surface molecule, such as a cell surface receptor, or a cell surface antigen. In some embodiments, the specific binding domain (e.g. directly or indirectly) targets an intracellular molecule. In some embodiments, the Fc-containing polypeptide comprises a specific binding domain that (e.g. directly or indirectly) targets a cell surface molecule and a specific binding domain that (e.g. directly or indirectly) targets an intracellular molecule. In some embodiments, the Fc portion of the Fc-containing polypeptide serves to dimerize different binding domains. In some embodiments, the Fc portion of the Fc-containing polypeptide improves pharmacokinetic and pharmacodynamic properties (such as stability, half-life in the serum, etc.) of the polypeptide.

In some embodiments, the polypeptide is an antibody. In some embodiments, the polypeptide is a monoclonal antibody or a polyclonal antibody. In some embodiments, the polypeptide is a human, humanized, chimeric, or murine antibody. In some embodiments, the polypeptide is a full length antibody. In some embodiments, the polypeptide is a minibody or a diabody. In some embodiments, the polypeptide is an antigen-binding fragment selected from the group consisting of Fab, Fab', F(ab')$_2$, Fv, scFv and other antigen-binding subsequences of the full length antibody. In some embodiments, the polypeptide is a bispecific or multispecific antibody.

In some embodiments, the antibody is an IgG. In some embodiments, the IgG is selected from the group consisting of IgG1, IgG2, IgG3, and IgG4. In some embodiments, the antibody is an IgA, IgE, IgD, or IgM.

In some embodiments, the antibody specifically binds (e.g. directly or indirectly) to a cell surface molecule, such as a cell surface receptor, or a cell surface antigen. In some embodiments, the antibody specifically binds (e.g. directly or indirectly) to an intracellular molecule. In some embodiments, the antibody comprises a domain that specifically binds (e.g. directly or indirectly) to a cell surface molecule and a domain that specifically binds (e.g. directly or indirectly) to an intracellular molecule. In some embodiments, the polypeptide is a multispecific antibody (such as a bispecific antibody) comprising a first binding domain that specifically binds (e.g. directly or indirectly) to an intracellular molecule and a second binding domain that specifically binds (e.g. directly or indirectly) to an extracellular molecule. In some embodiments, the polypeptide is a bispecific antibody.

The polypeptide is conjugated to the adjacent group in the PEI-polypeptide conjugate or another biologically active molecule via a chemical reaction (such as a thiol reaction or a click chemistry reaction), or an enzyme reaction. In some embodiments, the conjugation is site-specific, i.e., via one or more reactive residues at specific positions in the polypeptide. In some embodiments, the conjugation is non-specific. In some embodiments, the conjugation is via any one or more of a group of residues having the same functional group or chemical reactivity.

In some embodiments, the polypeptide comprises an endogenous residue that is reactive for conjugation to a functional group (e.g., the functional group in the precursor compound of the PEI-polypeptide conjugate, such as any compound of Formulae (I)-(III), (VI), (IX) and (XII); or a functional group in a biologically active molecule). In some embodiments, the endogenous residue is an amino acid residue, such as cysteine residue or lysine residue. In some embodiments, wherein the polypeptide is a glycoprotein or glycopeptide, the endogenous residue is a carbohydrate moiety.

In some embodiments, the polypeptide comprises an engineered residue that is reactive for conjugation to a functional group (e.g., the functional group in the precursor compound of the PEI-polypeptide conjugate, such as any compound of Formulae (I)-(III), (VI), (IX) and (XII); or a functional group in a biologically active molecule). In some embodiments, the engineered residue is an amino acid residue introduced to the polypeptide by amino acid insertion, or substitution for one or more wild-type amino acids in the polypeptide. In some embodiments, the engineered residue is an endogenous amino acid residue made available (e.g., accessible, exposed, or reactive) for conjugation by chemical reaction (such as oxidation or reduction); by polypeptide engineering, such as insertion, deletion, or substitution of one or more wildtype amino acids in proximity to the engineered residue; or by removing post-translational modification on the endogenous residue, such as deglycosylation. In some embodiments, the engineered residue is a carbohydrate residue introduced to the polypeptide by glycoengineering.

The polypeptide may comprise any number (such as any of 1, 2, 3, 4, 5, or more) of the reactive residues. Each reactive residue may be present at or engineered to any location of the polypeptide, including the N-terminus, the C-terminus, or an internal position of a polypeptide chain. In some embodiments, wherein the polypeptide is an antibody, the reactive residue is linked to or located in the heavy chain, the light chain, or both the heavy chain and the light chain. In some embodiments, wherein the polypeptide has at least two chains, the reactive residue may be present or engineered in each of the at least two chains, or any one or more of the at least two chains. The location of a reactive residue is selected based on the availability, reactivity and physical properties of the reactive residue, and/or on the impact of the conjugation via the reactive residue to the structure, activity, and other physical (e.g., stability and solubility) and/or biological properties of the polypeptide. In some embodiments, a panel of endogenous residues of the polypeptide is screened to select for one or more reactive residues for conjugation. In some embodiments, a panel of positions in the polypeptide is engineered and screened to select for one or more reactive residues for conjugation.

Conjugation at specific reactive residues can be measured by various techniques, including, but not limited to, mass spectrometry (e.g., matrix-assisted laser-desorption ionization mass spectrometry (MALDI-MS), electrospray ionization mass spectrometry (ESI-MS), tandem mass spectrometry (MS), and time-of-flight mass spectrometry (TOF-MS)), hydrophobic interaction chromatography, ion exchange chromatography, site-directed mutagenesis, fluorescence-labeling, size exclusion chromatography, and X-ray crystallography. Impact of conjugation on the polypeptide can be measured by various techniques known in the art, including, but not limited to, binding assays, thermal shift assay, Circular Dichroism spectroscopy, gel electrophoresis, dynamic light scattering, and functional assays (such as cell killing assay, transcription assay, immunoassays, etc.) depending on the activity of the wildtype polypeptide.

In some embodiments, each reactive residue in the polypeptide is conjugated. In some embodiments, only a selected group of all reactive residues in the polypeptide are conjugated. In some embodiments, conjugation at one reactive residue in the polypeptide precludes (e.g., by steric hindrance) conjugation at a second reactive residue in the polypeptide. In some embodiments, the polypeptide comprises a first reactive residue for conjugation with a first compound via a first conjugation reaction, and a second reactive residue for conjugation with a second compound via a second conjugation reaction, wherein the first conjugation reaction and the second conjugation reaction are orthogonal, for example, the first conjugation reaction is a thiol reaction and the second conjugation reaction is a click reaction or vice versa, or the first conjugation reaction is a chemical reaction and the second conjugation reaction is an enzyme reaction or vice versa, or the first conjugation reaction is an enzyme reaction using a first enzyme and the second conjugation reaction is an enzyme reaction using a second, orthogonal enzyme.

Any conjugation methods for polypeptides known in the art may be used to conjugate the endogenous or engineered residue to the adjacent functional group in the PEI-polypeptide conjugate, including, but not limited to conventional lysine and cysteine conjugation methods, conjugation via incorporated unnatural amino acids in the polypeptide, conjugation via incorporated selenocysteines in the polypeptide, transglutamination reaction (e.g., using wildtype or engineered transglutaminase), glycoengineering conjugation methods, conjugation using a formylglycine generating enzyme, conjugation using next generation maleimides (NGMs), conjugation using bifunctional linkers (such as bis-alkylating reagents), and conjugation using a sortase enzyme. See, for example, Sochaj et al. Biotechnology Advances, (2015), 33(6): 775-784. In some embodiments, the endogenous or engineered residue is pre-treated or activated by a chemical reaction (such as oxidation or reduction), or an enzyme reaction (such as deglycosylation) prior to the conjugation.

In some embodiments, the polypeptide comprises an endogenous or engineered cysteine residue with a free sulfhydryl group available for reaction with thiol-reactive compounds (such as any compound of Formulae (I)-(III); or a biologically active molecule comprising a thiol-reactive functional group). In some embodiments, the polypeptide comprises a pair of endogenous or engineered cysteine residues with their thiol side chains normally forming a disulfide bond (—S—S—). In some embodiments, the disulfide bond is reduced by a reducing agent (such as free cysteine, beta-mercaptoethanol, DTT, or TCEP) to provide a reduced sulfhydryl group available for reaction with thiol-reactive compounds (such as compounds of Formulae (I)-(III), or a biologically active molecule comprising a thiol-reactive functional group). In some embodiments, the free or reduced sulfhydryl group in the polypeptide is conjugated via an alkylation reaction, for example, by reacting with a linker or biologically active molecule containing a maleimide group. See, for example, Junutula et al. Nature Biotech (2008) 26: 925-932. In some embodiments, the free or reduced sulfhydryl group in the polypeptide is conjugated via an acylation reaction, such as with an acryloyl-containing linker. In some embodiments, the free or reduced sulfhydryl group in the polypeptide is conjugated via a disulfide exchange reaction, such as with a sulfhydryl-containing linker. In some embodiments, a pair of reduced sulfhydryl groups in a disulfide bond of the polypeptide (e.g., any of the disulfide bonds in the hinge or Fab regions of an antibody) is re-bridged in the conjugation reaction, for example, with a linker or biologically active molecule containing the function group

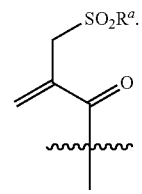

See, for example, Badescu et al., Bioconjugate Chem. (2014), 25(6): 1124-1136.

In some embodiments, the polypeptide comprises an endogenous or engineered residue (such as cysteine or lysine) that is activated by a bifunctional molecule having a functional group that is reactive in a click reaction. In some embodiments, the polypeptide comprises an endogenous or engineered carbohydrate moiety that is reduced to an aldehyde group (e.g., by treating with $NaIO_4$), wherein the aldehyde group is conjugated to an alkoxyamino ($H_2N$—O—) group in any compound of Formula (I)-(III), or in a biologically active molecule, via a click reaction. In some embodiments, the carbohydrate moiety is introduced to the polypeptide via a glycosyltransferase, such as a galactosyltransferase or a sialytransferase. See, for example, Zhou et al., Bioconjug. Chem. (2014), 25: 510-520; and Zhou et al., Bioconjug. Chem. (2014) 25: 138-146.

In some embodiments, the polypeptide comprises an endogenous or engineered residue that is available for conjugation via an enzyme reaction. In some embodiments, the endogenous or engineered residue is a carbohydrate moiety that is recognizable and modifiable by a glycosyltransferase. For example, a polypeptide (e.g., wildtype or engineered glycoprotein) with a specific carbohydrate moiety (e.g., N-acetylgalactosamine) may be modified by a glycosyltransferase (e.g., galactosyltransferase) in a glycosylation reaction with a carbohydrate unit having a functional group that is reactive in a thiol reaction or a click chemistry reaction. In some embodiments, the specific carbohydrate moiety on the polypeptide is treated with a second enzyme (such as galactosidase) to remove terminal carbohydrate residues prior to the glycosylation reaction. See, for example, Zeglis et al. *Bioconjugate Chem.*, (2013), 24 (6): 1057-1067.

In some embodiments, the polypeptide comprises an unnatural amino acid having a functional group suitable for a chemical reaction (such as click reaction) with any compound of Formula (I)-(III), or a biologically active molecule having a functional group reactive in the chemical reaction (such as click reaction). Methods of incorporating one or more unnatural amino acids in a polypeptide are known in the art, for example, by organic synthesis or semi-synthesis of the polypeptide, cell-free protein expression, or by direct genetic encoding of the unnatural amino acids using genetically engineered tRNA/synthetase pairs. See, for example, Liu C. C. and Schultz P. G. *Annual Review of Biochemistry*, (2010) 79: 413-444; Cho, et al. *Proc. Natl. Acad. Sci. USA* (2011), 108: 10437; Axup et al., *Proc. Natl. Acad. Sci. USA*, (2012) 109: 16101-16106; Zimmerman et al., *Bioconjugate Chem.* (2014) 25: 351-361; and Feng, et al. *Proc. Natl. Acad. Sci. USA* (2014) 111: 1766.

In some embodiments, the functional group suitable for click chemistry that is introduced to the polypeptide via bifunctional linker, enzyme reaction, or unnatural amino acids, is selected from azido, alkynyl, oxiranyl, thiiranyl, aziridinyl, aldehyde, acyl, alkoxyamino, hydrazine, and amino. In some embodiments, the functional group is an azido or alkynyl group suitable for conjugation via a dibenzocyclooctyl (DBCO) copper-free click reaction.

In some embodiments, the polypeptide comprises an endogenous or engineered sequence (also referred herein as "tag") that is specifically recognized by the enzyme used in an enzyme reaction for conjugating to a functional group in any of the compounds of Formulae (I)-(III), (VI), (IX) and (XII), or a biologically active molecule. The polypeptide may comprise any number of copies (such as any of 1, 2, 3, 4, 5, or more) of the tag. In some embodiments, the wildtype sequence of the polypeptide is searched for candidate tag positions based on sequence similarity, and a candidate position may be engineered by amino acid deletion, insertion, substitution, or any combination thereof to provide a tag sequence. In some embodiments, a tag sequence is introduced to the N-terminus, the C-terminus, or an internal position (such as structurally flexible regions) of one or more chains of the polypeptide by amino acid insertion, deletion, substitution, or any combination thereof to provide a tag sequence. In some embodiments, wherein the polypeptide is an antibody, the tag is linked to or located in the heavy chain, the light chain, or both the heavy chain and the light chain. In some embodiments, wherein the polypeptide has at least two chains, the tag may be present or engineered in each of the at least two chains, or any one or more of the at least two chains. The location of a tag is also based on substrate preference of the enzyme, the availability, reactivity and physical properties of a reactive residue within the candidate tag positions, and/or the impact of conjugation via the candidate tag positions to the structure, activity, and other physical (e.g., stability and solubility) and/or biological of the polypeptide. In some embodiments, a panel of candidate tag positions in the polypeptide is screened to select for one or more endogenous or engineered tag positions for conjugation.

In some embodiments, each tag in the polypeptide is conjugated in the enzyme reaction. In some embodiments, only a selected group of all tags in the polypeptide are conjugated in the enzyme reaction. In some embodiments, conjugation at one tag in the polypeptide precludes (e.g., by steric hindrance) conjugation at a second tag in the polypeptide. In some embodiments, the polypeptide comprises a first tag for conjugation with a first compound via a first enzyme reaction, and a second tag for conjugation with a second compound via a second enzyme reaction, wherein the first enzyme reaction and the second enzyme reaction are orthogonal.

In some embodiments, the polypeptide comprises an acyl donor glutamine-containing tag (or Q tag) or an endogenous glutamine made reactive by polypeptide engineering, wherein the acyl donor glutamine-containing tag or the endogenous glutamine is conjugated to an amine donor group in any of the compounds of Formulae (I)-(III), (VI), (IX), and (XII), or an amine donor group in a biologically active molecule via a transglutamination reaction catalyzed by a transglutaminase. Transglutaminases (EC2.3.2.13; protein-glutamine:gamma-glutamyltransferse; protein-glutamine: amine γ-glutamyltransferase; CAS 80146-85-6) belong to a family of enzymes that catalyze the acyl addition to a primary amine, wherein the gamma-carboxamide group of peptide-bound γ-glutanyl residue is the acyl donor and the primary amine is the acyl acceptor and the amine donor. In some embodiments, the acyl donor glutamine-containing tag comprises an amino acid sequence XXQX (SEQ ID NO: 1), wherein X is any amino acid. In some embodiments, the acyl donor glutamine-containing tag comprises an amino acid sequence LLQGG (SEQ ID NO:2), LLQGA (SEQ ID NO:3), LLQG (SEQ ID NO:4) or LLQ. In some embodiments, the acyl donor glutamine-containing tag is not spatially adjacent to a reactive lysine. In some embodiments, wherein the polypeptide is an Fc-containing polypeptide (such as an antibody), the acyl donor glutamine-containing tag is engineered by an amino acid substitution for asparagine to glutamine at position 297 of human IgG (Kabat numbering scheme). In some embodiments, the endogenous glutamine that is reactive in transglutamination reaction is made available by deglycosylation of an Fc-containing polypeptide (such as an antibody). In some embodiments the glutamine acceptor in a IgG is contained in the sequence PWEEQYNST (SEQ ID NO:9) when the antibody is deglycosylated, or in a engineered antibody where N is substituted for A or any other amino acid except N or T is substituted for any other amino acid except S or T. In some embodiments the acceptor glutamine is contained in another naturally occurring sequence like VLNLAQSKNFH (SEQ ID: 10) found in IL-2 or APALQPTQGAM (SEQ ID: 11) found in filgrastim or IPKEQKYSF (SEQ ID: 12) found in human growth hormone or MGGSPLAQSHGGS (SEQ ID: 13) found in myoglobin or contained in S-tag KETAAAKFERQHMDS (SEQ ID: 14) or TEYGLFQINNDS (SEQ ID: 15) found in alpha-lactoalbumin or any other naturally occurring protein sequence. In some embodiments the glutamine acceptor sequence can be contained in a sequence derived by phage display, for example, WALQRPH (SEQ ID:16) or WALQRPYTLTES (SEQ ID:17), or WALQRPHYSYPD (SEQ ID:18) or WSPIPQMRTVPP (SEQ ID:19) or NPKIYPMQGWFV (SEQ ID:20) or YELQRPYHSELP (SEQ ID:21) or any other phage display derived peptide containing an acceptor glutamine. Exemplary methods of site-specific polypeptide conjugation using transglutamination reaction have been described, for example, in U.S. Patent Application Publication No. US20130230543; and Dennier et al., *Bioconjugate Chem.* (2014), 25 (3): 569-578. Any transglutaminase known in the art may be used for the transglutamination reaction. In some embodiments, the transglutaminase is a microbial protein. In some embodiments, the transglutaminase is a purified transglutaminase. In some embodiments, the transglutaminase is a calcium-independent transglutaminase. In some embodiments, the transglutaminase is an engineered transglutaminase.

In some embodiments, the polypeptide comprises a sortase recognition tag attached to the C-terminus of the polypeptide, wherein the sortase recognition tag is cleaved and conjugated to an amino group in a polyglycine-containing compound of Formulae (I)-(III), or a biologically active molecule via a transpeptidation reaction catalyzed by a sortase. Sortases are a group of prokaryotic enzymes that normally modify surface proteins by recognizing and cleaving a carboxyl-terminal sorting signal peptide in the protein, and covalently conjugating the protein to cell wall components. In some embodiments, wherein the polypeptide is an antibody, the sortase recognition tag is attached to the C-terminus of the heavy chain, the light chain, or both the heavy chain and the light chain. In some embodiments, the sortase recognition tag comprises an amino acid sequence LPXTG (SEQ ID NO:5), wherein X is any amino acid. In some embodiments, the polyglycine motif comprises at least about any of 2, 3, 4, 5, or more consecutive glycine residues, and the N-terminal glycine has a free amino group for conjugation. In some embodiments, the polyglycine motif comprises about 3 to about 5 consecutive glycine residues, and the N-terminal glycine has a free amino group for conjugation. In some embodiments, the sortase is sortase A (EC 3.4.22.70), such as a sortase A from *Staphylococcus aureus*. Exemplary methods of site-specific polypeptide conjugation using a sortase have been described, for example, in Beerli et al., *PLoS One* (2015), 10(7): e0131177.

In some embodiments, the polypeptide comprises an aldehyde tag recognized by a formylglycine generating enzyme (FGE), wherein a cysteine or serine residue in the aldehyde tag is converted to 2-formylglycine by the FGE, and the formyglycine is conjugated to an alkoxyamino (H₂N—O—) group-containing compound of Formulae (I)-(III), or a biologically active molecule via a click reaction. Formylglycine-generating enzymes are enzymes that oxidize cysteine or serine in a sulfatase motif to 2-fomylglycine (also referred to as formylglycine, or fGly). In some embodiments, the aldehyde tag comprises an amino acid sequence LCTPSR (SEQ ID NO: 6), wherein the cysteine residue in the aldehyde tag is converted to 2-formylglycine by the FGE and used for conjugation. In some embodiments, the FGE is a prokaryotic FGE. In some embodiments, the FGE is a eukaryotic FGE. Exemplary methods of site-specific polypeptide conjugation using an FGE have been described, for example, in U.S. Patent Application Publication NOs. US20100210543 and US. 2012097333.

In some embodiments, the polypeptide further comprises a label. In some embodiments, the label is a detectable marker incorporated by any of a multitude of methods known in the art. For example, a polypeptide comprising biotinyl moieties can be detected by marked avidin (e.g., streptavidin containing a fluorescent marker or enzymatic activity that can be detected by optical or colorimetric methods). Exemplary labels for the polypeptide include, but are not limited to, radioisotopes or radionuclides, fluorescent labels, enzymatic labels (e.g., horseradish peroxidase, β-ga- lactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates. In some embodiments, the label is conjugated to the polypeptide via a spacer arm of various lengths to reduce potential steric hindrance.

In some embodiments, the polypeptide further comprises a biocompatible polymer. In some embodiments, the biocompatible polymer improves the biological characteristics of the polypeptide, such as to increase serum half-life and bioactivity, and/or to extend in vivo half-lives. Examples of biocompatible polymers include water-soluble polymer, such as polyethylene glycol (PEG) or derivatives thereof and zwitterion-containing biocompatible polymers (e.g., a phosphorylcholine containing polymer).

III. Complexes

The present disclosure further provides complexes comprising any one of the PEI-polypeptide conjugates described herein, such as compounds of Formulae (IV), (VII), (X), and (XIII), and a biologically active molecule.

The present disclosure provides a complex comprising a compound of formula (IV):

or a salt thereof, wherein
PEI is polyethylenimine, which terminates with —OH or —NHR, wherein R is hydrogen or $C_{1-6}$ alkyl;
$L^{10}$ is a linker;
q is a number from one to 100; and
$R^{20}$ is a polypeptide; and
a biologically active molecule.

The present disclosure provides a complex comprising a compound of formula (VII):

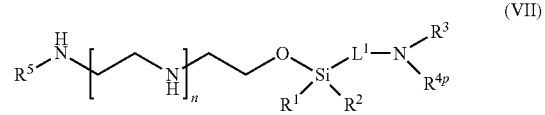

or a salt thereof, wherein
$R^1$ and $R^2$ are independently optionally substituted $C_{1-6}$ alkyl, optionally substituted aryl, or optionally substituted heteroaryl;
$R^3$ is hydrogen or $C_{1-6}$ alkyl;
$R^{4p}$ is a polypeptide, wherein the linkage between $R^{4p}$ and N is with an acyl donor glutamine tag from the polypeptide;
$R^5$ is hydrogen or optionally substituted $C_{1-6}$ alkyl;
n is a number from one to 1200;
$L^1$ is $-(CH_2)_a-$, $-(CH_2)_a-NH-C(O)-NH-(CH_2)_b-$, $-(CH_2)_a-C(O)-NH-(CH_2)_b-$, or $-(CH_2)_a-NH-C(O)-(CH_2)_b-$;
a is a number from one to 20; and
b is a number from one to 20; and
a biologically active molecule.

The present disclosure provides a complex comprising a compound of the formula (X):

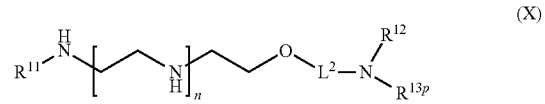

or a salt thereof, wherein
$R^{11}$ is hydrogen or optionally substituted $C_{1-6}$ alkyl;
$R^{12}$ is hydrogen or optionally substituted $C_{1-6}$ alkyl;
$R^{13p}$ is a polypeptide, wherein the linkage between $R^{13p}$ and N is with an acyl donor glutamine tag from the polypeptide;
n is a number from one to 1200;
$L^2$ is —($C_6H_4$)—($CH_2$)$_c$—, —($C_6H_4$)—NH—($CH_2$)$_c$—, —($C_6H_4$)—C(O)—NH—($CH_2$)$_c$—, —($C_6H_4$)—NH—($CH_2CH_2O$)$_d$—$CH_2CH_2$—, or —($C_6H_4$)—C(O)—NH—($CH_2CH_2O$)$_d$—$CH_2CH_2$—;
c is a number from one to 10; and
d is a number from one to 10; and
a biologically active molecule.

The present disclosure provides a complex comprising a compound of the formula (XIII):

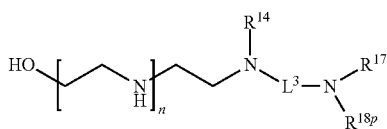

(XIII)

or a salt thereof, wherein
$R^{14}$ is hydrogen, optionally substituted $C_{1-6}$ alkyl, or P

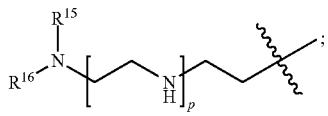

;

$R^{15}$ is hydrogen or optionally substituted $C_{1-6}$ alkyl;
$R^{16}$ is hydrogen or optionally substituted $C_{1-6}$ alkyl;
$R^{17}$ is hydrogen or optionally substituted $C_{1-6}$ alkyl;
$R^{18p}$ is a polypeptide, wherein the linkage between $R^{18p}$ and N is with an acyl donor glutamine tag from the polypeptide;
n is a number from one to 1200;
p is a number from one to 1200;
$L^3$ is —C(O)—($C_6H_4$)—($CH_2$)$_e$— or —C(O)—($CH_2$)$_e$—; and
e is a number from one to 10; and
a biologically active molecule.

Biologically Active Molecule

The complexes described herein comprise a biologically active molecule. As used herein "biologically active molecule" is any molecule that has an effect on a cell, tissue or organism. The biologically active molecule may be of any chemical modality, including, but not limited to, small molecule (e.g., natural product, chemically synthesized drug, steroid, imaging agent, etc.), polypeptide (e.g., short peptide, protein, glycoprotein, Fc-containing polypeptide, Fab-containing polypeptide, antibody, etc.), DNA (e.g., plasmid DNA, cDNA, gene, etc.), RNA (e.g., mRNA, small RNA, including miRNA, ribozyme, etc.), oligonucleotide (e.g. aptamer, antisense oligonucleotide, etc.), oligosaccharide, polysaccharide, lipid, and biocompatible polymer.

The complexes described herein may comprise any number (such as any of 1, 2, 3, 4, 5, or more) of the biologically active molecule. In some embodiments, the complex comprises a single biologically active molecule. In some embodiments, the complex comprises a single species of biologically active molecule. In some embodiments, the complex comprises at least two (such as about any of 2, 3, 4, 5, 6, 7, 8, 9, 10, or more) copies of the biologically active molecule. In some embodiments, the complex comprises more than one (such as about any of 2, 3, 4, 5, or more) species of biologically active molecule. In some embodiments, the molar ratio between the PEI-polypeptide conjugate (e.g., compound of Formulae (IV), (VII), (X) or (XIII))) and the biologically active molecule in the complex is about any one of 1:100, 1:50, 1:20, 1:10, 1:5, 1:3, 1:2, 1:1, 2:1, 3:1, 5:1, 10:1, 20:1, 50:1 or 100:1. In some embodiments, the molar ratio between the PEI-polypeptide conjugate (e.g., compound of Formulae (IV), (VII), (X) or (XIII))) and the biologically active molecule in the complex is any of about 1:100 to about 1:50, about 1:50 to about 1:20, about 1:20 to about 1:10, about 1:10 to about 1:5, about 1:5 to about 1:3, about 1:3 to about 1:2, about 1:2 to about 1:1, about 1:1 to about 2:1, about 2:1 to about 3:1, about 3:1 to about 5:1, about 5:1 to about 10:1, about 10:1 to about 20:1, about 20:1 to about 50:1, about 50:1 to about 100:1, about 100:1 to about 10:1, about 1:10 to about 1:1, about 1:10 to about 10:1, about 1:1 to about 10:1, about 10:1 to about 50:1, about 1:1 to about 100:1, or about 1:100 to about 100:1.

In some embodiments, the biologically active molecule is non-covalently associated with the PEI-polypeptide conjugate (e.g., compound of Formulae (IV), (VII), (X) or (XIII)). In some embodiments, the biologically active molecule carries a negative charge, wherein the negative charge associates with the PEI moiety in the PEI-polypeptide conjugate through electrostatic interactions. For example, nucleic acids (e.g., DNA, RNA and oligonucleotides) are typically negatively charged at physiological conditions, and the PEI-polypeptide conjugate described herein may form a non-covalent complex with nucleic acids through electrostatic interactions. In some embodiments, the ratio of the positive charge on the PEI-polypeptide conjugate to the negative charge on the biologically active molecule is at least about any one of 1, 1.5, 2, 2.5, 3, 4, 5, 10, 20, 50, 100, or more. In some embodiments, the complex has a net positive charge.

Non-covalent complexes may be prepared by mixing the PEI-polypeptide conjugate (e.g., compound of Formulae (IV), (VII), (X) or (XIII)) with the biologically active molecule. In some embodiments, the mixture of the PEI-polypeptide conjugate and the biologically active molecule is further purified, such as by chromatography, or centrifugal filtration.

In some embodiments, the biologically active molecule is covalently associated with the PEI-polypeptide conjugate (e.g., compound of Formulae (IV), (VII), (X) or (XIII)). In some embodiments, the biologically active molecule is incorporated in the polypeptide of the PEI-polypeptide conjugate. Any methods known in the art for conjugating polypeptides to biologically active molecules may be used to prepare the complex, including, but not limited to the chemical and enzymatic conjugation methods described in the "Polypeptide" section. In some embodiments, the biologically active molecule is covalently linked to the polypeptide by polypeptide engineering. For example, wherein the biologically active molecule is a second polypeptide, the second polypeptide and the polypeptide of the PEI-polypeptide conjugate may be genetically fused and expressed recombinantly to provide a fusion polypeptide comprising the biologically active molecule. In some embodiments, the polypeptide is conjugated to the biologically active molecule via a chemical reaction (such as thiol reaction or click chemistry) or an enzyme reaction (such as using a transglutaminase, sortase, or formylglycine generating enzyme). In some embodiments the biologically active molecule is conjugated to a second polypeptide targeting the same cell as the PEI-polypeptide conjugate.

In some embodiments, the complex is prepared by (1) conjugating a biologically active molecule to a polypeptide (such as a targeting polypeptide, for example, an antibody) at a first conjugation site; and (2) conjugating a PEI linker (e.g., any compound of Formulae (I)-(III), (VI), (IX) and (XII)) to the polypeptide at a second conjugation site. In some embodiments, the complex is prepared by (1) conjugating a PEI linker (e.g., any compound of Formulae (I)-(III), (VI), (IX) and (XII)) to a polypeptide at a first conjugation site; and (2) conjugating a biologically active molecule to the polypeptide at a second conjugation site. In some embodiments, one or both conjugation steps further comprise purification of the conjugated product using any methods known in the art, such as chromatography, electrophoresis, or centrifugal filtration.

In some embodiments, the biologically active molecule comprises a nucleic acid. In some embodiments, the biologically active molecule is a nucleic acid. In some embodiments, the nucleic acid is non-covalently associated with the PEI-polypeptide conjugate (e.g., compound of Formulae (IV), (VII), (X) or (XIII)) in the complex. In some embodiments, the nucleic acid is covalently conjugated to the polypeptide. In some embodiments, the nucleic acid comprises at least about any one of 5, 10, 20, 30, 40, 50, 60, 70, 80, 90, 100, 200, 300, 400, 500, 600, 700, 800, 900, 1000, or more nucleotides. In some embodiments, the nucleic acid comprises no more than about any of 100, 200, 300, 400, 500, 600, 700, 800, 900, 1000, 2000, or 3000 nucleotides. In some embodiments, the nucleic acid comprises about any of 10-20, 20-50, 10-50, 50-100, 10-100, 100-200, 200-500, 500-1000, 1000-3000, 10-200, 10-500, 10-1000, or 10-3000 nucleotides. In some embodiments, the nucleic acid comprises conventional DNA and/or RNA nucleotides. In some embodiments, the nucleic acid comprises modified DNA and/or RNA nucleotides. In some embodiments, the nucleic acid comprises nucleobase modification. In some embodiments, the nucleic acid comprises backbone modification. In some embodiments, the nucleic acid is single-stranded. In some embodiments, the nucleic acid is double-stranded. In some embodiments, the nucleic acid is linear. In some embodiments, the nucleic acid is circular. In some embodiments, the nucleic acid is not supercoiled.

In some embodiments, the nucleic acid is a DNA. In some embodiments, the nucleic acid is a DNA. In some embodiments, the DNA is a plasmid. In some embodiments, the DNA is a viral vector. In some embodiments, the DNA encodes one or more protein-coding genes. Exemplary protein-encoding genes include, but are not limited to, toxin, pro-apoptotic gene, immune modulators, cell function modifying proteins (such as chimeric antigen receptors, or CAR), transcription factors, and enzymes (e.g., enzymes that can activate a pro-drug). In some embodiments, the DNA comprises a cell-specific promoter. In some embodiments, the DNA encodes an agent of RNAi, such as miRNA, shRNA, and sgRNA. In some embodiments, the DNA is used for genetic engineering, such as gene knock-in, gene knockdown, gene knockout, gene replacement, and mutagenesis. In some embodiments, the DNA is used in gene therapy. In some embodiments, the DNA is used in a DNA vaccine. In some embodiments, the DNA is an aptamer that specifically binds to a molecular target, such as protein. In some embodiments, the DNA is a catalytically active DNA, such as DNAzyme.

In some embodiments, the nucleic acid is an RNA. In some embodiments, the RNA is an mRNA encoding one or more protein-coding genes. Exemplary protein-encoding genes include, but are not limited to, toxin, pro-apoptotic gene, immune modulators, cell function modifying proteins (such as chimeric antigen receptors, or CAR), transcription factors, and enzymes (e.g., enzymes that can activate a pro-drug). In some embodiments, the RNA is a non-coding RNA. In some embodiments, the RNA is a catalytically active RNA, such as ribozyme. In some embodiments, the RNA is an aptamer that specifically binds to a molecular target, such as protein. In some embodiments, the RNA is an antisense RNA. In some embodiments, the RNA is an agent of RNA interference (RNAi). In some embodiments, the RNA is a microRNA (or mi-RNA). In some embodiments, the RNA is a small silencing RNA (siRNA). In some embodiments, the RNA is a small hairpin RNA (shRNA). In some embodiments, the RNA is a single guide RNA (sgRNA) in the CRISPR system. In some embodiments, the RNA is a long non-coding RNA (lncRNA). In some embodiments, the RNA encodes a virus, such as an attenuated virus. In some embodiments, the RNA is used to modulate endogenous gene expression, such as by gene silencing or epigenetic regulation. In some embodiments, the RNA is used for genetic engineering, such as gene knock-in, gene knockdown, gene knockout, gene replacement, and mutagenesis. In some embodiments, the RNA is used in an RNA vaccine. In some embodiments, the RNA is modified to increase its stability and efficacy. Exemplary modifications to the RNA include, but are not limited to, phosphorothioate backbone modification, 2'-substitutions in the ribose (such as 2'-O-methyl and 2'-fluoro substitutions), LNA, and L-RNA.

In some embodiments, the nucleic acid is a DNA/RNA hybrid.

In some embodiments, the nucleic acid is an oligonucleotide. As used herein, "oligonucleotide" and "oligomer" are used interchangeably to refer to short DNA or RNA molecules, mimetics or derivatives thereof having no more than about 50 nucleotides. In some embodiments, the oligonucleotide is no more than about any of 15, 20, 30, or 40 nucleotides. In some embodiments, the oligonucleotide is an antisense DNA or RNA. In some embodiments, the oligonucleotide is an agent of RNAi. In some embodiments, the oligonucleotide is a probe for detecting intracellular DNA or RNA. In some embodiments, the oligonucleotide further comprises an imaging agent, such as a fluorescent probe. In some embodiments, the oligonucleotide is an immune modulator, such as a CpG oligonucleotide.

In some embodiments, the biologically active molecule comprises a second polypeptide. In some embodiments, the biologically active molecule is a second polypeptide. In some embodiments, the biologically active molecule is a second polypeptide associated with (such as covalently or non-covalently, for example, conjugated to) a second biologically active molecule. In some embodiments, the second polypeptide associates non-covalently with the PEI or the polypeptide. In some embodiments, the second polypeptide associates covalently with the PEI or the polypeptide. In some embodiments, the second polypeptide is fused to the polypeptide of the PEI-polypeptide conjugate in the complex. In some embodiments, the second polypeptide is a short peptide having no more than about any of 10, 20, 30, 40, 50, or 100 amino acids. In some embodiments, the second polypeptide comprises a long amino acid chain having more than 100 amino acids. In some embodiments, the second polypeptide comprises multiple amino acid chains. In some embodiments, the second polypeptide is a ligand of an intracellular molecule. In some embodiments, the second polypeptide is a modulator (such as an inhibitor or activator) of an intracellular molecule. In some embodiments, the second polypeptide is an Fc-containing polypeptide. In some embodiments, the second polypeptide is a Fab-containing polypeptide.

In some embodiments, the biologically active molecule comprises an antibody targeting an intracellular molecule. In some embodiments, the biologically active molecule is an antibody targeting an intracellular molecule. In some embodiments, the antibody is fused to the polypeptide of the PEI-polypeptide conjugate in the complex. In some embodiments, the antibody is a full-length antibody, or an antibody fragment. In some embodiments, the antibody is a monoclonal antibody. In some embodiments, the antibody is a human, humanized, chimeric, or murine antibody. In some embodiments, the antibody is an antagonistic antibody. In some embodiments, the antibody is an agonist antibody.

In some embodiments, the biologically active molecule comprises a toxin polypeptide. In some embodiments, the biologically active molecule is a toxin polypeptide. In some embodiments, the toxin polypeptide is fused to the polypeptide of the PEI-polypeptide conjugate in the complex. Examples of toxin polypeptides include, but are not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, trichothecenes, inhibitor cystine knot (ICK) peptides (e.g., ceratotoxins), and conotoxin (e.g., KIIIA or SmIIa).

In some embodiments, the biologically active molecule comprises a small molecule drug, such as a cytotoxic drug. In some embodiments, the biologically active molecule is a small molecule drug, such as a cytotoxic drug. In some embodiments, the small molecule drug is conjugated to the polypeptide of the PEI-polypeptide conjugate in the complex, for example, as an antibody-drug conjugate (ADC). In some embodiments, the small molecule drug is conjugated to the polypeptide via a spacer arm of various lengths to reduce potential steric hindrance. In some embodiments, the small molecule drug is conjugated to the polypeptide in a site-specific manner. Any of the known therapeutic small molecule drugs targeting intramolecular molecules may be incorporated in the complex. Exemplary small molecule drugs include, but are not limited to, cadaverine, auristatin, geldanamycin, anthracycline, dolastatin, duocarmycin, enediyne, maytansine, taxane, vinca alkaloid, SN-38, tubulysin, hemiasterlin, cytochalasin B, gramicidin D, ethidium bromide, emetine, mitomycin, etoposide, tenoposide, vincristine, vinblastine, colchicine, doxorubicin, daunorubicin, dihydroxy anthracindione, mitoxantrone, mithramycin, actinomycin D, 1-dehydrotestosterone, glucocorticoids, procaine, tetracaine, lidocaine, propranolol, and puromycin and analogs, stereoisomers, isosteres, or homologs thereof.

In some embodiments, the biologically active molecule comprises a therapeutic radioisotope. In some embodiments, the biologically active molecule is a therapeutic radioisotope or a radioisotope label incorporated in the polypeptide of the PEI-polypeptide conjugate in the complex. Examples of therapeutic radioisotopes or radioisotope labels include, but are not limited to, $^{3}$H, $^{14}$C, $^{15}$N, $^{35}$S, $^{18}$F, $^{32}$P, $^{33}$P, $^{64}$Cu, $^{68}$Ga, $^{89}$Zr, $^{90}$Y, $^{99}$Tc, $^{123}$I, $^{124}$I, $^{125}$I, $^{131}$I, $^{111}$In, $^{131}$In, $^{153}$Sm, $^{186}$Re, $^{188}$Re, $^{211}$At, $^{212}$Bi, and $^{153}$Pb.

In some embodiments, the biologically active molecule comprises a label. In some embodiments, the label is a detectable marker incorporated by any of a multitude of methods known in the art. Exemplary labels for the biologically active molecule include, but are not limited to, radioisotopes or radionuclides, fluorescent labels, enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates. In some embodiments, the label is conjugated to the biologically active molecule via a spacer arm of various lengths to reduce potential steric hindrance.

In some embodiments, the biologically active molecule comprises a biocompatible polymer. In some embodiments, the biocompatible polymer improves the biological characteristics of the biologically active molecule, such as to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

In some embodiments, the biologically active molecule comprises a combination of biologically active molecules, such as biologically active molecules with different targets, and/or biologically active molecules of different molecular modalities, including, but not limited to, nucleic acid (such as DNA, RNA, oligonucleotide, etc.), polypeptide (such as antibody, toxin polypeptide, etc.), small molecule (such as cytotoxic drug), therapeutic radioisotope, label, and biocompatible polymer.

IV. Pharmaceutical Compositions

The present disclosure further provides pharmaceutical compositions comprising any one of the PEI-polypeptide conjugates (such as compound of Formula (IV), (VII), (X) or (XIII)), or any one of the complexes (such as complexes comprising compound of Formula (IV), (VII), (X), or (XIII)) as described herein, or a pharmaceutically acceptable salt thereof. The pharmaceutical compositions may further comprise one or more pharmaceutically-acceptable excipients or pharmaceutically-acceptable carrier. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the embodiments are sterile compositions. Pharmaceutical compositions may be prepared using compounding techniques known or that become available to those skilled in the art.

Sterile compositions are also contemplated by the embodiments, including compositions that are in accord with national and local regulations governing such compositions.

The pharmaceutical compositions and compounds described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. Preferably, the compositions are formulated for intravenous, subcutaneous or oral administration.

For oral administration, the compounds may be provided in a solid form, such as a tablet or capsule, or as a solution, emulsion, or suspension. To prepare the oral compositions, the compounds of the embodiments may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions of the embodiments may be formulated for rectal administration as a suppository. For parenteral use, including intravenous, intramuscular, intraperitoneal, intranasal, or subcutaneous routes, the agents of the embodiments may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 0.001 to 1000 µg/kg/minute of agent admixed with a pharmaceutical carrier over a period ranging from several minutes to several days.

For nasal, inhaled, or oral administration, the pharmaceutical compositions of the embodiments may be administered using, for example, a spray formulation also containing a suitable carrier.

For topical applications, the compounds of the embodiments are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the embodiments may utilize a patch formulation to effect transdermal delivery.

V. Methods of Use

The present disclosure further provides methods of using the compounds (such as PEI-polypeptide conjugates, for example, compound of Formula (IV), (VII), (X), or (XIII)), complexes (such as complexes comprising compound of Formula (IV), (VII), (X), or (XIII) and a biologically active molecule), and pharmaceutical compositions described herein.

In some embodiments, there is provided a method of delivering a biologically active molecule to the cytoplasm of a cell, comprising contacting the cell with an effective amount of a PEI-polypeptide conjugate compound or complex as described herein, or a pharmaceutically acceptable salt thereof. Any of the biologically active molecules described above may be delivered using the methods described herein. In some embodiments, the compound or the complex comprises the biologically active molecule. In some embodiments, the biologically active molecule is associated (such as covalently or non-covalently) with the compound or the complex. In some embodiments, the biologically active molecule comprises an Fc-containing polypeptide or a Fab-containing polypeptide (such as an antibody) that specifically binds to an intracellular molecule and/or an extracellular molecule. In some embodiments, the biologically active molecule comprises a toxin polypeptide. In some embodiments, the biologically active molecule comprises a small molecule drug. In some embodiments, the biologically active molecule comprises a therapeutic radioisotope. In some embodiments, the biologically active molecule comprises a charged molecule (such as negatively charged molecule). In some embodiments, the biologically active molecule comprises a nucleic acid, such as a DNA, RNA or oligonucleotide. In some embodiments, the polypeptide in the PEI-polypeptide conjugate of the complex comprises a targeting polypeptide (such as an Fc-containing polypeptide, or Fab-containing polypeptide, for example, an antibody) that specifically binds to a cell surface molecule expressed by the cell. In some embodiments the polypeptide comprises a multispecific antibody or multispecific polypeptide (such as a bispecific antibody or bispecific antibody polypeptide). In some embodiments, the multispecific antibody (such as bispecific antibody) comprises a first binding domain that specifically binds (e.g. directly or indirectly) to an extracellular molecule and a second binding domain that specifically binds (e.g. directly or indirectly) to an intracellular molecule. In some embodiments, the biologically active molecule comprises a second polypeptide. In some embodiments, the biologically active molecule comprises a second polypeptide conjugated to a second biologically active molecule. In some embodiments, the biologically active molecule is released from the endosome and/or lysosome to the cytoplasm. In some embodiments, the biologically active molecule is further delivered to the nucleus of the cell. In some embodiments, the method delivers a single biologically active molecule to the cytoplasm of the cell. In some embodiments, the method delivers more than one (such as any of 2, 3, 4, 5, 6, 7, or more) biologically active molecules to the cytoplasm of the cell.

In some embodiments, there is provided a method of delivering a therapeutic polypeptide that specifically recognizes an intracellular molecule to the cytoplasm of a cell and/or an extracellular molecule, comprising contacting the cell with an effective amount of a PEI-polypeptide conjugate or complex as described herein, or a pharmaceutically acceptable salt thereof. In some embodiments, the polypeptide in the PEI-polypeptide conjugate comprises the therapeutic polypeptide. In some embodiments, the therapeutic polypeptide is fused to the polypeptide in the PEI-polypeptide conjugate. In some embodiments, the polypeptide in the PEI-polypeptide conjugate is the therapeutic polypeptide. In some embodiments, the polypeptide of the PEI-polypeptide conjugate is a targeting polypeptide (such as an Fc-containing polypeptide, or Fab-containing polypeptide, for example, an antibody) that specifically binds (e.g., directly or indirectly) to a cell surface molecule expressed by the targeted cell. In some embodiments, the therapeutic polypeptide is an antibody. In some embodiments, the therapeutic polypeptide is conjugated to a second biologically active molecule. In some embodiments, the therapeutic polypeptide is a toxin polypeptide. In some embodiments, the therapeutic polypeptide is an antibody-drug conjugate (ADC). In some embodiments, the therapeutic polypeptide is a transcription factor. In some embodiments, the therapeutic polypeptide is an enzyme that activates a prodrug. In some embodiments, the therapeutic polypeptide is released from the endosome and/or lysosome to the cytoplasm. In some embodiments, the therapeutic polypeptide is further delivered to the nucleus of the cell. In some embodiments the polypeptide is a multispecific antibody or multispecific polypeptide (such as a bispecific antibody or bispecific antibody polypeptide). In some embodiments, the multispecific antibody (such as bispecific antibody) comprises a first binding domain that specifically binds (e.g. directly or indirectly) to an extracellular molecule and a second binding domain that specifically binds (e.g. directly or indirectly) to an intracellular molecule.

In some embodiments, there is provided a method of delivering an Fc-containing polypeptide or a Fab-containing polypeptide (such as antibody) that specifically recognizes an intracellular molecule to the cytoplasm of a cell and/or and extracellular molecule, comprising contacting the cell with an effective amount of a PEI-polypeptide conjugate compound as described herein, or a pharmaceutically acceptable salt thereof, wherein the polypeptide in the PEI-polypeptide conjugate comprises the Fc-containing polypeptide or the Fab-containing polypeptide (such as antibody). In some embodiments, the polypeptide in the PEI-polypeptide conjugate is fused to the Fc-containing polypeptide or the Fab-containing polypeptide (such as antibody). In some embodiments, the polypeptide in the PEI-polypeptide conjugate is the Fc-containing polypeptide or the Fab-containing polypeptide (such as antibody). In some embodiments, the Fc-containing polypeptide is an antibody that specifically binds (e.g., directly or indirectly) to an intracellular molecule. In some embodiments, the Fc-containing polypeptide is a multispecific antibody (such as a bispecific antibody) comprising a binding domain that specifically binds (e.g., directly or indirectly) to a cell surface molecule expressed on the cell, such as a cell surface receptor or a cell surface antigen. In some embodiments, the Fc-containing polypeptide is a bispecific antibody. In some embodiments, the Fc-containing polypeptide or the Fab-containing polypeptide (such as antibody) is released from the endosome and/or lysosome to the cytoplasm. In some embodiments, the Fc-containing polypeptide or the Fab-containing polypeptide (such as antibody) is further delivered to the nucleus of the cell. In some embodiments the polypeptide is a multispecific antibody or multispecific polypeptide (such as a bispecific antibody or bispecific antibody polypeptide). In some embodiments, the multispecific antibody (such as bispecific antibody) comprises a first binding domain that specifically binds (e.g. directly or indirectly) to an extracellular molecule and a second binding domain that specifically binds (e.g. directly or indirectly) to an intracellular molecule.

In some embodiments, there is provided a method of delivering a nucleic acid encoding a gene to the cytoplasm of a cell, comprising contacting the cell with an effective amount of a complex as described herein, or a pharmaceutically acceptable salt thereof, wherein the complex comprises the nucleic acid as the biologically active molecule. In some embodiments, the nucleic acid is non-covalently associated with the PEI-polypeptide conjugate. In some embodiments, the nucleic acid is a DNA (such as a linear or circular DNA construct). In some embodiments, the nucleic acid further comprises a cell-specific promoter. In some embodiments, the nucleic acid is an RNA (such as mRNA). In some embodiments, the gene is a protein-coding gene. Exemplary protein-coding genes include, but are not limited to, toxin, pro-apoptotic gene, immune modulators, cell function modifying proteins (such as chimeric antigen receptors, or CAR), transcription factors, and enzymes (e.g., enzymes that can activate a pro-drug). In some embodiments, the polypeptide in the PEI-polypeptide conjugate of the complex is a targeting polypeptide (such as an Fc-containing polypeptide, or Fab-containing polypeptide, for example, an antibody) that specifically binds to a cell surface molecule expressed by the cell. In some embodiments, the nucleic acid is released from the endosome and/or lysosome to the cytoplasm. In some embodiments, the nucleic acid is further delivered to the nucleus of the cell.

In some embodiments, there is provided a method of delivering an oligonucleotide to the cytoplasm of a cell, comprising contacting the cell with an effective amount of a complex as described herein, or a pharmaceutically acceptable salt thereof, wherein the complex comprises the oligonucleotide as the biologically active molecule. In some embodiments, the oligonucleotide is non-covalently associated with the PEI-polypeptide conjugate. In some embodiments, the oligonucleotide is a DNA. In some embodiments, the DNA has catalytic activity. In some embodiments, the DNA is an immune modulator, for example, a CpG oligonucleotide. In some embodiments, the oligonucleotide is an antisense oligonucleotide. In some embodiments, the oligonucleotide is an agent of RNAi, including, but not limited to, siRNA, miRNA, shRNA, and sgRNA, or derivatives (such as modified RNA with increased stability) thereof. In some embodiments, the polypeptide in the PEI-polypeptide conjugate of the complex is a targeting polypeptide (such as an Fc-containing polypeptide, or Fab-containing polypeptide, for example, an antibody) that specifically binds to a cell surface molecule expressed by the cell. In some embodiments, the oligonucleotide is released from the endosome and/or lysosome to the cytoplasm. In some embodiments, the oligonucleotide is further delivered to the nucleus of the cell.

The delivery methods described herein can be used for any cell. In some embodiments, the cell is in an in vivo, in vitro, or ex vivo setting. In some embodiments, the cell is in a cell culture. In some embodiments, the cell is a eukaryotic cell, such as a mammalian cell. In some embodiments, the cell is an immune cell, epithelial cell, muscle cell, nerve cell, or a cell derived from a connective tissue, or combinations thereof. In some embodiments, the cell is in a tissue selected from the group consisting of liver, gastrointestinal, pancreatic, kidney, lung, tracheal, vascular, skeletal muscle, cardiac, skin, smooth muscle, connective tissue, corneal, genitourinary, breast, reproductive, endothelial, epithelial, fibroblast, neural, Schwann, adipose, bone, bone marrow, cartilage, pericytes, mesothelial, endocrine, stromal, lymph, blood, endoderm, ectoderm, mesoderm and combinations thereof. In some embodiments, the cell is an immune cell, including, but not limited to, T cells, B cells, NK cells, monocytes, dendritic cells, and macrophages. In some embodiments, the cell is a tumor cell. In some embodiments the cell is a tumor stromal cell.

In some embodiments, there is provided a method of delivering a biologically active molecule to a subject in need thereof, comprising administering to the subject an effective amount of a PEI-polypeptide conjugate or complex as described herein, or a pharmaceutically acceptable salt thereof. In some embodiments, the biologically active molecule comprises an Fc-containing polypeptide or a Fab-containing polypeptide (such as an antibody) that specifically binds to an intracellular molecule. In some embodiments, the biologically active molecule comprises a toxin polypeptide. In some embodiments, the biologically active molecule comprises a small molecule drug. In some embodiments, the biologically active molecule comprises a therapeutic radioisotope. In some embodiments, the biologically active molecule comprises a charged molecule (such as negatively charged molecule). In some embodiments, the biologically active molecule comprises a nucleic acid, such as a DNA, RNA or oligonucleotide. In some embodiments, wherein the polypeptide in the PEI-polypeptide conjugate of the complex is a targeting polypeptide (such as an Fc-containing polypeptide, or Fab-containing polypeptide, for example, an antibody), and the biologically active molecule is delivered in a cell or tissue specific manner. In some embodiments, the method is used for local delivery (such as intratumoral delivery) of the biologically active molecule.

In some embodiments, there is provided a method of treating a disease in a subject in need thereof, comprising administering to the subject an effective amount of a PEI-polypeptide conjugate or complex as described herein, or a pharmaceutically acceptable salt thereof. In some embodiments, the biologically active molecule comprises an Fc-containing polypeptide or a Fab-containing polypeptide (such as an antibody) that specifically binds to an intracellular molecule. In some embodiments, the biologically active molecule comprises a toxin polypeptide. In some embodiments, the biologically active molecule comprises a small molecule drug. In some embodiments, the biologically active molecule comprises a therapeutic radioisotope. In some embodiments, the biologically active molecule comprises a charged molecule (such as negatively charged molecule). In some embodiments, the biologically active molecule comprises a nucleic acid, such as a DNA, RNA or oligonucleotide.

In some embodiments the PEI-polypeptide is administered in combination with a biologically active molecule in a way that the PEI-polypeptide enhances the delivery of the biologically active molecule to its site of action.

The methods described herein may also be used in diagnosis, for example, diagnosis related to cell surface molecules (e.g., receptors). The diagnosis methods can be useful in a variety of fields, including, but not limited to, oncology, metabolic diseases, and infectious diseases.

VI. Kits

The present disclosure further provides a pharmaceutical pack or kit comprising one or more containers comprising any one of the PEI-polypeptide conjugates (such as compound of Formula (IV), (VII), (X) or (XIII)), or any one of the complexes (such as complexes comprising compound of Formula (IV), (VII), (X), or (XIII)) as described herein, or a pharmaceutically acceptable salt thereof useful for the delivery (such as targeted delivery) of a biologically active molecule to the cytoplasm of a cell. The kit can further comprise instructions for use in the delivery (such as targeted delivery) of a biologically active molecule to the cytoplasm a cell.

The present disclosure also provides a pharmaceutical pack or kit comprising one or more containers comprising one or more of the ingredients of the pharmaceutical compositions of the present embodiments. Optionally associated with such container(s) can be a notice in the form prescribed by a governmental agency regulating the manufacture, use or sale of pharmaceuticals or biological products, which notice reflects approval by the agency of manufacture, use or sale for human administration.

VII. Representative Syntheses of Compounds

The present disclosure is also directed to processes and intermediates useful for preparing the subject compounds or pharmaceutically acceptable salts thereof.

Many general references providing commonly known chemical synthetic schemes and conditions useful for synthesizing the disclosed compounds are available (see, e.g., Smith, March's Advanced Organic Chemistry: Reactions, Mechanisms, and Structure, $7^{th}$ edition, Wiley-Interscience, 2013.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," $4^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to formula (I).

Representative syntheses of compounds of the present disclosure are described in schemes below, and the particular examples that follow.

Scheme 1 shows a representative synthesis of the compounds of the embodiments. The methodology is compatible with a wide variety of functionalities.

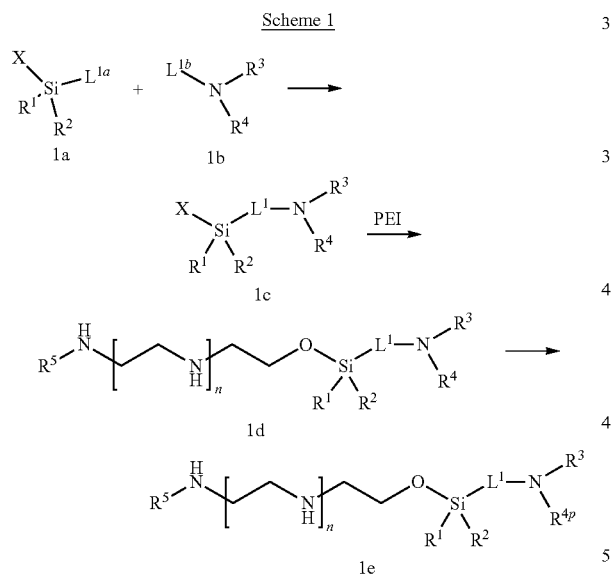

In Scheme 1, $R^1$, $R^2$, $R^3$, $R^4$, $R^{4p}$, $R^5$, $L^1$, and n are as defined herein. Also in Scheme 1, as discussed below, $L^{1a}$ and $L^{1b}$ are precursor moieties to forming the proper bonds and moieties in the formula 1d. Starting materials may be obtained from commercial sources or via well-established synthetic procedures.

With reference to Scheme 1, a coupling reaction between formula 1a and 1b occurs to produce formula 1c. The reaction of moiety $L^{1a}$ and moiety $L^{1b}$ form $L^1$ in formula 1c. In certain instances, moiety $L^{1a}$ is —NCO and moiety $L^{1b}$ is an amino group, such that a urea moiety is formed and the urea moiety is part of $L^1$.

With continued reference to Scheme 1, formula 1c and PEI are coupled to form formula 1d. In some embodiments, PEI is protonated in an acidic environment. In certain instances, PEI is protonated at the amino groups and the hydroxyl group of PEI would react with formula 1c.

With continued reference to Scheme 1, in formula 1d, $R^3$ and $R^4$ can independently be hydrogen, $C_{1-6}$ alkyl, or an amino protecting group. In further reaction, $R^3$ and $R^4$ of formula 1d can be deprotected, if a $C_{1-6}$ alkyl or an amino protecting group is present, to provide a primary amino group. With $R^3$ and $R^4$ of formula 1d both being hydrogen, the compound can be used in a reaction that utilizes primary amino groups selectively. For example, transglutaminase recognizes amino groups for a conjugation reaction with glutamine-containing tags in peptides and proteins. In certain embodiments, a coupling reaction between formula 1d and a polypeptide occurs to produce formula 1e. In certain embodiments, $R^{4p}$ is a polypeptide.

Scheme 2 is another representative synthesis of the compounds of the embodiments. The methodology is compatible with a wide variety of functionalities.

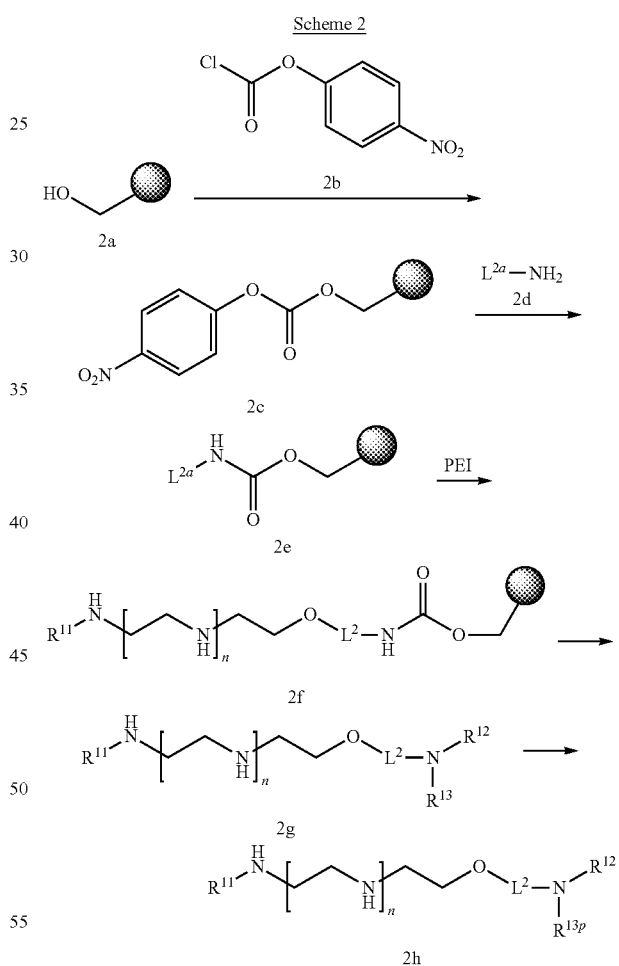

In Scheme 2, $R^{11}$, $R^{12}$, $R^{13}$, $R^{13p}$, $L^2$, and n are as defined herein. Also in Scheme 2, the dark circle is solid phase resin bead. Also in Scheme 2, as discussed below, $L^{2a}$ is a precursor moiety to forming the proper bonds and moieties in the formula 2f. Starting materials may be obtained from commercial sources or via well-established synthetic procedures.

With reference to Scheme 2, formula 2a reacts with formula 2b to form formula 2c, via standard solid phase chemistry procedures. Examples of suitable solid phase resins include Amino-PEGA resin, Wang resin, HMPA-PEGA resin, and Trt Chloride resin. In an example, formula 2c is p-nitrophenyl carbonate on Wang resin. In certain embodiments, in formula 2c, the solid phase resin comprises a functional group that is reactive with an amino group.

With continued reference to Scheme 2, formula 2c is reacted with formula 2d to form formula 2e. In some embodiments, formula 2d comprises an amino group that can react with a solid phase resin comprising a functional group that is reactive with an amino group. As discussed above, $L^{2a}$ is a precursor moiety to forming the proper bonds and moieties in the formula 2f. In some embodiments, one or more reactions can be used to form the $L^{2a}$ moiety.

With continued reference to Scheme 2, reaction of moiety $L^{2a}$ with PEI forms —O-$L^2$-in formula 2f. In some embodiments, PEI is immersed in a liquid to form a solution or suspension. In some embodiments, a Mitsunobu reaction (e.g., with use of DIAD and triphenylphosphine) is used to react a hydroxyl group of PEI with formula 2e. In certain embodiments, formula 2e comprises a phenol group, where a Mitsunobu reaction would form a phenoxy group (e.g., —$C_6H_4$—O—).

With continued reference to Scheme 2, the solid phase resin is then cleaved using standard solid phase chemistry procedures to form formula 2g. In some embodiments, the solid phase resin is Wang resin and suitable cleavage conditions include reaction with trifluoroacetic acid.

With continued reference to Scheme 2, in formula 2g, $R^{12}$ and $R^{13}$ can independently be hydrogen, $C_{1-6}$ alkyl, or an amino protecting group. In further reaction, $R^{12}$ and $R^{13}$ of formula 2g can be deprotected, if a $C_{1-6}$ alkyl or an amino protecting group is present, to provide a primary amino group. With $R^{12}$ and $R^{13}$ of formula 2g both being hydrogen, the compound can be used in a reaction that utilizes primary amino groups selectively. For example, transglutaminase recognizes amino groups for a conjugation reaction with glutamine-containing tags in peptides and proteins. In certain embodiments, a coupling reaction between formula 2g and a polypeptide occurs to produce formula 2h.

Scheme 3 is another representative synthesis of the compounds of the embodiments. The methodology is compatible with a wide variety of functionalities.

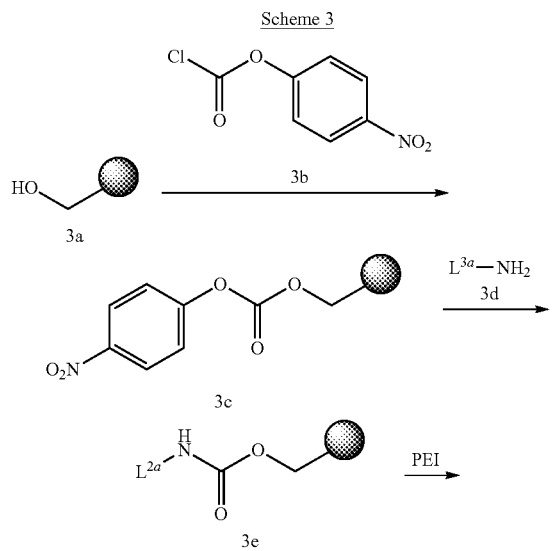

Scheme 3

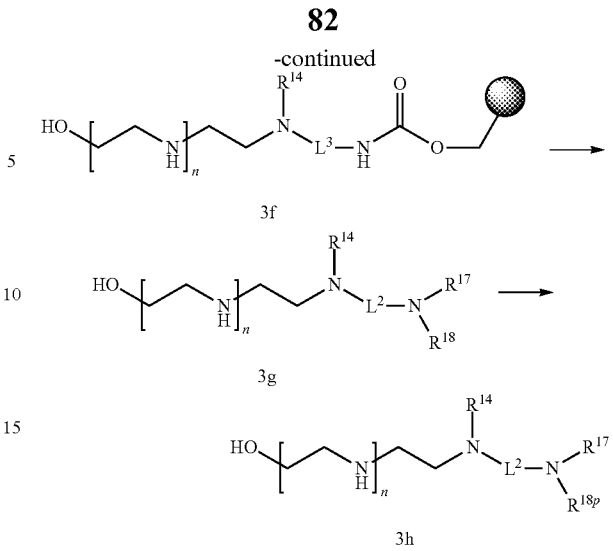

In Scheme 3, $R^{14}$, $R^{17}$, $R^{18}$, $R^{18p}$, $L^3$, and n are as defined herein. Also in Scheme 3, the dark circle is solid phase resin bead. Also in Scheme 3, as discussed below, $L^{3a}$ is a precursor moiety to forming the proper bonds and moieties in the formula 3f. Starting materials may be obtained from commercial sources or via well-established synthetic procedures.

With reference to Scheme 3, formula 3a reacts with formula 3b to form formula 3c, via standard solid phase chemistry procedures. Examples of suitable solid phase resins include Amino-PEGA resin, Wang resin, HMPA-PEGA resin, and Trt Chloride resin. In an example, formula 3c is p-nitrophenyl carbonate on Wang resin. In certain embodiments, in formula 3c, the solid phase resin comprises a functional group that is reactive with an amino group.

With continued reference to Scheme 3, formula 3c is reacted with formula 3d to form formula 3e. In some embodiments, formula 3d comprises an amino group that can react with a solid phase resin comprising a functional group that is reactive with an amino group. As discussed above, $L^{3a}$ is a precursor moiety to forming the proper bonds and moieties in the formula 3f. In some embodiments, one or more reactions can be used to form the $L^{3a}$ moiety. In some embodiments, a reaction is used to provide a good leaving group in the $L^{3a}$ moiety for a subsequent reaction.

With continued reference to Scheme 3, reaction of formula 3e with PEI forms formula 3f. The reaction of PEI with the moiety $L^{3a}$ forms —$NR^{14}$-$L^3$- in formula 3f. Since any secondary amino group in PEI can react with the moiety $L^{3a}$ of formula 3e, the connection of the moiety $L^{3a}$ of formula 3e can occur at the terminus of PEI or in an interior repeat unit of PEI. As discussed above, in some embodiments, $L^{3a}$ moiety comprises a good leaving group for a subsequent reaction with a secondary amino group of PEI.

With continued reference to Scheme 3, the solid phase resin is then cleaved using standard solid phase chemistry procedures to form formula 3g. In some embodiments, the solid phase resin is Wang resin and suitable cleavage conditions include reaction with trifluoroacetic acid.

With continued reference to Scheme 3, in formula 3g, $R^{17}$ and $R^{13}$ can independently be hydrogen, $C_{1-6}$ alkyl, or an amino protecting group. In further reaction, $R^{12}$ and $R^{18}$ of formula 3g can be deprotected, if a $C_{1-6}$ alkyl or an amino protecting group is present, to provide a primary amino group. With $R^{17}$ and $R^{18}$ of formula 3g both being hydrogen, the compound can be used in a reaction that utilizes primary amino groups selectively. For example, transglutaminase recognizes amino groups for a conjugation reaction with glutamine-containing tags in peptides and proteins. In certain embodiments, a coupling reaction between formula 3g and a polypeptide occurs to produce formula 3h.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

The invention can be further understood by reference to the following examples, which are provided by way of illustration and are not meant to be limiting.

Example 1. Synthesis of Modified PEI with Silyl Derivative (Compound 6a-c)

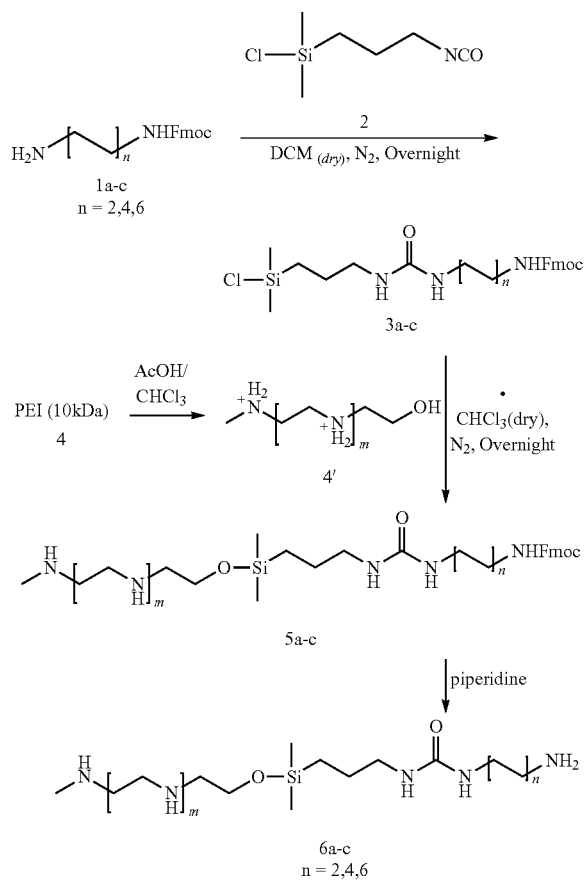

Reagents:
1a: N-Fmoc-ethylenediamine hydrobromide: Sigma Aldrich, 47542-500MG, CAS Number 352351-55-4.
1b: N-Fmoc-1,4-butanediamine hydrobromide: Sigma Aldrich, 47541-1G, CAS Number 352235-99-5
1c: N-Fmoc-1,6-hexanediamine hydrobromide: Sigma Aldrich, 47543-1G, CAS Number 352351-56-5.
2: 3-Isocyanatopropyldimethylchlorosilane: Fluorochem, MFCD00013886-10g, CAS Number 17070-70-1.
4: PEI: Polyethyleneimine, linear, average Mn 10,000, PDI≤1.2. 765090 Aldrich
Piperidine, 104094 Sigma-Aldrich CAS Number 110-89-4
Solvent: Dichloromethane: Sigma Aldrich, 270997-250ML, CAS Number 75-09-2.
Resin: Amberlyst® A21 free base: Sigma Aldrich, 216410-250G.
Experimental Procedure
Step 1: Preparation of the Chlorosilane-Amino-Fmoc Reagent (3c)

In a 20 mL flask, compound 1c (as hydrobromide salt, 10 mg, 0.024 mmol, 1 eq.) was dissolved in anhydrous chloroform (5 mL). Amberlyst A-21 free-base resin (500 mg) was added and the suspension stirred for 30 min to release a free amine. The suspension was filtered to give a solution (5 mL), the solid was washed with 7 mL chloroform, and the combined solution (5+7 mL) was added to a 10 mL flask containing compound 2 (4.02 mg, 0.023 mmol, 0.96 eq.). The system was kept under nitrogen atmosphere, and let react overnight (MIX-1).

Step 2: Preparation of 5c by Coupling (3c) with PEI (2)

In a 50 mL flask, PEI (4) (50 mg, 0.005 mmol, 1 eq, previously dissolved in water and lyophilized) was suspended in 10 mL anhydrous chloroform with vigorous stirring to get a finely dispersed suspension. Acetic acid (75 µL, 1.185 mmol, 237 eq.) was added to protonate the amino groups of PEI. The suspension became a translucid solution. Next, the reaction mixture from Step 1 (MIX-1) was added under nitrogen atmosphere, and the flask that contained MIX-1 was washed with 3 mL chloroform which was added to the reaction mixture. The resulting reaction mixture was left overnight at room temperature under nitrogen atmosphere.

Finally, the reaction product 5c was precipitated. For that, ethyl ether (15 mL) was added to the reaction mixture. After 30 min with stirring, the solid was separated by centrifugation (4° C., 10000 rpm, 10 min). The supernatant was discarded, and the solid washed twice with ethyl ether (resuspension in ethyl ether, centrifugation, and the supernatant discarded). The resulting solid was dried under vacuum to give a white powder (compound 5c).

Step 3: Preparation of 6c by Release of Fmoc.

Compound 5c was treated with 20% v/v piperidine in chloroform (1 mL piperidine in 5 mL chloroform) for 30 min at room temperature with stirring. After evaporation of the solvent under vacuum, the solid was dried under vacuum. FINAL PRODUCT 6c stored at 4° C. Compound 6c (n=6) is also referred herein as RF8.
Preparation of 6a and 6b Compound 6a (n=2, also referred herein as RF6) and Compound 6b (n=4, also referred herein as RF7) were synthesized with the same scheme.

Example 2. Synthesis of Modified PEI with Ether Linkage Solid Phase Resin (Compound 7751)

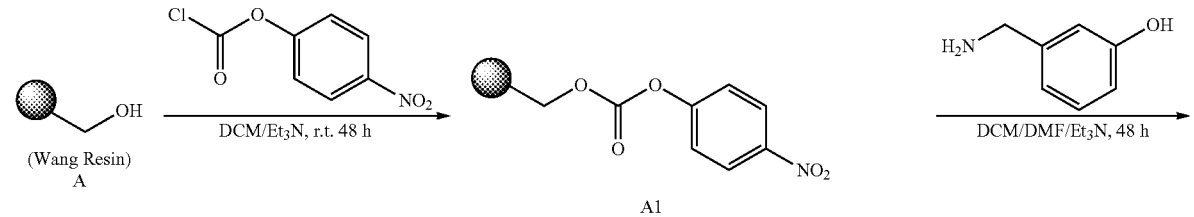

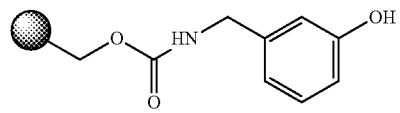

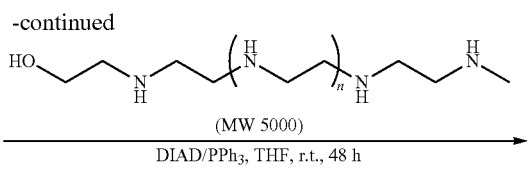

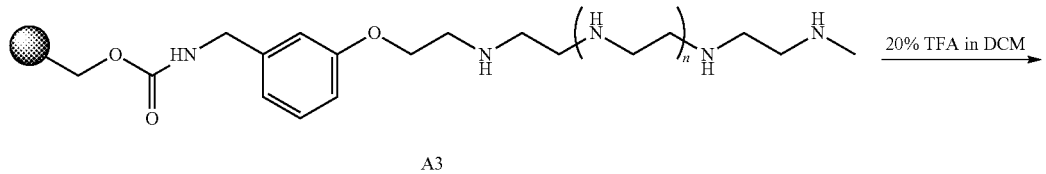

A3

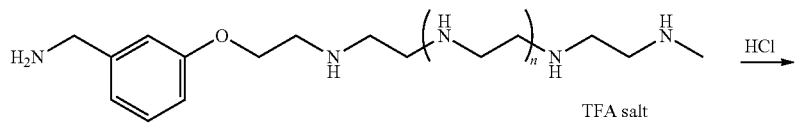

A4

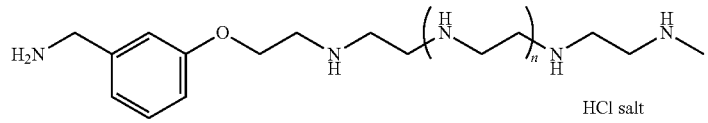

AB7751

Preparation of A1

Wang resin (loading 0.31 mmol/g, 1 g, 0.31 mmol, 1 eq) in dichloromethane (DCM, 6 mL) was shaken at room temperature for 1 h, and filtered. To the resin suspended in DCM (6 mL) was added N-methyl morpholine (136 µL, 1.24 mmol, 4 eq). The mixture was cooled on ice bath to 0° C., and 4-nitrophenyl chloroformate (188 mg, 0.93 mmol, 3 eq) was added. The resin mixture was shaken at room temperature for 48 h. It was washed with DCM until it is clean (substantially no starting material or reagents can be detected in the washing solvent). The resin was dried on vacuum.

Small amount of dried resin (50 mg) was treated with 20% TFA in d DCM (1.0 mL) at room temperature for 1 h. The resin was filtered and washed with dichloromethane and methanol. The washing solution was concentrated to dryness and checked by $^1$H NMR. The spectra showed the signal of 4-nitrophenol.

Using the same method, large scale of A1 was prepared.

Preparation of A2

To the resin A1 (2 g, 0.62 mmol, 1.0 eq) in a mixed solvent (DCM/DMF, 1:1, 5 mL) at room temperature were added 3-(aminomethyl)phenol (763 mg, 6.2 mmol, 10 eq) and triethylamine (863 µL, 6.2 mmol, 10 eq). The mixture was shaken at room temperature for 48 h, and washed with DCM, MeOH and DCM until the washing solution was clean. The resin was dried in vacuum to give product A2.

Small amount of A2 (50 mg) was treated with 20% TFA in DCM at room temperature for 1 h. The filtered solution was concentrated and checked with $^1$HNMR, which confirmed that 3-(aminomethyl) phenol was coupled on the resin.

Preparation of AB7751

To a mixture of resin A2 (100 mg, 0.031 mmol, 1 eq) in THF (1 mL) was added PEI (Aldrich, MW5000, 300 mg, 0.06 mmol, 2 eq, dissolved in 10 mL of THF) and triphenylphosphine (16 mg, 0.06 mmol, 2 eq). The mixture was cooled in an ice bath and diisopropyl azodicarboxylate (DIAD, 13 mg, 0.06 mmol, 2 eq) was added. The suspension (PEI could not fully dissolved) was shaken at room temperature for 48 h, and washed with MeOH, DMF, MeOH and DCM until the washing solution was clean. The resin was dried in vacuum to give A3.

A3 was treated with 20% TFA in DCM (5 mL) for 1 h. It was filtered and washed with MeOH and DCM. The filtrate was concentrated to dryness to give product A4 as TFA salt (37 mg).

The reaction was repeated again with 200 mg of A2 and about 70 mg of A4 obtained. The two batches of A4 were combined and dissolved in 1N HCl (2 mL) and concentrated to dryness. This process was repeated three times to convert A4 to HCl salt to give final product AB7751 (70 mg).

$^1$H NMR (300 MHz, CD$_3$OD) δ 7.21 (t, 1H, Ar—H), 6.79 (m, 3H, Ar—H), 3.98 (s, 2H, Ar—H), 3.33 (br s, n-(CH$_2$—CH$_2$)—, PEI-H).

Example 3. Synthesis of Modified PEI with Ether Linkage Solid Phase Resin (Compound 7769)

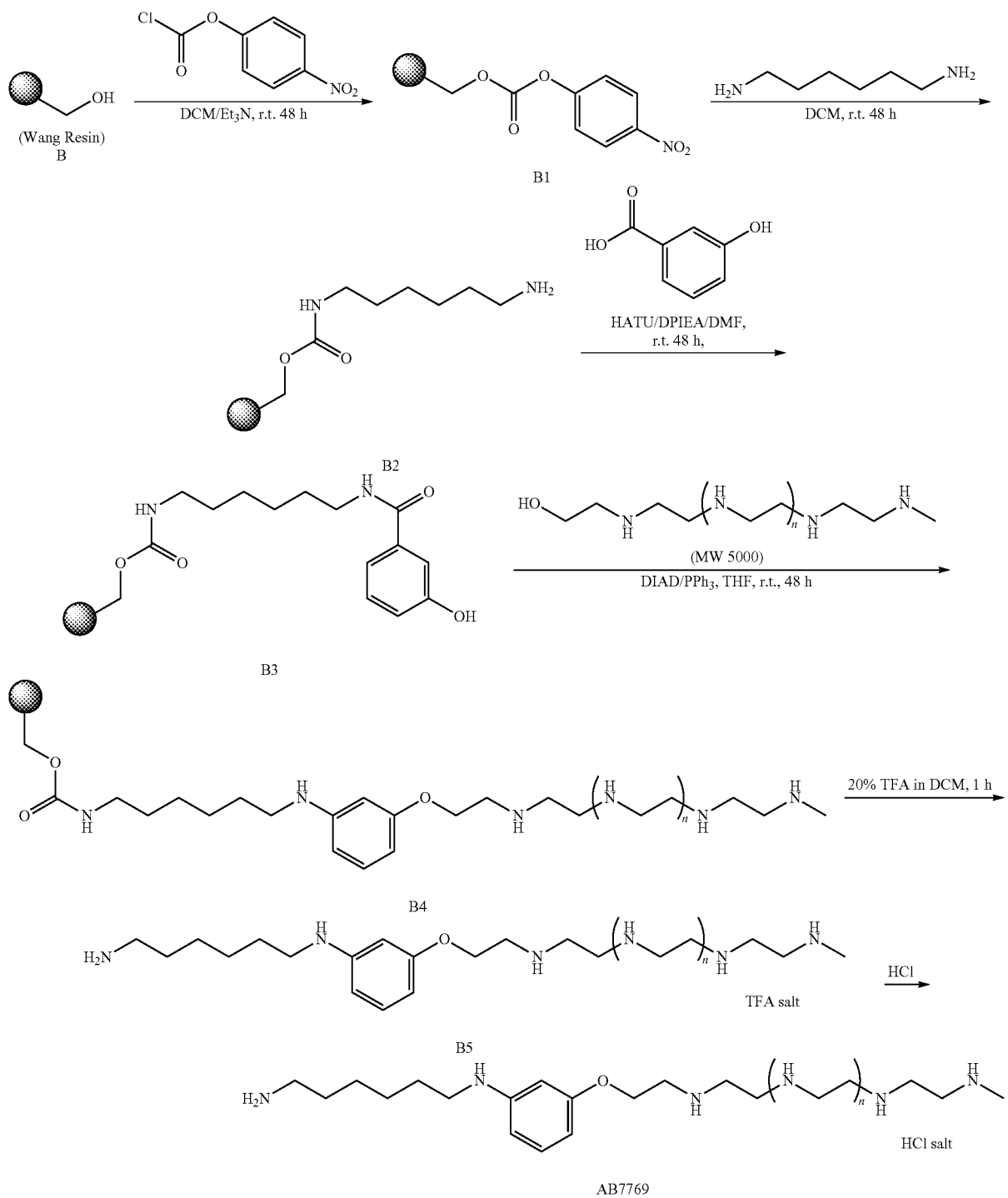

Preparation of B1

The preparation of B1 is the same as the preparation of A1.

Preparation of B2

To a mixture of resin B1 (2 g, 0.62 mmol, 1.0 eq) in dichloromethane (DCM, 6 mL) at room temperature was added 1,6-hexanediamine (721 mg, 6.2 mmol, 10 eq). The mixture was shaken at room temperature for 48 h, and washed with DCM, methanol (MeOH) and DCM until the washing solution was clean. The resin was dried on vacuum to give product B2.

Small amount of B2 (50 mg) was treated with 20% trifluoroacetic acid (TFA) in DCM at room temperature for 1 h. The filtrate was concentrated and checked with ¹HNMR, which confirmed that 1,6-hexanediamine was coupled on the resin.

Preparation of B3

To the resin B2 (2 g, 0.62 mmol) in N,N-dimethylformamide (DMF, 10 mL) at room temperature was added 3-hydroxybenzoic acid (428 mg, 3.1 mmol, 5 eq), HATU (1.18 g, 3.1 mmol, 5 eq) and diisopropylethylamine (DIPEA, 0.51 mL, 3.1 mmol, 5 eq). The mixture was shaken at room temperature for 50 h, and washed with DMF, H$_2$O, MeOH and DCM until the washing solution was clean. The resin was dried on vacuum to give product B3.

Small amount of B3 (50 mg) was treated with 20% TFA in DCM at room temperature for 1 h. The filtered solution was concentrated and checked with 1HNMR and LC-MS, which confirmed that 3-hydroxybenzoic acid was coupled on the amine.

Preparation of AB7769

To a mixture of resin B3 (200 mg, 0.062 mmol, 1 eq) in tetrahydrofuran (THF, 5 mL) was added PEI (Aldrich-764582, MW5000, 300 mg, 0.06 mmol, 2 eq) in THF (3 mL) and triphenylphosphine (16 mg, 0.06 mmol, 2 eq). The mixture was cooled in an ice bath and DIAD (13 mg, 0.06 mmol, 2 eq) was added. The suspension (PEI could not be fully dissolved) was shaken at room temperature for 48 h, and washed with MeOH, and DCM until the washing solution was clean. The resin was dried on vacuum to give B4. B4 was treated with 20% TFA in DCM (5 mL) for 1 h. It was filtered and washed with MeOH and DCM. The filtrate was concentrated to dryness to give crude product B5 as TFA salt (150 mg).

The reaction was repeated again with same scale and about 120 mg of B5 obtained. The combined B5 was purified by Sephadex-LH-20 (washing with methanol) to give pure B5 as TFA salt. The TFA salt of B5 was dissolved in 1N HCl (2 mL) and concentrated to dryness. This process was repeated three times to convert B5 to AB7769 as HCl salt (65 mg).

¹H NMR (300 MHz, CD$_3$OD) δ 8.08 (s, 1H, Ar—H), 7.18-7.3 (m, 3H, Ar—H), 3.63 (m, 2H), 3.40 (s, n-(CH$_2$—CH$_2$)—, PEI-H), 3.29 (m, 4H), 2.83 (m, 2H), 1.18 (m, 4H).

Example 4. Synthesis of Modified PEI with Ether Linkage Solid Phase Resin (Compound AB7776)

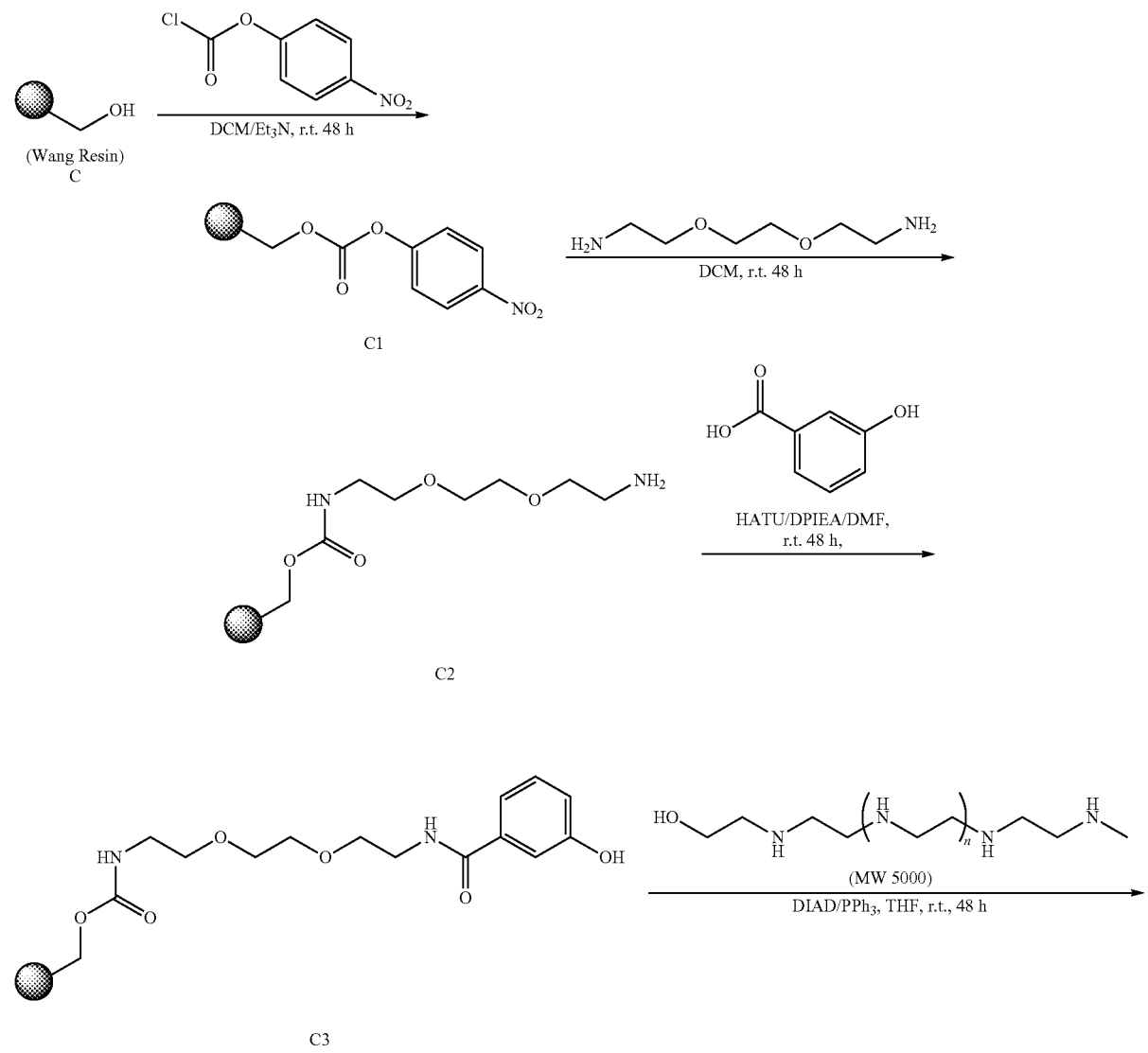

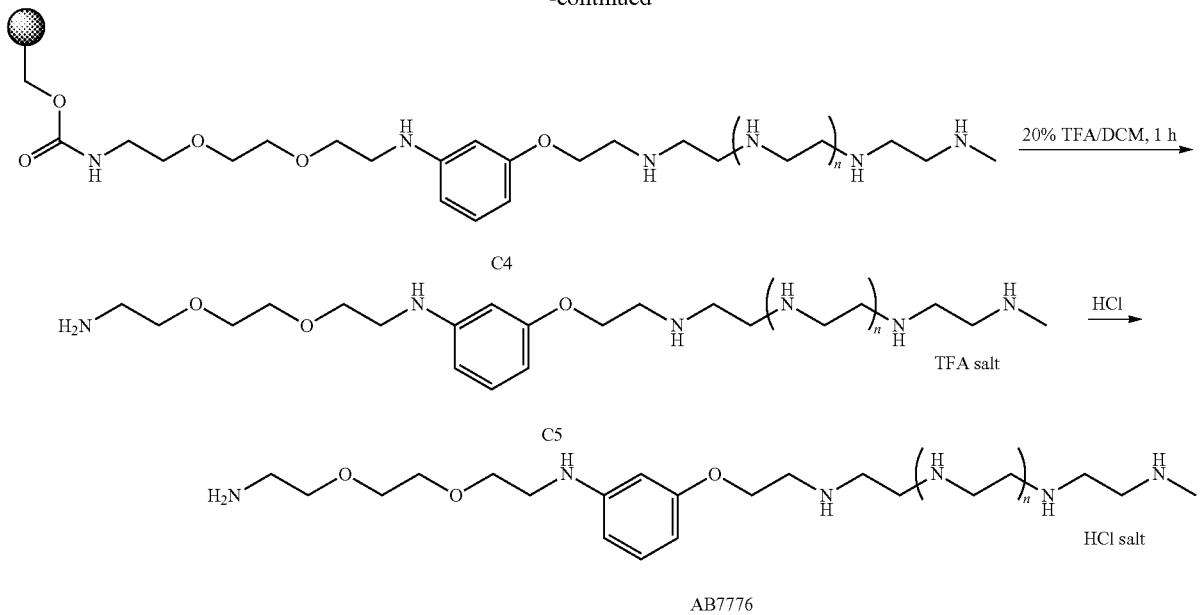

Preparation of C1

The preparation of C1 is the same as the preparation of A1

Preparation of C2

To a mixture of resin C1 (1.5 g, 0.47 mmol, 1 eq) in dichloromethane (DCM, 8 mL) at room temperature was added 2, 2'-(ethylenedioxy)bis-ethylamine (688 μL, 4.7 mmol, 10 eq). The mixture was shaken at room temperature for 48 h, and washed with MeOH and DCM until the washing solution was clean. The resin was dried on vacuum to give product C2.

Small amount of C2 (50 mg) was treated with 20% TFA in DCM at room temperature for 1 h. The filtered solution was concentrated and checked with $^1$HNMR, which confirmed that 2, 2'-(ethylenedioxy)bis-ethylamine was coupled on the resin.

Preparation of C3

To the resin C2 (1.5 g, 0.47 mmol) in DMF (5 mL) at room temperature was added 3-hydroxybenzoic acid (321 mg, 2.33 mmol, 5 eq), 1-[bis(dimethylamino)methylene]-1H-1,2,3-triazolo[4,5-b]pyridinium 3-oxid hexafluorophosphate (HATU, 886 mg, 2.33 mmol, 5 eq) and DIPEA (0.384 mL, 2.33 mmol, 5 eq). The mixture was shaken at room temperature for 2 days, and washed with MeOH, H$_2$O, MeOH and DCM until the washing solution was clean. The resin was dried in vacuum to give product C3.

Small amount of C3 (50 mg) was treated with 20% TFA in DCM at room temperature for 1 h. The filtered solution was concentrated and checked with $^1$H NMR and LC-MS, which confirmed that 3-hydroxybenzoic acid was coupled on the resin.

Preparation of AB7776

To a mixture of resin C3 (200 mg, 0.062 mmol, 1 eq) in THF (5 mL) was added PEI (MW 5000, 750 mg, 0.15 mmol, 2.4 eq, partially dissolved in 5 mL of THF) and triphenylphosphine (49 mg, 0.186 mmol, 3 eq). The mixture was cooled in an ice bath and DIAD (38 mg, 0.186 mmol, 3 eq) was added. The suspension was shaken at room temperature for 3 days, and washed with MeOH, and DCM until the washing solution was clean. The resin was dried on vacuum to give C4. Resin C4 was treated with 20% TFA in DCM (5 mL) for 1 h. It was filtered and washed with MeOH and DCM. The filtrate was concentrated to dryness to give crude product C5 (TFA salt, 95 mg). The TFA salt was purified by Sephadex-LH-20 (MeOH) to give pure C5. This TFA salt was dissolved in 1N HCl (2 mL) and concentrated to dryness. This process was repeated three times to convert C5 to final product AB7776 as HCl salt (26 mg).

$^1$H NMR (300 MHz, CD$_3$OD) δ 8.08 (s, 1H, Ar—H), 7.18-7.3 (m, 3H, Ar—H), 3.56-3.63 (m), 3.45 (s, n-(CH$_2$—CH$_2$)—, PEI-H).

Example 5. Synthesis of Modified PEI with Amino Linkage Solid Phase Resin (Compound AB7752)

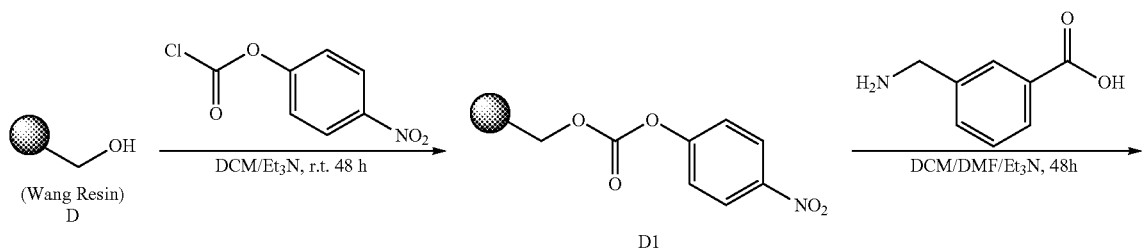

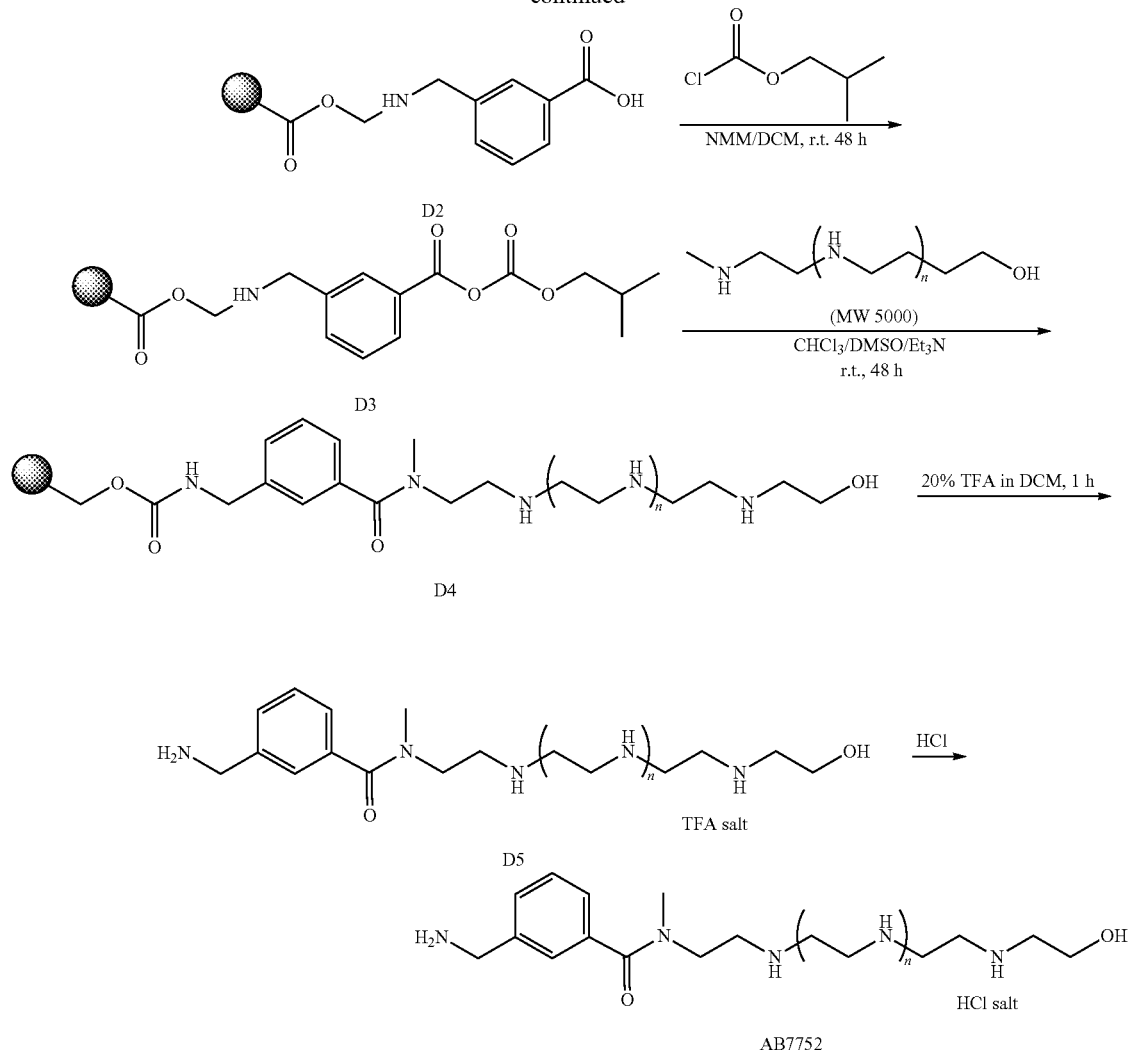

Preparation of D1

The preparation of D1 is the same as the preparation of A1.

Preparation of D2

To the resin D1 (2 g, 0.62 mmol, 1 eq) in a mixed solvent of dichloromethane and DMF (1:1, 8 mL) at room temperature was added 3-(aminomethyl)benzoic acid (1.16 g, 6.2 mmol, 10 eq) and triethylamine (1.73 mL, 12.4 mmol, 20 eq). The mixture was shaken at room temperature for 48 h, and washed with MeOH, H$_2$O, MeOH and DCM until the washing solution was clean. The resin was dried on vacuum to give product D2.

Small amount of D2 (50 mg) was treated with 20% TFA in DCM at room temperature for 1 h. The filtrate was concentrated and checked with $^1$HNMR, which confirmed that 3-(aminomethyl)benzoic acid was coupled on the resin.

Preparation of D3

To the resin D2 (800 mg, 0.248 mmol, 1 eq) in DCM (5 mL) at room temperature was added N-methylmorpholine (408 μL, 3.72 mmol, 15 eq) and isobutyl chloroformate (323 μL, 2.48 mmol, 10 eq). The mixture was shaken at room temperature for 3 days, and washed with DCM until the washing solution was clean. The resin was dried on vacuum to give product D3.

Preparation of AB7752

To a mixture of resin D3 (100 mg, 0.031 mmol, 1 eq) in chloroform (2 mL) was added PEI (MW 5000, 233 mg, 0.0465 mmol, 1.5 eq, partially dissolved in 5 mL of chloroform and dimethyl sulfoxide, 1:1) and triethylamine (22 μL, 0.155 mmol, 5 eq). The mixture (still a suspension, PEI could not be fully dissolved) was shaken at room temperature for 2 days, and washed with MeOH, and DCM until the washing solution was clean. The resin was dried on vacuum to give D4. The resin D4 was treated with 20% TFA in DCM (5 mL) for 1 h. It was filtered and washed with MeOH and DCM. The filtrate was concentrated to dryness to give crude product D5 as TFA salt (44 mg).

The reaction was repeated again with 540 mg of D3 and about 160 mg of D5 obtained. The two batches of crude D5 (TFA salts) were combined and purified by Sephadex-LH-20 (MeOH) to give D5 (TFA salt, 36 mg). This TFA salt was dissolved in 1N HCl (2 mL) and concentrated to dryness. This process was repeated three times to convert D5 to HCl salt to give final product AB7752 (HCl salt, 26 mg).

$^1$H NMR (300 MHz, CD$_3$OD) δ 7.40-7.8 (m, 4H, Ar—H), 4.12 (s, 2H), 3.23 (s, n-(CH$_2$—CH$_2$)—, PEI-H).

Example 6. Synthesis of Modified PEI with Amino Linkage Solid Phase Resin (Compound AB7753)

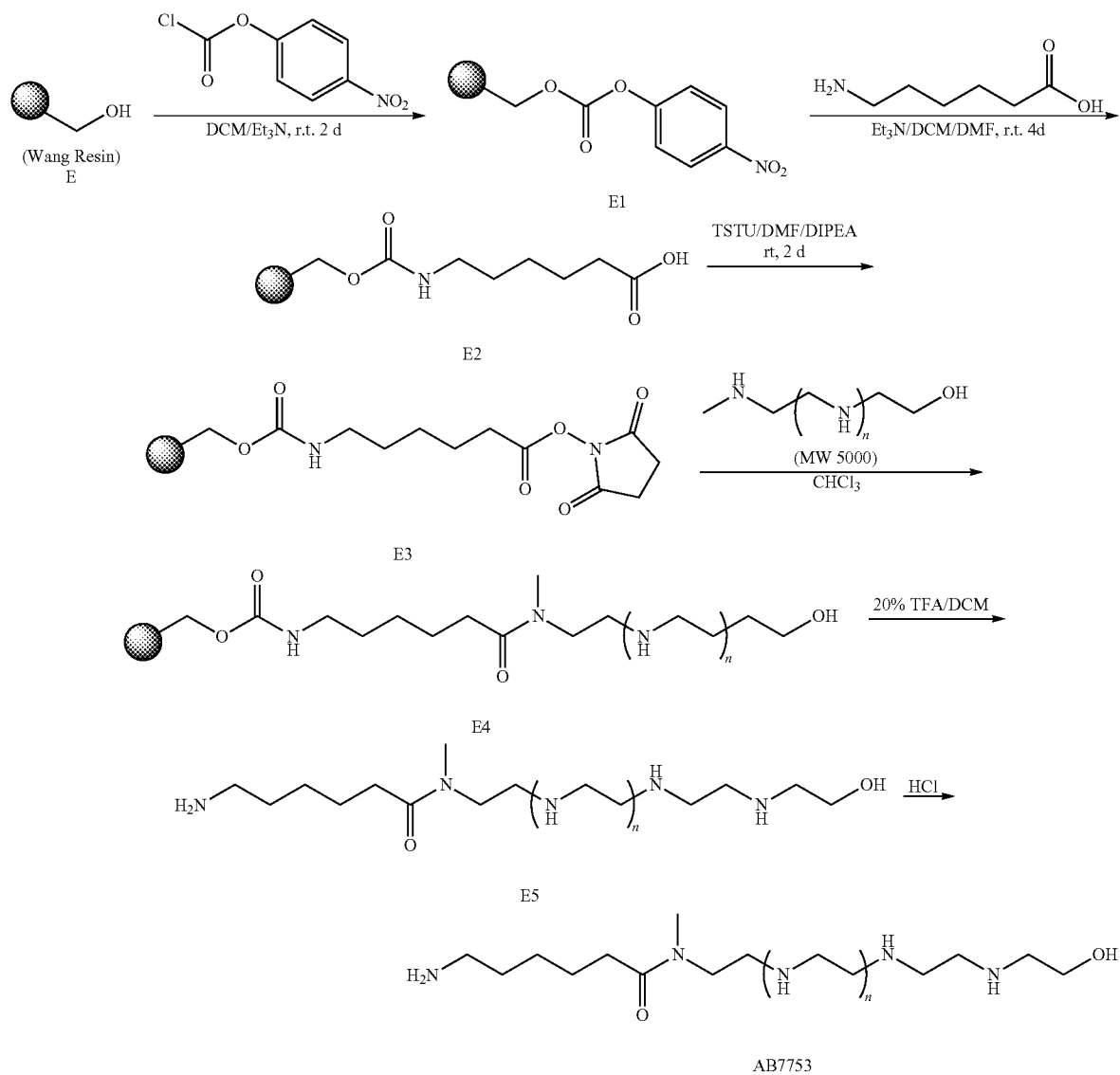

Preparation of E1

Preparation of E1 is the same as preparation of A1.

Preparation of E2

To the resin E1 (2 g, 0.62 mmol, 1.0 eq) in a mixed solvent of dichloromethane and DMF (8 mL, 1:1) at room temperature was added 6-Amino-hexanoic acid (812 mg, 6.2 mmol, 10 eq) and triethylamine (862 μL, 6.2 mmol, 10 eq). The mixture was shaken at room temperature for 4 days, and washed with DMF, H₂O, MeOH and DCM until the washing solution was clean. The resin was dried on vacuum to give product E2.

Small amount of E2 (50 mg) was treated with 20% TFA in DCM at room temperature for 1 h. The filtered solution was concentrated and checked with $^1$HNMR which confirmed that 6-Amino-hexanoic acid was coupled on the resin.

Preparation of E3

To the resin E2 (500 mg, 0.15 mmol, 1 eq) in DMF (5 mL) at room temperature was added N,N,N',N'-tetramethyl-O—(N-succinimidyl)uronium tetrafluoroborate (TSTU, 451 mg, 1.5 mmol, 10 eq) and diisopropylethylamine (371 μL, 2.25 mmol, 15 eq). The mixture was shaken at room temperature for 48 h, and washed with DCM until the washing solution was clean. The resin was dried on vacuum to give product E3.

Preparation of AB7753

To a mixture of resin E3 (100 mg, 0.031 mmol, 1 eq) in chloroform (2 mL) was added PEI (MW 5000, 310 mg, 0.062 mmol, 2.0 eq, partially dissolved in 5 mL of DMF) and triethylamine (22 μL, 0.155 mmol, 5 eq). The mixture (still a suspension, PEI could not fully dissolved) was shaken at room temperature for 48 h (it was heated several times during this process to make PEI more dissolved) and washed with MeOH, DMF and DCM until the washing solution was clean. The resin was dried on vacuum to give E4. E4 was treated with 20% TFA in DCM (5 mL) for 1 h. It was filtered and washed with MeOH and DCM. The filtrate was concentrated to dryness to give crude product E5 as TFA salt (25 mg).

The reaction was repeated several times to get more E5. All batches of E5 were combined and purified by Sephadex-LH-20 (MeOH) to give pure E5 (56 mg) as TFA salt. This TFA salt was dissolved in 1N HCl (2 mL) and concentrated to dry. This process was repeated three times give final product AB7753 (40 mg)

$^1$H NMR (300 MHz, CD$_3$OD) δ 3.42 (s, n-(CH$_2$—CH$_2$)—, PEI-H), 2.8-3.2 (m, 4H), 1.45 (m, 4H), 1.2 (m, 2H).

Example 7. Mutagenesis and Preparation of Erb001B1

Cetuximab (also known as ERBITUX®) is a monoclonal chimeric mouse/human antibody against the epidermal growth factor receptor (EGFR). A variant of cetuximab with an engineered acyl donor glutamine tag can be covalently conjugated to the PEI linkers described in the present application via a transglutamination reaction. Among many applications, anti-EGFR Mabs conjugated to PEI can be used to specifically deliver nucleic acids to cancer cells that have high expression levels of EGFR.

This example describes mutagenesis and preparation of an engineered version of cetuximab, which is referred to hereinafter as Erb001B1. All human IgG antibodies contain an acceptor glutamine in position 295 (Q295 of the heavy chain) that is not accessible to a transglutaminaiton reaction in wild type, normally glycosylated antibodies due to steric hindrance of carbohydrate. This residue can be made accessible by preventing the glycosylation of the adjacent N297 (kabat). To make the Q295 residue accessible to transglutaminase reaction, Erbitux heavy chain was mutated by site directed mutagenesis at position N297 to A to generate the antibody Erb001B1 that has an acyl donor glutamine tag accessible in position 295. The amino acid sequence of the heavy chain of cetuximab is shown below in SEQ ID NO: 7 and the glutamine acceptor highlighted in bold and the N mutated to A (underlined). The amino acid sequence of the light chain of cetuximab is shown below in SEQ ID NO: 8.

```
Cetuximab wildtype heavy chain
                                           (SEQ ID NO: 7)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSP

GK

Cetuximab wildtype light chain
                                           (SEQ ID NO: 8)
DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGA
```

Mutagenesis of Cetuximab

Plasmid pcDNA 3.1 Erbitux hG1 encodes for the wildtype heavy chain of cetuximab, and plasmid pcDNA 3.1 Erbitux hkappa encodes for the wildtype light chain of cetuximab. Plasmids were amplified in XL1-BLUE® E. coli and purified using the GENEJET® Plasmid Miniprep Kit (Thermo Fisher Scientific) according to the manufacturer's instructions.

Site-directed mutagenesis was performed on the pcDNA 3.1 Erbitux hG1 plasmid to introduce an N297A mutation to the wildtype heavy chain of cetuximab using the following PCR condition. 3 ng of pcDNA 3.1 Erbitux hG1 was mixed with 1 μM of primer 5P hIgG-ChmutNA (5'-*GCCAGCACGTACCGTGTGGTCAGCGTC-3', SEQ ID NO: 22, wherein *denotes phosphorylation at the 5' end of this nucleotide) that introduces N297A mutation, 1 μM of primer 3 hIgG-CHmutNA (5'-GTACTGCTCCTCCCGCGGCTTTG-3', SEQ ID NO: 23), 0.6 Units of PHUSION® polymerase (Fynnzimes), and 10 μL of 5×HF buffer. Sterile MILLIQ® water was added to the mixture to reach a total volume of 50 μL. The mixture was heated for 2 minutes at 95° C. in a PCR machine before carrying out the first PCR cycle. Each PCR cycle included 20 seconds incubation at 95° C., followed by 30 seconds incubation at 70° C., and 2 minutes incubation at 72° C. The PCR cycle was repeated for 35 times. After the PCR cycles, a final extension of the PCR products was performed by incubating the samples at 72° C. for 5 minutes. The product of this PCR was separated on a 0.6% agarose gel by electrophoresis, purified using the NUCLEOSPIN® Gel and PCR Clean-up kit (Macherey Nagel), and eluted in 20 μL of elution buffer. The PCR product was then circularized using T4 DNA ligase (Roche) and amplified in XL1-BLUE® E. coli. The mutated plasmid, referred hereinafter as the pcDNA 3.1 Erb001B1 hG1 plasmid, encodes for the heavy chain of Erb001B1.

Production of Erb001B1

Sterile and endotoxin-free plasmids, including the mutated pcDNA 3.1 Erb001B1 hG1 plasmid and the pcDNA 3.1 Erbitux hkappa plasmid, were prepared using the GENEELUTE™ HP Select Plasmid Gigaprep Kit (Sigma-Aldrich) following the manufacturer's instructions. Mutated pcDNA 3.1 Erb001B1 hG1 was resuspended in 2.5 mL elution buffer (1.3 mg mL$^{-1}$) and pcDNA 3.1 Erbitux hkappa was resuspended in 5 mL elution buffer (2.9 mg mL$^{-1}$).

The mutated pcDNA 3.1 Erb001B1 hG1 plasmid and the pcDNA 3.1 Erbitux hkappa plasmid were each transfected into HEK293 cells using the following procedure. HEK293F cells were unfrozen and expanded in FREESTYLE™ 293 Expression medium (Life technologies) until reaching 2.5 L with a cell density of 1.2×10$^6$ cells mL$^{-1}$ in 5 separated 2 L ERLENMEYER® flasks (Becton and Dickinson) each with 0.5 L of the 2.5 L. Five aliquots of PEI-plasmid mixture were prepared with a PEI to plasmid DNA molar ratio of 3:1. Specifically, 1.25 mg of each plasmid was diluted in 2.5 mL of FREESTYLE™ medium (Mix A). 0.5 mL of Mix A was diluted in 50 mL of FREESTYLE™ medium containing 1.5 mg of PEI (PolySciences). This step was repeated 5 times (one per each ERLENMEYER® flask of HEK293 cells). Each aliquot of PEI-plasmid mixture was vortexed and incubated for 15 minutes at room temperature. After incubation, each aliquot of PEI-plasmid mixture was added to one of the ERLENMEYER® flasks with HEK293 cells, and incubated at 37° C., 8% $CO_2$ and 150 rpm for 5 days to produce Erb001B1 comprising the mutant heavy chain of cetuximab and the wildtype light chain of cetuximab.

Purification of Erb001B1

After 5 days of production, cells were separated from the medium containing the Erb001B1 antibody by two sequential centrifugation steps at 6,000g for 25 minutes each. The supernatant was filtered through a 0.22 am sterile filter (Merck-Millipore). Erb001B1 was separated from the supernatant using a 5 mL HITRAP™ protein G column (GE Healthcare) following the manufacturer's instructions. 5 mL fractions were eluted with 0.1 mM glycine-HCl (pH 2.7) buffer, and the pH of each fraction was adjusted with 0.6 mL of IM Tris-HCl (pH 9). The fractions containing Erb001B1 were pooled and dialyzed against PBS (Sigma-Aldrich) using a D-TUBE™ Dialyzer Mega (Novagen). 1 mL aliquots of Erb001B1 were stored at −80° C. Concentrations of Erb001B1 samples were quantified using the Pierce BCA® Protein Assay Kit (Pierce) and by NANODROP® (Thermo Scientific), following the manufacturers' instructions.

Example 8. Conjugation of PEI Linkers to Erb001B1

The various PEI linkers synthesized as in Examples 1-6 were covalently conjugated to the engineered cetuximab, Erb001B1, via transglutamination reactions catalyzed by the enzyme transglutaminase. Conjugates of engineered cetuximab and PEI linkers are referred herein as mEr-PEI. In particular, conjugates of Erb001B1 and PEI are referred hereinafter as Erb001B1-PEI. Success of the transglutamination reactions, i.e. formation of the mEr-PEI conjugates, were monitored by electrophoresis on SDS-PAGE gels.

Preparation of Erb00B1-RF8

Erb001B1-RF8 conjugates were prepared using the following transglutamination reaction conditions. 150 μg of Erb001B1 and 180 μg of RF8 were diluted in 300 μL of Tris Buffered Saline (25 mM Tris-HCl pH8, 150 mM NaCl) supplemented with 6 μg of transglutaminase (Ajinomoto Products). This mixture was incubated for 16 hours at 37° C. The Erb001B1-RF8 conjugate was isolated from the mixture by five sequential centrifugation steps at 14,000 g and 2 minutes per step in a 0.5 mL AMICON® ultra microcentrifuge tube with a 30 KDa-cutoff ULTRACEL® filter. Clean Tris Buffered Saline was added to the centrifuged sample until reaching a total volume of 0.5 mL before each centrifugation step. The final Erb001B1-RF8 solution was sterile-filtered through a 0.22 m filter (Merck-Millipore).

Other mEr-PEI conjugates were prepared and purified with similar procedure as the Erb001B1-RF8 conjugate above. The volumes of the antibody and PEI solutions may be adjusted to screen for optimized transglutamination reaction conditions. Concentrations of the mEr-PEI conjugates were quantified using NANODROP®.

Detection of mEr-PEI Conjugates

The transglutamination reaction samples were analyzed by SDS-PAGE electrophoresis on 12.5% polyacrylamide gels following standard procedures (Current Protocols in Molecular Biology, Ausubel et al.). Samples were diluted in 1× Laemmli buffer, but not boiled to avoid destabilization of the PEI linkers. SDS-PAGE gels were stained with Coomassie Brilliant Blue (Sigma-Aldrich).

FIG. 2 shows SDS-PAGE analysis results of transglutamination reaction samples comprising Erb001B1, RF8 or transglutaminase, with various Erb001B1 to RF8 molar ratios. Under the tested reaction conditions, Erb001B1 yielded two bands corresponding to apparent molecular weights of 27 kDa (light chain, monomer) and 90 kDa (heavy chain, dimer) respectively. An electrophoretic shift of the Erb001B1 heavy chain was detected (i.e., smear above the 90 kDa band) only in samples containing Erb001B1, RF8 (i.e., a PEI with linker), and transglutaminase (lanes 6, and 8 of FIG. 2). This shift was not observed in samples containing only RF8 and Erb001B1, but no transglutaminase (lanes 5 and 7 of FIG. 2). In addition, no electrophoretic shift of the heavy chain band or the light chain band was observed in the absence of RF8 even in the presence of the transglutaminase (lane 4 of FIG. 2). Finally, light chains did not exhibit an electrophoretic shift even in the presence of both RF8 and transglutaminase. These results suggest successful transglutamination reaction and site-specific conjugation between Erb001B1 and RF8. The Erb001B1-RF8 conjugates yielded distinct and consistent smears on SDS-PAGE gels, and they were heavily stained by Coomassie Blue.

Conjugation Efficiency of Various PEI Samples

The various PEI compounds with linkers, including those having silyl groups (RF6, RF7, and RF8) and those synthesized by solid phase chemistry (AB7751, AB7752, AB7753, AB7769, and AB7776), were each conjugated to Erb001B1 using transglutaminase. The transglutamination reactions were performed at a molar ratio of 1:3 (Erb001B1:PEI linker) as described above and were analyzed on 12% SDS-PAGE gels.

Figure 2A:
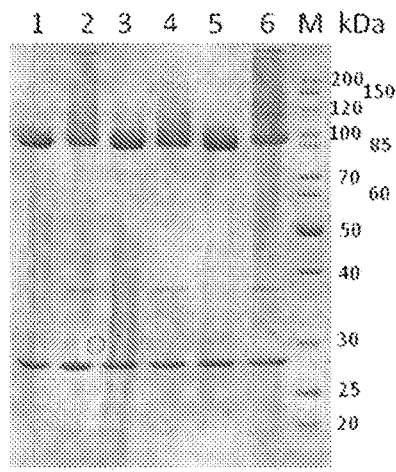
FIGS. 2A and 2B show an SDS-PAGE gel of transglutamination reaction samples comprising Erb001B1, various PEI samples, or transglutaminase (TG).
Figure 2B:
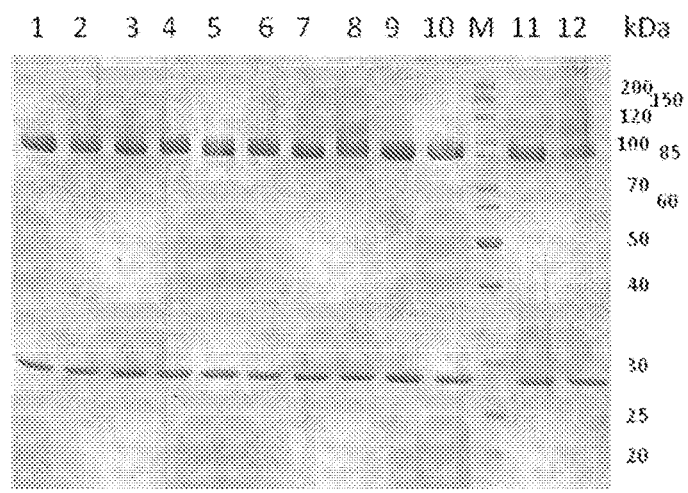

As shown in FIGS. 2A-2B, the PEI linkers were conjugated to the heavy chain of Erb001B1 via the transglutamination reactions with varying degrees of yield as demonstrated by the varying intensities of the shifted smears corresponding to the conjugates. The most favorable conjugation reaction was obtained using the RF8 sample (lane 6 of FIG. 3A and lane 12 of FIG. 3B). Densitometry tracing of the gel pictures indicated that at least 55% of the Erb001B1 heavy chain was conjugated to the PEI linker by the transglutamination reaction using the RF8 sample. Under the same reaction conditions, non-silyl-based PEI linkers, such as AB7751, AB7752, AB7753 and AB7769, also conjugated to Erb001B1, although with lower efficiency under the conditions employed (lanes 2, 4, 6, 8, and 10 of FIG. 2B).

Western Blot Analysis of Transglutamination Reaction Samples

Representative transglutamination reaction samples were further analyzed by Western blotting using an anti-human FC antibody to confirm the identity of the 90 kDa band. Samples in lanes 5 and 6 of the gel in FIG. 2A and in lanes 7 and 8 of the gel in FIG. 2B were analyzed. HRP conjugated goat anti-human IgG gamma chain antibody (Millipore, catalogue number: AP504) was used as the secondary antibody.

Figure 3:
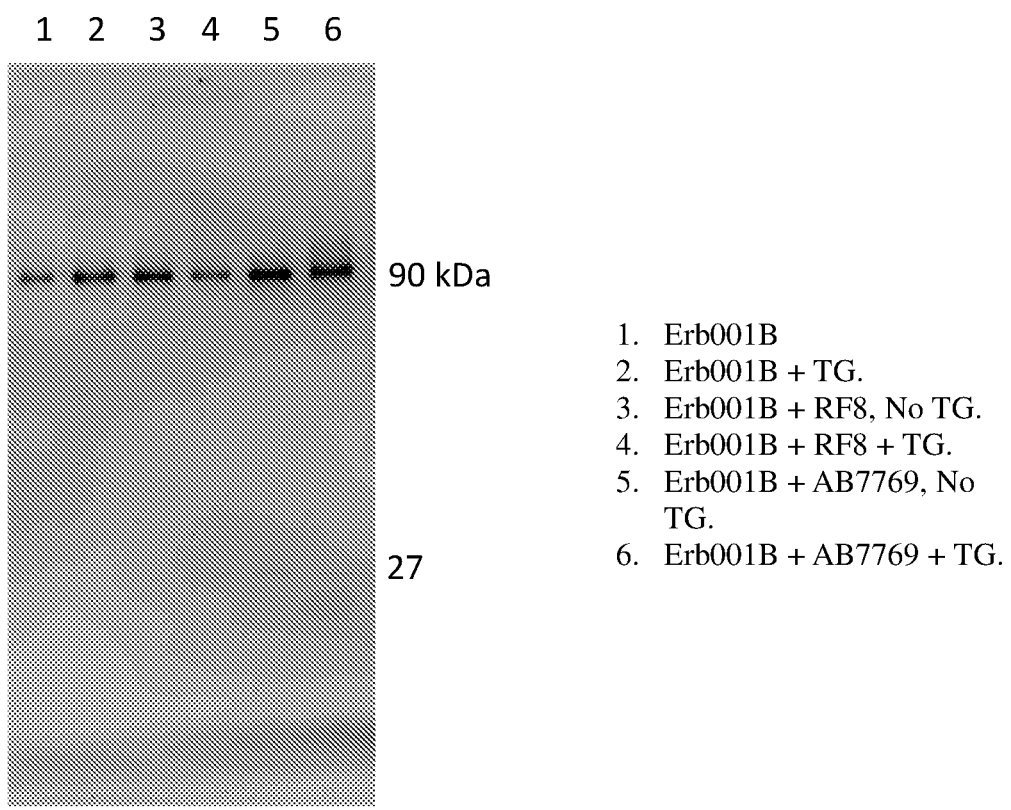
FIG. 3 shows a Western blot gel of selected transglutamination reaction samples in FIGS. 2A and 2B probed using anti-human Fc antibody.

As shown in FIG. 3, a 90 kDa band was readily detected in all of the analyzed samples, whereas a very faint signal was observed in the band corresponding to the 27 kDa light chain. This result confirms that the observed 90 kDa band corresponds to a dimer of the Erb001B1 heavy chain comprising the human Fc portion that is recognized by the anti-human FC antibody. In addition, a clear decrease in the intensity of the 90 kDa band was observed in lane 4, which results from conjugation of the heavy chain dimer of Erb001B1 with RF8. Erb001B1-RF8 conjugate has a higher molecular weight than 90 kDa, and is not easily detected by the anti-human Fc antibody.

Example 9. Cell Internalization Assay of Erb001B1-RF8

Cell internalization of the Erb001B1 antibody, and the Erb001B1-RF8 conjugate were monitored using a confocal microscopy on A431 cells that are associated with high expression levels of EGFR under serum starvation conditions. The following two experimental conditions were assessed: (1) A431 cells grown on medium with serum (i.e. low EGFR expression level) treated with the Erb001B1-RF8 conjugate; and (2) A431 cells grown on medium without serum (i.e. high EGFR expression level) treated with the Erb001B1-RF8 conjugate. As a comparison, experiments were performed in HEK293T cells that are associated with low expression levels of EGFR even under serum starvation conditions (e.g., approximately 100 times lower expression level of EGFR than A431 cells). Control experiments with Erb001B plus PEI, and PEI alone were further performed in each cell line.

Specifically, A431 cells or HEK293T cells were plated at a cell density of 50,000 cells per well in a 24-well plate (Reactiva) with a glass coverslip. Cells were first grown for 48 hours at 37° C., 10% $CO_2$ in DMEM medium (Life Technologies) with 10% of FBS (Fetal Bovine Serum, Life Technologies). A431 cells and HEK293T cells were washed for three times with serum-free DMEM medium, and grown for an additional 16 hours at 37° C., 10% $CO_2$ in DMEM medium without serum.

After the cell growth step, culture medium was removed from the cells and substituted with DMEM medium without serum containing Erb001B1 or Erb001B1-RF8 diluted to the desired concentration (4 μg $mL^{-1}$ of the Erb001B1 portion, i.e., same amount of the antibody in each set) for 5 minutes. The cells were then washed for 3 times with the corresponding DMEM medium, and further incubated at 37° C. for 1 hour or 4 hours. Each plate contained negative controls with wells having untreated cells.

After the incubation step, cells were washed three times with PBS buffer for 10 minutes, and fixed with 4% paraformaldehyde in PBS for 30 minutes at room temperature on the glass coverslips. The coverslips were further washed three times with PBS for 10 minutes, and cells were permeabilized with 0.1% TRITON® X-100 (Sigma-Aldrich) in PBS for 7 minutes at 4° C. Subsequently, the coverslips were washed again for three times with PBS. The coverslips were incubated with Blocking solution (PBS with 0.05% TWEEN® 20 (Sigma-Aldrich) and 3% BSA (Roche)) for 1 hour at room temperature.

Subsequently, the Blocking solution was removed. 50 μL of anti-Lamp1 antibody (ProSci, 1:250 dilution in Blocking solution) was added over each coverslip, and incubated for 1 hour at room temperature. After the incubation, anti-Lamp1 antibody was removed, and the coverslips were washed three times with PBS supplemented with 0.05% TWEEN® 20 for 10 minutes. 50 μL of a mixture of secondary antibodies goat anti-rabbit IgG (H+L) conjugated to ALEXA FLUOR® 488 (Life Technologies) and goat anti-human IgG (H+L) conjugated to ALEXA FLUOR® 594 (Life Technologies) were added to each coverslip at a 1:250 dilution in Blocking solution and incubated for 1 hour at room temperature. The goat anti-rabbit IgG(H+L) conjugated antibody was used to stain the anti-Lamp1 antibody, which binds to the Lamp1 protein in the lysosomes of cells. The goat anti-human IgG(H+L) conjugated antibody was used to stain the Erb001B1 antibody or the Erb001B1-RF8 conjugate.

Next, secondary antibodies were removed, and the coverslips were treated with 50 μL of Hoechst 33342 (Life technologies, nucleus stain) at 10 μg $mL^{-1}$ in PBS to stain nuclei.

After the staining steps, the coverslips were washed three times with PBS for 10 minutes, and mounted onto microscope slides (Menzel-Glaser) containing a drop of PRO-LONG® Gold Antifade Mountant (Life Technologies). Samples were allowed to dry for a minimum of 72 hour prior to examination under a Zeiss Confocal Microscope (Zeiss).

This set of experiments allowed visualization of cell internalization of the Erb001B1-RF8 conjugate under various conditions, as shown in FIGS. 4A-6. In the figures, red color indicates presence of Erb001B1 or Erb001B1-RF8, green color indicates location of the lysosomes, yellow color indicates co-localization of Erb001B1 or Erb001B1-RF8 with the lysosomes (i.e., presence of Erb001B1 or Erb001B1-RF8 in the lysosomes), and the nucleus is shown in blue as a reference.

FIGS. 4A-4B show that the Erb001B1 antibody can be internalized by A431 cells (i.e. with high expression levels of EGFR) over time. After 1 hour of incubation, red color is mostly at the surface showing that Erb001B1 binds to the receptor, while green color is seen throughout the cytoplasm as expected for lysosomes, the nucleus is stained in blue color. After 4 hours of incubation time, the internalized Erb001B1 antibody was retained mostly in surface of cells (red color on cell surface) and the lysosomes (yellow color indicating co-localization of stain for lysosomes and stain for Erb001B1) as suggested by co-localization of the lysosome stain and the Erb001B1 stain in most cells (FIG. 4B).

FIGS. 5A-5B reveal that under the experimental conditions, a significant amount of the Erb001B1-RF8 conjugate was internalized by the A431 cells (i.e. with high expression levels of EGFR). The amount of internalized Erb001B1-RF8 after 1 hour of incubation was comparable to the amount of internalized Erb001B1 alone after 4 hours of incubation under serum starvation conditions (e.g., compare FIG. 5A and FIG. 4A). FIG. 5A shows that most of the red stain is at the surface, suggesting that Erb001B1-RF8 is binding to the receptor, and most of the cytoplasm contains lysosomes stained in green, with some yellow color indicating co-localization of lysosome and Erb001B1-RF8. Notably, after 4 hours of incubation post treatment of the cells with the Erb001B1-RF8 conjugate, the conjugate was released into the cytoplasm (FIG. 5B), as suggested by the red signal in the cytoplasm. Red color is distributed throughout the cytoplasm, around blue stain (indicating nucleus), with very few green spots, suggesting that Erb001B1-RF8 has escaped the lysosomes and localized in the cytoplasm; most of the color in FIG. 5B corresponds to red (Erb001B1-RF8 in cytoplasm) and blue (nucleus), rather than green or yellow. While in cells treated with Erb001B1 alone (FIG. 4B), the Erb001B1 antibody was mainly retained in the lysosomes of the cells even at 4 hours post treatment.

Figure 6:
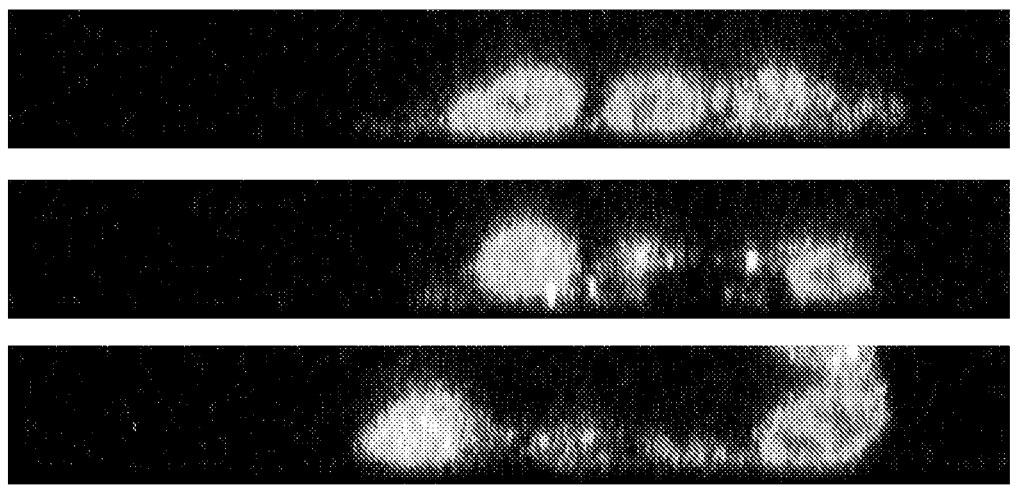
FIG. 6 shows confocal microscopy images of HEK293T cells (low EGFR expression) incubated with the Erb001B1-RF8 conjugate for 4 hours in DMEM medium without serum. Nuclei are stained in blue. Lysosomes are stained with an anti-Lamp1 antibody and shown in green. Erb001B1-RF8 is shown in red.

Furthermore, cell internalization of the Erb001B1 antibody or the Erb001B1-RF8 conjugate was dependent on a high expression level of EGFR. For example, FIG. 6 shows that there was an absence of Erb001B1 staining (red signal) in HEK293T cells after 4 hours of incubation post treatment with the Erb001B1-RF8 conjugate. This result suggests that HEK293T cells, which has low level of EGFR expression even under serum starvation conditions, do not associate or internalize the Erb001B1-RF8 conjugate. Therefore, internalization of Erb001B1-RF8 is driven by the target-specific antibody, rather than the non-target specific PEI portion of the conjugate. The experimental results were reproducible in separate sets of experiments (results not shown).

In summary, the experimental results have demonstrated that when Erb001B1 is covalently conjugated to a PEI linker (such as RF8), the conjugate can be internalized by cells expressing EGFR and released from the lysosome to the cytoplasm to achieve wide distribution inside the cells.

Example 10. Delivery of Fluorescent Oligonucleotide by Erb001B1-RF8

This example describes delivery of a fluorescently-labeled oligonucleotide into cells using the Erb001B1-RF8 conjugate, and in vivo localization of the fluorescent oligonucleotide in subcellular compartments using confocal microscopy.

200,000 A431 cells were seeded in each of four 35 mm cell culture dishes (Corning) and grown in DMEM supplemented with 10% FBS for 48 hours at 37° C. and 10% $CO_2$. The cells were washed three times with serum-free DMEM medium and grown for an additional 16 hours in serum-free DMEM medium at 37° C. and 10% $CO_2$.

Subsequently, 375 pmols of oligonucleotide with a sequence of 5'-CAACTGCAGTAGTTGTTAAAC-3' (SEQ ID NO: 24) conjugated to 6-FAM™ (6-carboxyfluorescein, Sigma-Aldrich; referred hereinafter as 6-FAM-oligonucleotide) was mixed with 56 µg of the Erb001B1-RF8 conjugate at a final concentration of 25 µg $mL^{-1}$ in 0.25 mL of serum-free DMEM. The mixture was vortexed and incubated for 15 minutes at room temperature.

After the incubation step, the serum-free DMEM medium in each of the cell culture dishes was removed and substituted by 2 mL of fresh serum-free DMEM. The 6-FAM-oligonucleotide mixture described above was added to cells in one culture dish, and incubated for 4 hours at 37° C. and 10% $CO_2$.

The cells were stained without fixation as follows. Two hours before examining the cells under the confocal microscope, LYSOTRACKER RED® (Life Technologies) was added to cells of each culture dish at a final concentration of 75 nM in order to stain the lysosomes. Before examination, Hoechst 33342 at a final concentration of 10 µg $mL^{-1}$ and CELLMASK™ Deep Red Plasma Membrane Stain (Life Technologies) at 1:1 000 dilution were added to cells in each culture dish, and incubated for 5 minutes at room temperature, in order to stain the nuclei and the cell membrane, respectively. Cells were examined under a Zeiss Confocal Microscope (Zeiss). 6-FAM fluorescence signal from the 6-FAM-oligonucleotide was observed in the green channel.

The confocal microscopy images of the cells treated with the 6-FAM-oligonucleotide mixture with Erb001B1-RF8 conjugate are shown in FIG. 7. At 25 µg/mL, the Erb001B1-RF8 conjugate was capable of delivering the 6-FAM-oligonucleotide to the nuclei, as evident in the co-localization of the 6-FAM signal (green) with the nuclei signal (blue) in some cells.

What is claimed is:

1. A compound of formula (VII):

(VII)

$R^5-N(H)-[CH_2-N(H)]_n-CH_2-O-Si(R^1)(R^2)-L^1-N(R^3)(R^{4p})$ or a salt thereof, wherein $R^1$ and $R^2$ are independently optionally substituted $C_{1-6}$ alkyl, optionally substituted aryl, or optionally substituted heteroaryl;

$R^3$ is hydrogen or $C_{1-6}$ alkyl;

$R^{4p}$ is a polypeptide, wherein the linkage between $R^{4p}$ and N is with an acyl donor glutamine tag from the polypeptide;

$R^5$ is hydrogen or optionally substituted $C_{1-6}$ alkyl;

n is a number from one to 1200;

$L^1$ is $-(CH_2)_a-$, $-(CH_2)_a-NH-C(O)-NH-(CH_2)_b-$, $-(CH_2)_a-C(O)-NH-(CH_2)_b-$, or $-(CH_2)_a-NH-C(O)-(CH_2)_b-$;

a is a number from one to 20; and b is a number from one to 20.

2. The compound of claim 1, wherein $R^{4p}$ is a targeting polypeptide.

3. The compound of claim 1, wherein $R^{4p}$ is an Fc-containing polypeptide or a Fab-containing polypeptide.

4. The compound of claim 3, wherein $R^{4p}$ is an antibody.

5. The compound of claim 3, wherein $R^{4p}$ specifically binds to an intracellular molecule.

6. The compound of claim 3, wherein $R^{4p}$ specifically binds to an extracellular molecule.

7. The compound of claim 4, wherein $R^{4p}$ is a multispecific antibody.

8. The compound of claim 7, wherein the multispecific antibody comprises a first binding domain that specifically binds to an extracellular molecule and a second binding domain and specifically binds to an intracellular molecule.

9. A compound of the formula (VIII):

(VIII)

$R^{11}-N(H)-[CH_2-N(H)]_n-CH_2-O-L^2-N(H)-C(O)-O-R^{10}$ or a salt thereof, wherein $R^{10}$ is a solid phase resin;

$R^{11}$ is hydrogen or optionally substituted $C_{1-6}$ alkyl;

n is a number from one to 1200;

$L^2$ is $-(C_6H_4)-(CH_2)_c-$, $-(C_6H_4)-NH-(CH_2)_c-$, $-(C_6H_4)-C(O)-NH-(CH_2)_c-$, $-(C_6H_4)-NH-(CH_2CH_2O)_d-CH_2CH_2-$, or $-(C_6H_4)-C(O)-NH-(CH_2CH_2O)_d-CH_2CH_2-$;

c is a number from one to 10; and d is a number from one to 10.

10. A compound of the formula (X):

(X)

$R^{11}-N(H)-[CH_2-N(H)]_n-CH_2-O-L^2-N(R^{12})(R^{13p})$ or a salt thereof, wherein $R^{11}$ is hydrogen or optionally substituted $C_{1-6}$ alkyl;

$R^{12}$ is hydrogen or optionally substituted $C_{1-6}$ alkyl;

$R^{13p}$ is a polypeptide, wherein the linkage between $R^{13p}$ and N is with an acyl donor glutamine tag from the polypeptide;

n is a number from one to 1200;

$L^2$ is $-(C_6H_4)-(CH_2)_c-$, $-(C_6H_4)-NH-(CH_2)_c-$, $-(C_6H_4)-C(O)-NH-(CH_2)_c-$, $-(C_6H_4)-NH-(CH_2CH_2O)_d-CH_2CH_2-$, or $-(C_6H_4)-C(O)-NH-(CH_2CH_2O)_d-CH_2CH_2-$;

c is a number from one to 10; and d is a number from one to 10.

11. A compound of the formula (XIII):

(XIII)

$HO-[CH_2-N(H)]_n-CH_2-N(R^{14})-L^3-N(R^{17})(R^{18p})$ or a salt thereof, wherein $R^{14}$ is hydrogen, optionally substituted $C_{1-6}$ alkyl, or $R^{16}-N(R^{15})-[CH_2-N(H)]_p-CH_2-$ ;

$R^{15}$ is hydrogen or optionally substituted $C_{1-6}$ alkyl;

$R^{16}$ is hydrogen or optionally substituted $C_{1-6}$ alkyl;

$R^{17}$ is hydrogen or optionally substituted $C_{1-6}$ alkyl;

$R^{18p}$ is a polypeptide, wherein the linkage between $R^{18p}$ and N is with an acyl donor glutamine tag from the polypeptide;

n is a number from one to 1200;

p is a number from one to 1200;

$L^3$ is $-C(O)-(C_6H_4)-(CH_2)_e-$ or $-C(O)-(CH_2)_e-$; and e is a number from one to 10.

* * * * *

SEQUENCE LISTING

```
<160> NUMBER OF SEQ ID NOS: 24

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 4
<223> OTHER INFORMATION: Xaa = Any Amino Acid

<400> SEQUENCE: 1

Xaa Xaa Gln Xaa
1

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Leu Leu Gln Gly Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3
```

```
Leu Leu Gln Gly Ala
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic Construct

<400> SEQUENCE: 4

Leu Leu Gln Gly
1

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Any Amino Acid

<400> SEQUENCE: 5

Leu Pro Xaa Thr Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Construct

<400> SEQUENCE: 6

Leu Cys Thr Pro Ser Arg
1               5

<210> SEQ ID NO 7
<211> LENGTH: 452
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125
```

```
Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 8
<211> LENGTH: 213
<212> TYPE: PRT
<213> ORGANISM: Artificial Sequence
<220> FEATURE:
<223> OTHER INFORMATION: Synthetic Construct

<400> SEQUENCE: 8

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30
```

-continued

```
Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Ala
        210

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

Pro Trp Glu Glu Gln Tyr Asn Ser Thr
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Val Leu Asn Leu Ala Gln Ser Lys Asn Phe His
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Ala Pro Ala Leu Gln Pro Thr Gln Gly Ala Met
1               5                   10

<210> SEQ ID NO 12
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 12

Ile Pro Lys Glu Gln Lys Tyr Ser Phe
1               5

<210> SEQ ID NO 13
<211> LENGTH: 13
<212> TYPE: PRT
<213> ORGANISM: Artificial Sequence
<220> FEATURE:
<223> OTHER INFORMATION: Synthetic Construct

<400> SEQUENCE: 13

Met Gly Gly Ser Pro Leu Ala Gln Ser His Gly Gly Ser
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Lys Glu Thr Ala Ala Ala Lys Phe Glu Arg Gln His Met Asp Ser
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: Synthetic Construct

<400> SEQUENCE: 15

Thr Glu Tyr Gly Leu Phe Gln Ile Asn Asn Asp Ser
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct

<400> SEQUENCE: 16

Trp Ala Leu Gln Arg Pro His
1               5

<210> SEQ ID NO 17
<211> LENGTH: 12
<212> TYPE: PRT
<213> ORGANISM: Artificial Sequence
<220> FEATURE:
<223> OTHER INFORMATION: Synthetic Construct

<400> SEQUENCE: 17

Trp Ala Leu Gln Arg Pro Tyr Thr Leu Thr Glu Ser
1               5                   10

<210> SEQ ID NO 18
<211> LENGTH: 12
<212> TYPE: PRT
```

<213> ORGANISM: Artificial Sequence
<220> FEATURE:
<223> OTHER INFORMATION: Synthetic Construct

<400> SEQUENCE: 18

Trp Ala Leu Gln Arg Pro His Tyr Ser Tyr Pro Asp
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Construct

<400> SEQUENCE: 19

Trp Ser Pro Ile Pro Gln Met Arg Thr Val Pro Pro
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic Construct

<400> SEQUENCE: 20

Asn Pro Lys Ile Tyr Pro Met Gln Gly Trp Phe Val
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Construct

<400> SEQUENCE: 21

Tyr Glu Leu Gln Arg Pro Tyr His Ser Glu Leu Pro
1               5                   10

<210> SEQ ID NO 22
<211> LENGTH: 27
<212> TYPE: DNA
<213> ORGANISM: Artificial Sequence
<220> FEATURE:
<223> OTHER INFORMATION: Synthetic Construct

<400> SEQUENCE: 22
gccagcacgt accgtgtggt cagcgtc                                         27

<210> SEQ ID NO 23
<211> LENGTH: 23
<212> TYPE: DNA
<213> ORGANISM: Artificial Sequence
<220> FEATURE:
<223> OTHER INFORMATION: Synthetic Construct

<400> SEQUENCE: 23
gtactgctcc tcccgcggct ttg                                             23

<210> SEQ ID NO 24
<211> LENGTH: 21
<212> TYPE: DNA
<213> ORGANISM: Artificial Sequence
<220> FEATURE:
<223> OTHER INFORMATION: Synthetic Construct

```
<400> SEQUENCE: 24
caactgcagt agttgttaaa c                                               21
```